US008282917B2

(12) United States Patent
Bell et al.

(10) Patent No.: US 8,282,917 B2
(45) Date of Patent: *Oct. 9, 2012

(54) MUTANT VIRUSES AND USES THEREOF

(75) Inventors: John C. Bell, Ottawa (CA); Brian D. Lichty, Brantford (CA); David F. Stodjl, Ottawa (CA)

(73) Assignees: Wellstat Biologics Corporation, Gaithersburg, MD (US); Ottawa Hospital Research Institute, Ottawa, Ontario (CA)

( * ) Notice: Subject to any disclaimer, the term of this patent is extended or adjusted under 35 U.S.C. 154(b) by 82 days.

This patent is subject to a terminal disclaimer.

(21) Appl. No.: 12/750,410

(22) Filed: Mar. 30, 2010

(65) Prior Publication Data

US 2010/0272687 A1    Oct. 28, 2010

Related U.S. Application Data

(63) Continuation of application No. 10/551,103, filed as application No. PCT/CA2004/000460 on Mar. 29, 2004, now Pat. No. 7,731,974.

(60) Provisional application No. 60/457,591, filed on Mar. 27, 2003.

(51) Int. Cl.
    A61K 35/76    (2006.01)
(52) U.S. Cl. .................................. 424/93.2; 424/93.6
(58) Field of Classification Search .................. None
    See application file for complete search history.

(56) References Cited

U.S. PATENT DOCUMENTS

| | | | |
|---|---|---|---|
| 4,215,051 A | 7/1980 | Schroeder et al. | |
| 4,769,330 A | 9/1988 | Paoletti et al. | |
| 6,022,726 A | 2/2000 | Palese et al. | |
| 6,110,461 A | 8/2000 | Lee et al. | |
| 6,296,845 B1 | 10/2001 | Sampson-Johannes et al. | |
| 6,440,422 B1 | 8/2002 | Sutter et al. | |
| 6,451,323 B1 | 9/2002 | Garcia-Sastre et al. | |
| 6,468,544 B1 | 10/2002 | Egorov et al. | |
| 6,497,873 B1 | 12/2002 | Whitt et al. | |
| 6,531,123 B1 | 3/2003 | Chang | |
| 7,731,974 B2 * | 6/2010 | Bell et al. ................... | 424/199.1 |
| 2005/0260601 A1 | 11/2005 | Whitt et al. | |

FOREIGN PATENT DOCUMENTS

| | | |
|---|---|---|
| WO | 96/03997 | 2/1996 |
| WO | 97/26904 | 7/1997 |
| WO | 99/18799 | 4/1999 |
| WO | 00/62735 | 10/2000 |
| WO | 01/19380 | 3/2001 |
| WO | WO 01/19380 * | 3/2001 |
| WO | 2004/022716 | 3/2004 |

OTHER PUBLICATIONS

Brun et al (Molecular Therapy 18:1440-1449, 2010) (plus supplement S1).*

Atreya, et al., "Amino acid substitutions in the coat protein result in loss of insect transmissibility of a plant virus", Proc. Natl. Acad. Sci., USA, 88:7887-7891, Sep. 1991.
Browne, et al., "Characterization of herpes simplex virus type 1 recombinants with mutations in the cytoplasmic tail of glycoprotein H", Journal of General Virology, 77:2569-2573, 1996.
Imamichi, et al., "Relative Replication Fitness of a High-Level 3'-Azido-3'-Deoxythymidine-Resistant Variant of Human Immunodeficiency Virus Type 1 Possessing an Amino Acid Deletion at Codon 67 and a Novel Substitution (Thr→Gly) at Codon 69", Journal of Virology, 74(23):10958-10964, Dec. 2000.
Petersen, et al., "The Matrix Protein of Vesicular Stomatitis Virus Inhibits Nucleocytoplasmic Transport When it is in the Nucleus and Associated with Nuclear Pore Complexes", Molecular and Cellular Biology, 20(22): 8590-8601, Nov. 2000.
Desforges, et al.,"Different host-cell shutoff strategies related to the matrix protein lead to persistence of vesicular stomatitis virus mutant on fibroblast cell", Virus Research, 76(1): 87-102, Jul. 2001.
von Kobbe, et al., "Vesicular Stomatitis Virus Matrix Protein Inhibits Host Cell Gene Expression by Targeting the Nucleoporin Nup98", Molecular Cell, 6: 1243-1252, Nov. 2000.
Desforges, et al., "Matrix Protein Mutations Contribute to Inefficient Induction of Apoptosis Leading to Persistent Infection of Human Neural Cells by Vesicular Stomatitis Virus", Virology, 295(1): 63-73, Mar. 2002.
Jayakar, et al., "Identification of Two Additional Translation Products from the Matrix (M) Gene That Contribute to Vesicular Stomatitis Virus Cytopathology", Journal of Virology, 76(16): 8011-8018, Aug. 2002.
Stojdl, et al., "Exploiting tumor-specific defects in the interferon pathway with a previously unknown oncolytic virus", Nature Medicine, 6(7): 821-825, Jul. 2000.
Balachandran, et al., "Oncolytic Activity of Vesicular Stomatitis Virus is Effective against Tumor Exhibiting Aberrant p53, Ras, or Myc Function and involves the Induction of Apoptosis", Journal of Virology, 75(7):3474-3479, Apr. 2001. Petersen, et al., "Multiple vesiculoviral matrix proteins inhibit both nuclear export and import", Proceedings of the National Academy of Science of the United States of America, 98(15): 8590-8595, Jul. 2001.
Stojdl, et al., "VSV strains with defects in their ability to shutdown innate immunity are potent systemic anti-cancer agents", Cancer Cell, 4(4): 263-275, Oct. 2003.
Ahmed, et al., "Ability of the Matrix Protein of Vesicular Stomatitis Virus to Suppress Beta Interferon Gene Expression is Genetically Correlated with the Inhibition of Host RNA and Protein Synthesis", Journal of Virology, 77(8): 4646-4657 Apr. 2003.

(Continued)

*Primary Examiner* — Mary E Mosher
(74) *Attorney, Agent, or Firm* — Douglas A. Golightly; Lewis J. Kreisler

(57) ABSTRACT

The present invention provides mutant viruses with a decreased ability to block nuclear transport of mRNA or protein in an infected cell which are attenuated in vivo. The mutant viruses of the present invention may also be capable of triggering the anti-viral systems of normal host cells while remaining sensitive to the effects of these systems. The present invention further provides for the use of the mutant viruses in a range of applications including, but not limited to, as therapeutics for the treatment of cancer and infections, as vaccines and adjuvants, as viral vectors, and as oncolytic and cytolytic agents for the selective lysis of malignant or infected cells.

25 Claims, 31 Drawing Sheets

OTHER PUBLICATIONS

Specht, et al., "Dendritic Cells Retrovirally Transduced with a Model Antigen Gene are Therapeutically Effective against Established Pulmonary Metastases", The Journal of Experimental Medicine, 186(8): 1213-1221, Oct. 1997.

Terstegen, et al., "The Vesicular Stomatitis Virus Matrix Protein Inhibits Glycoprotein 130-Dependent STAT Activation", The Journal of Immunology, 167: 5209-5216, 2001.

Her, et al., "Inhibition of Ran Guanosine Triphosphatase-Dependent Nuclear Transport by the Matrix Protein of Vesicular Stomatitis Virus", Science, 276: 1845-1847, Jun. 1997.

Lu, et al., "Regulation of the Promoter Activity of Interferon Regulatory Factor-7 Gene", The Journal of Biological Chemistry, 275(41): 31805-31812, Oct. 2000.

Zhang, et al., "IRF-7, a New Interferon Regulatory Factor Associated with Epstein-Barr Virus Latency", Molecular and Cellular Biology, 17(10): 5748-5757, Oct. 1997.

Wathelet, et al., "Virus Infection Induces the Assembly of Coordinately Activated Transcription Factors on the IFN-B Enhancer in Vivo", Molecular Cell, 1: 507-518, Mar. 1998.

Lawson, et al., "Recombinant Vesicular Stomatitis Viruses from DNA", Proc. Natl. Acad. Sci., 92: 4477-4481, May 1995.

Novella, et al., "Large-Population Passages of Vesicular Stomatitis Virus in Interferon-Treated Cells Select Variants of Only Limited Resistance", Journal of Virology, 70(9): 6414-6417, Sep. 1996.

Yuan, et al., "Inhibition of Host Transcription by Vesicular Stomatitis Virus Involves a Novel Mechanism that is Independent of Phosphorylation of TATA-Binding Protein (TBP) or Association of TBP with TBP-Associated Factor Subunits", Journal of Virology, 75(9): 4453-4458, May 2001.

Lin, et al., "Multiple Regulatory Domains Control IRF-7 Activity in Response to Virus Infection", The Journal of Biological Chemistry, vol. 275(44): 34320-34327, Nov. 2000.

Bell, et al., "Getting Oncolytic Virus Therapies off the Ground", Cancer Cell, 4: Jul. 7-11, 2003.

Ferran, et al., "The Vesicular Stomatitis Virus Matrix Protein Inhibits Transcription from the Human Beta Interferon Promoter", Journal of Virology, 71(1): 371-377, Jan. 1997.

Zhang, et al., "Interferon Regulatory Factor 7 Mediates Activation of Tap-2 by Epstein-Barr Virus Latent Membrane Protein 1", Journal of Virology, 75(1): 341-350, Jan. 2001.

Stojdl, et al., "The Murine Double-Stranded RNA-Dependent Protein Kinase PKR is Required for Resistance to Vesicular Stomatitis Virus", Journal of Virology, 74(20): 9580-9585, Oct. 2000.

Steinhoff, et al., "Antiviral Protection by Vesicular Stomatitis Virus-Specified Antibodies in Alpha/Beta Interferon Receptor-Deficient Mice", Journal of Virology, 69(4): 2153-2158, Apr. 1995.

Jayakar, et al., "Mutation in the PPPY Motif of Vesicular Stomatitis Virus Matrix Protein Reduce Virus Budding by Inhibiting a Late Step in Virion Release", Journal of Virology, 74(21): 9818-9827, Nov. 2000.

Racaniello, et al., "Cloned Poliovirus Complementary DNA is Infectious in Mammalian Cells", Science, 214: 916-918, Nov. 1981.

Roberts, et al., "Recovery of Negative-Strand RNA Viruses from Plasmid DNAs: A Positive Approach Revitalizes a Negative Field", Virology, 247: 1-6, 1998.

Necomb, et al., "In Vitro Reassembly of Vesicular Stomatitis Virus Skeletons", Journal of Virology, 41(3): 1055-1062, Mar. 1982.

Blondel, et al., "Role of Matrix Protein in Cytopathogenesis of Vesicular Stomatitis Virus", Journal of Virology, 64(4): 1716-1725, Apr. 1990.

Lyles, et al., "Potency of Wild-type and Temperature-Sensitive Vesicular Stomatitis Virus Matrix Protein in the Inhibition of Host-Directed Gene Expression", Virology, 225: 172-180, 1996.

Francoeur, et al., "The Isolation of Interferon-Inducing Mutants of Vesicular Stomatitis Virus with Altered Viral P Function for the Inhibition of Total Protein Synthesis", Virology, 160: 236-245, 1987.

Sato, et al., "Positive Feedback Regulation of Type I IRF Genes by the IFN-inducible Transcription Factor IRF-7", FEBS Letters, 441: 106-110, 1998.

Lambright, et al., "Oncolytic Therapy Using a Mutant Type-1 Herpes Simplex Virus and the Role of the Immune System", The Society of Thoracic Surgeons, 68: 1756-1762, 1999.

DiDonato, et al., "A cytokine-responsive IkB Kinase that activates the transcription factor NF-kB", Nature, 388: 548-554, Aug. 1997.

Morin, et al., "Preferential Binding Sites for Interferon Regulatory Factors 3 and 7 Involved in Interferon-A Gene Transcription", J. Mol. Biol., 316: 1009-1022, Mar. 2002.

Ikeda, et al, "Oncolytic Virus Therapy of Multiple Tumors in the Brain Requires Suppression of Innate and Elicited Antiviral Responses", Nature Medicine, 5(8): 881-887, Aug. 1999.

Todo, et al., "Systemic Antitumor Immunity in Experimental Brain Tumor Therapy using a Multimutated, Replication-Competent Herpes Simplex Virus", Human Gene Therapy, 10: 2741-2755, Nov. 1999.

Fisher, et al., "Polymer-coated Adenovirus Permits Efficient Retargeting and Evades Neutralising Antibodies", Gene Therapy, 8: 341-348, 2001.

Schnell, et al., "The Minimal Conserved Transcription Stop-Start Signal Promotes Stable Expression of a Foreign Gene in Vesicular Stomatitis Virus", Journal of Virology, 70(4): 2318-2323, Apr. 1996.

Litchty, et al., "Matrix protein of Vesicular stomatitis virus harbours a cryptic mitochondrial-targeting motif", Journal of Virology, 87: 3379-3384, 2006.

Descotes, et al., "Clinical immunotoxicity of therapeutic proteins", Expert Opinion on Drug Metabolism and Toxicology, 4(12): 1537-1549, 2008.

Barber, "Vesicular Stomatitis Virus as an Oncolytic Vector", Viral Immunology, 17(4): 516-527, Dec. 2004.

* cited by examiner

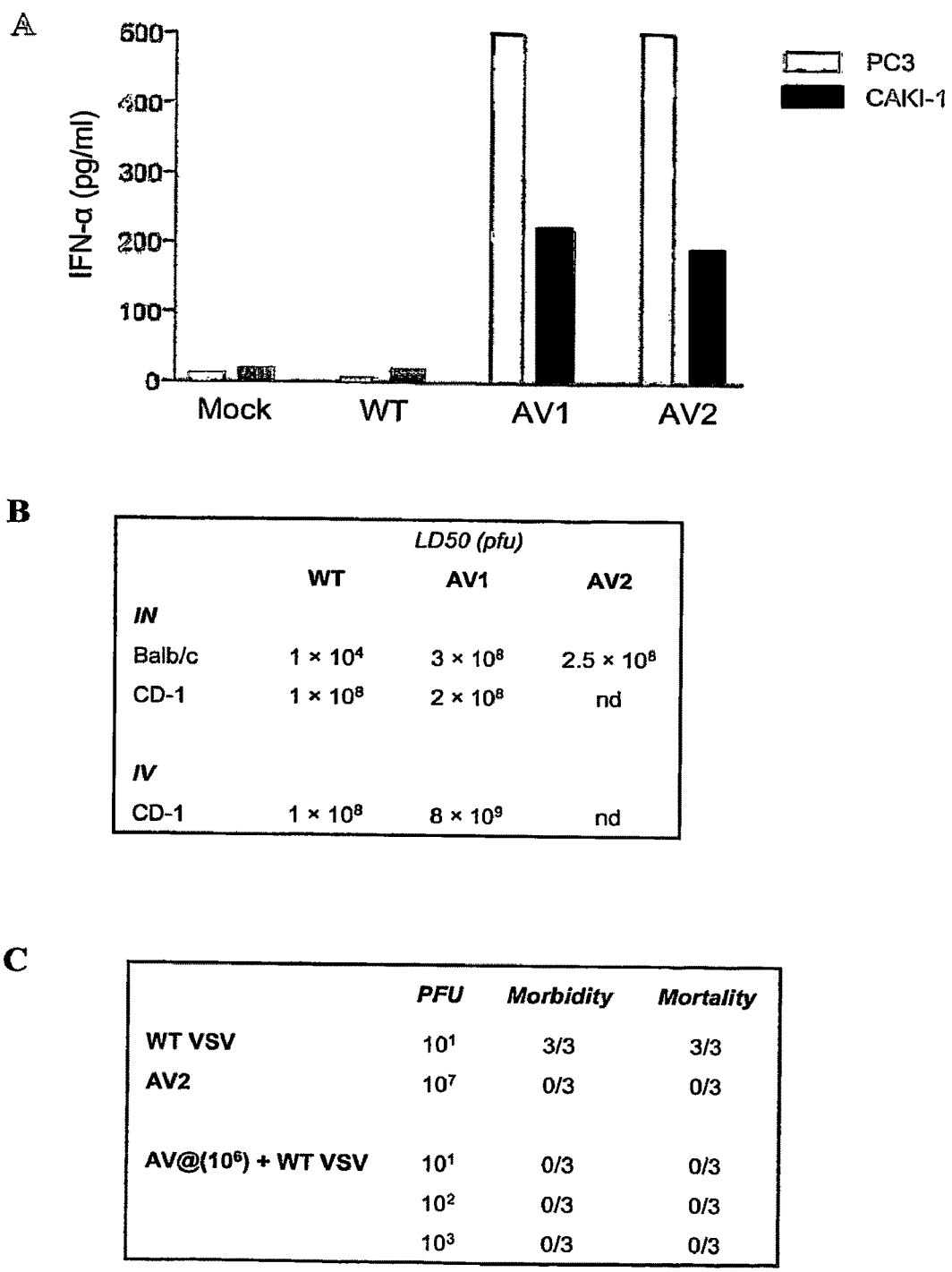
FIGURE 1A-C

FIGURE 1D

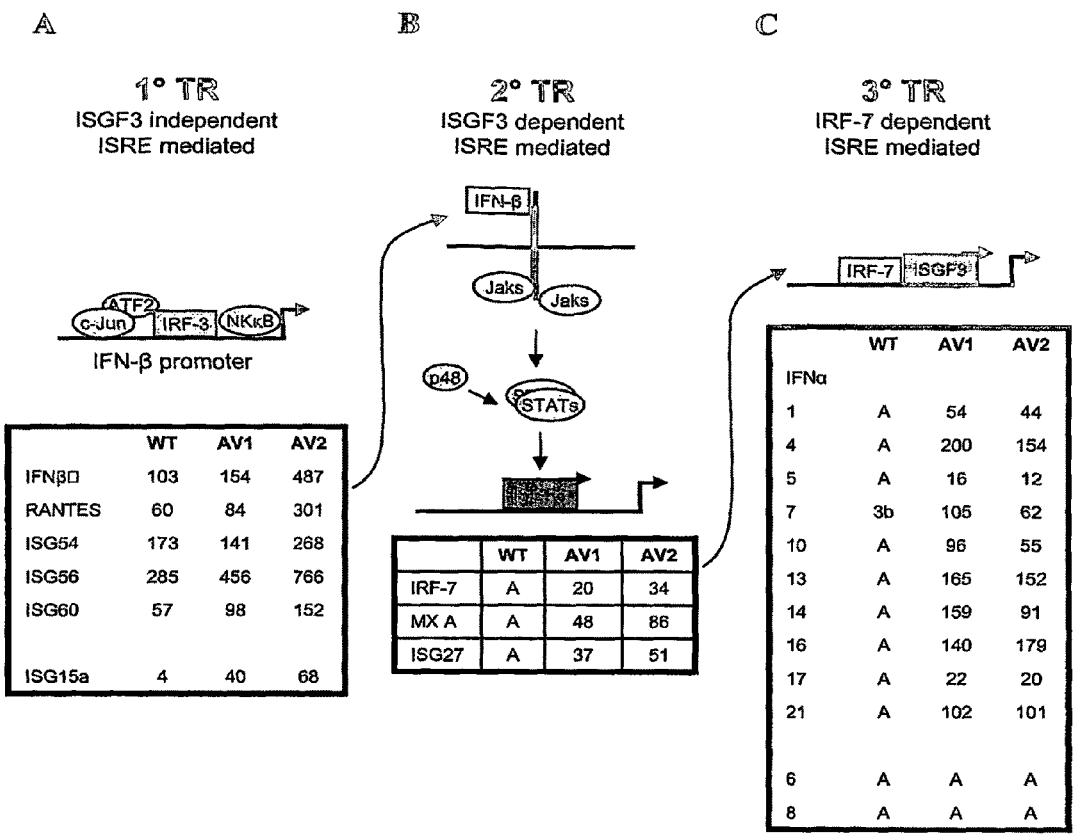
FIGURE 2A-C

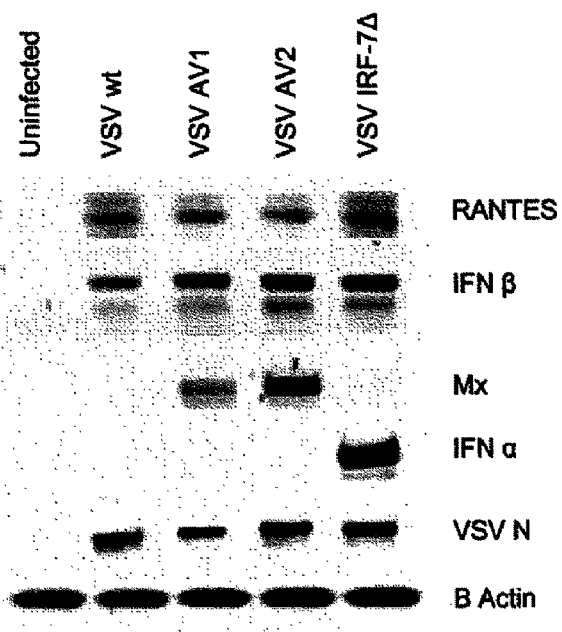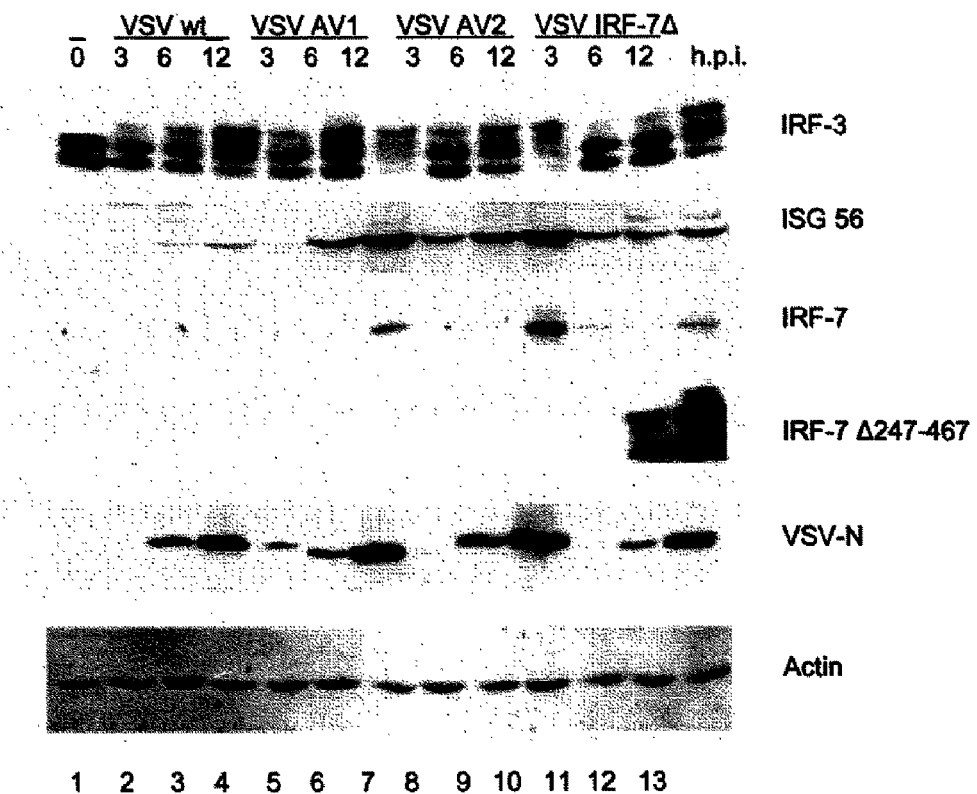
FIGURE 2D-E

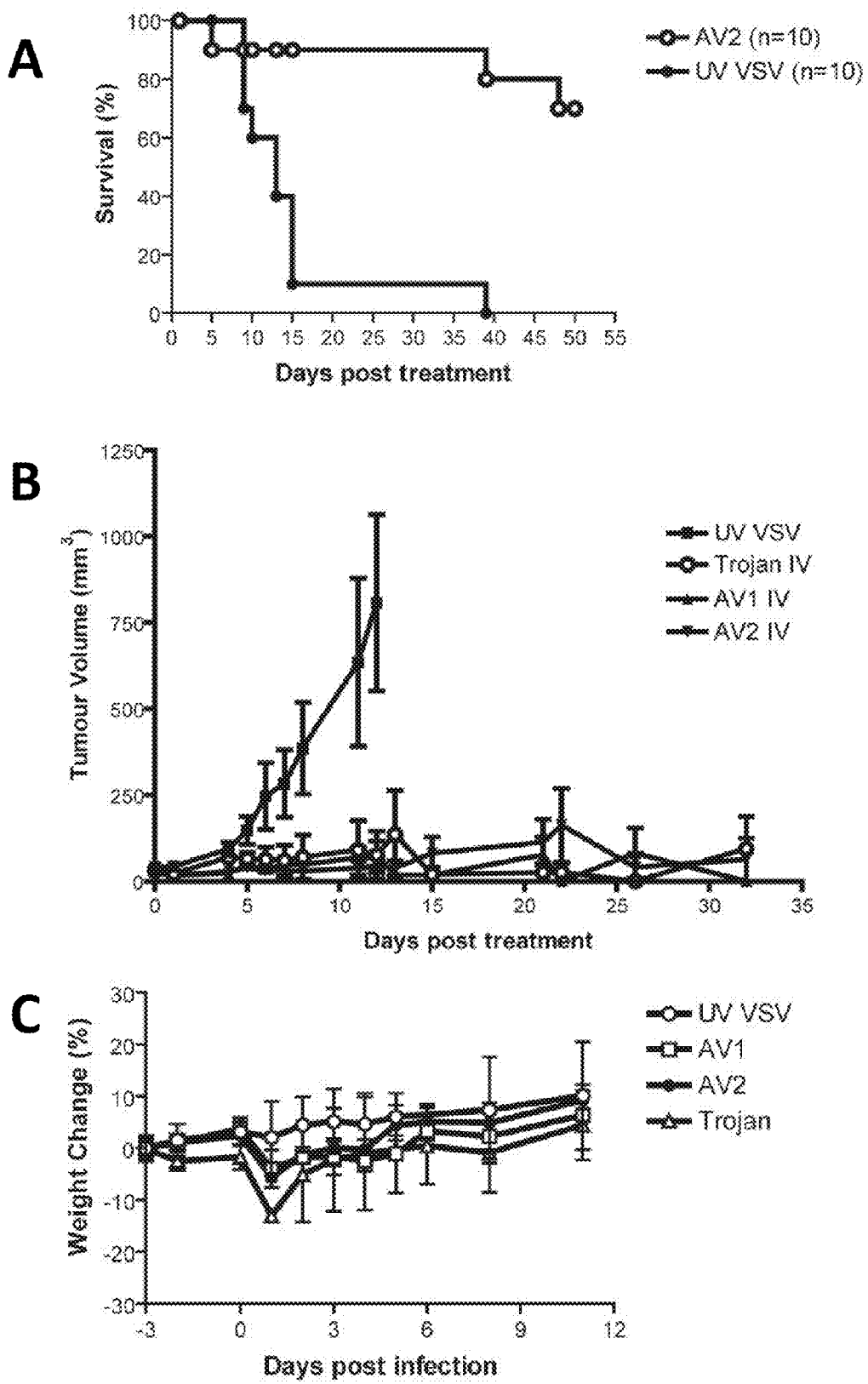
FIGURE 4A-C

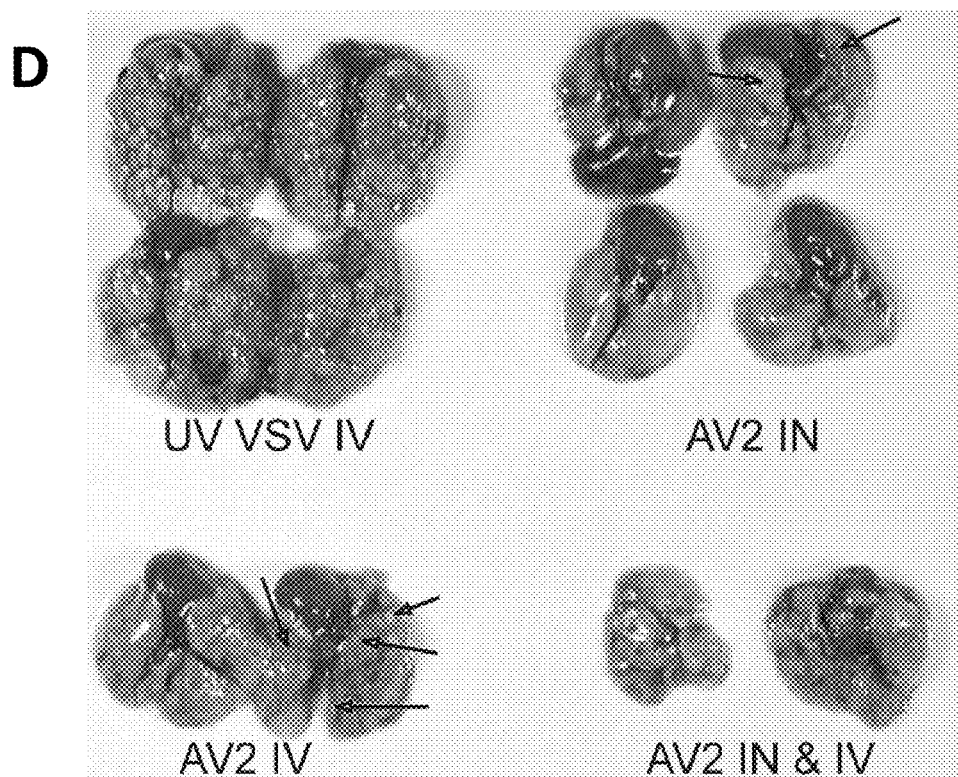
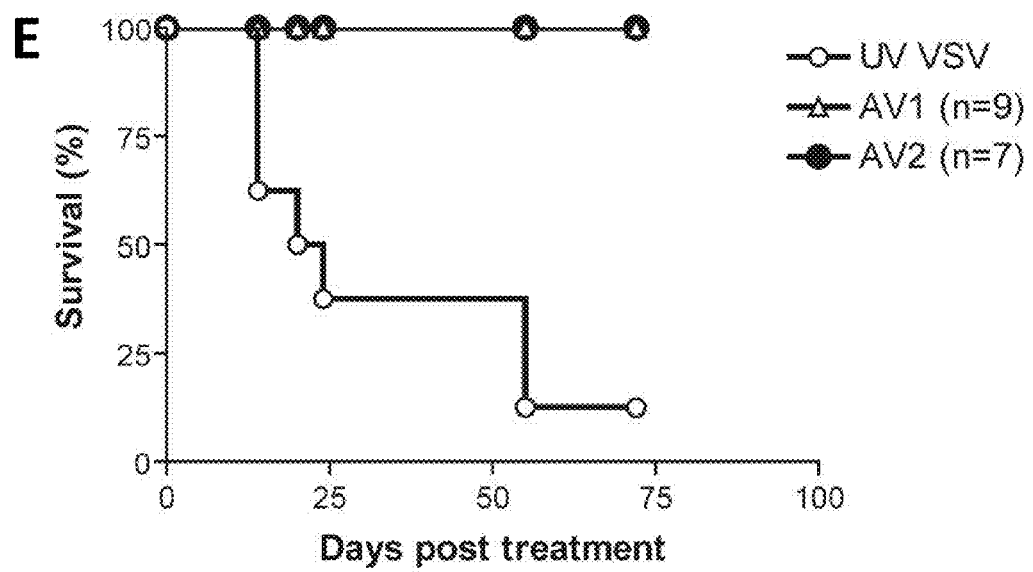
FIGURE 4D-E

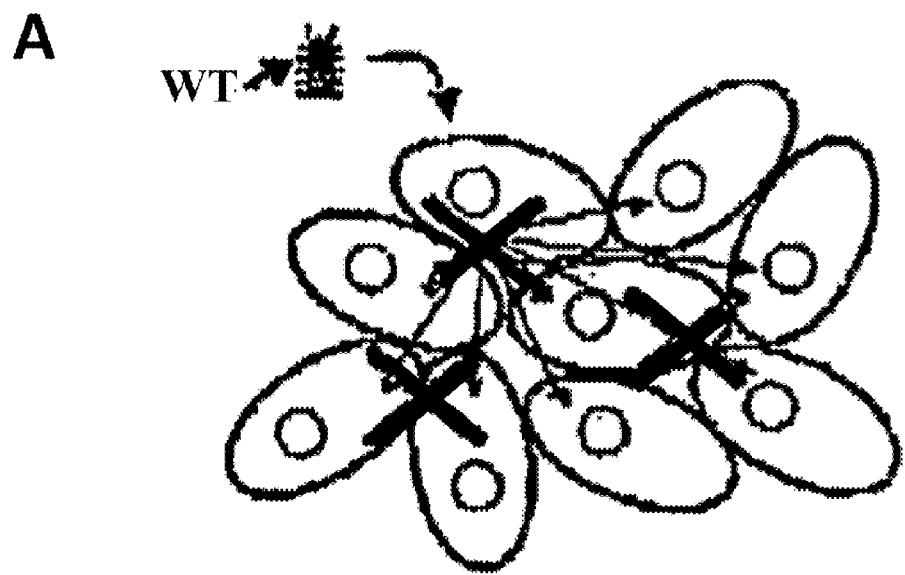
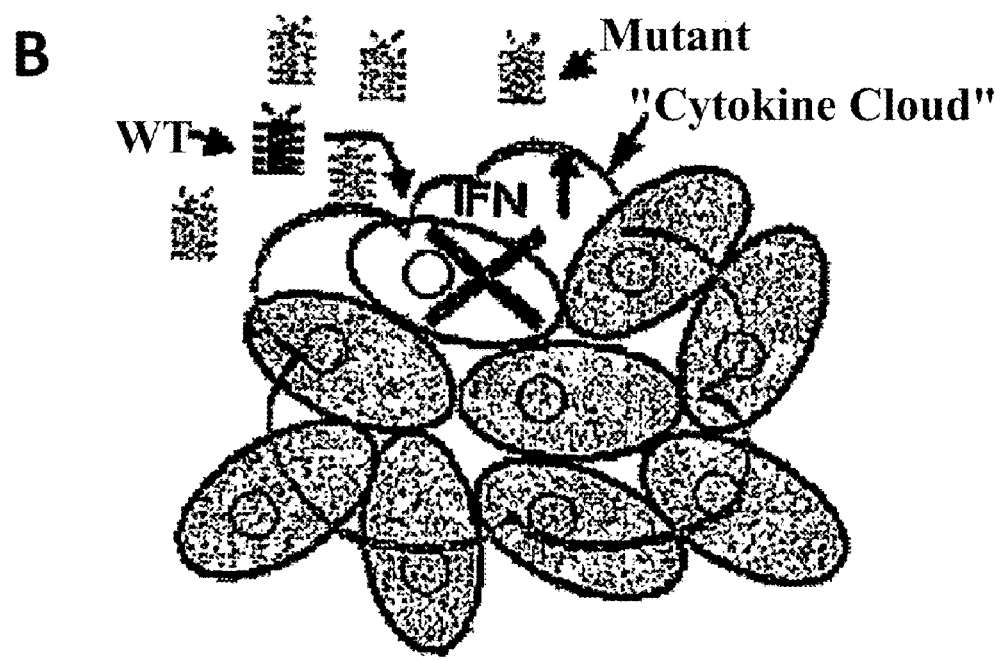
FIGURE 5

FIGURE 9A-H

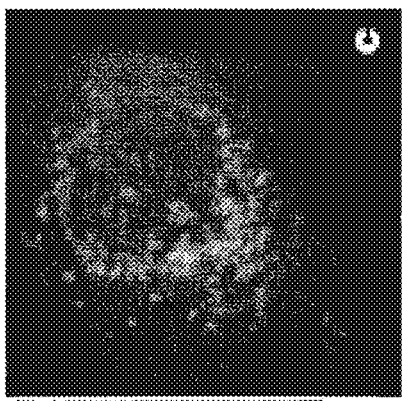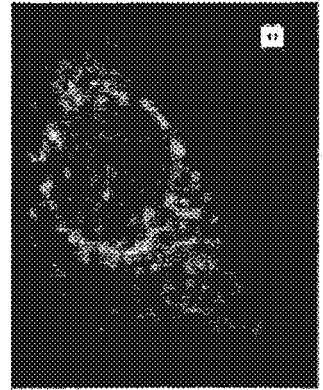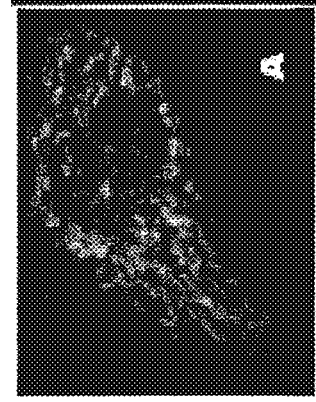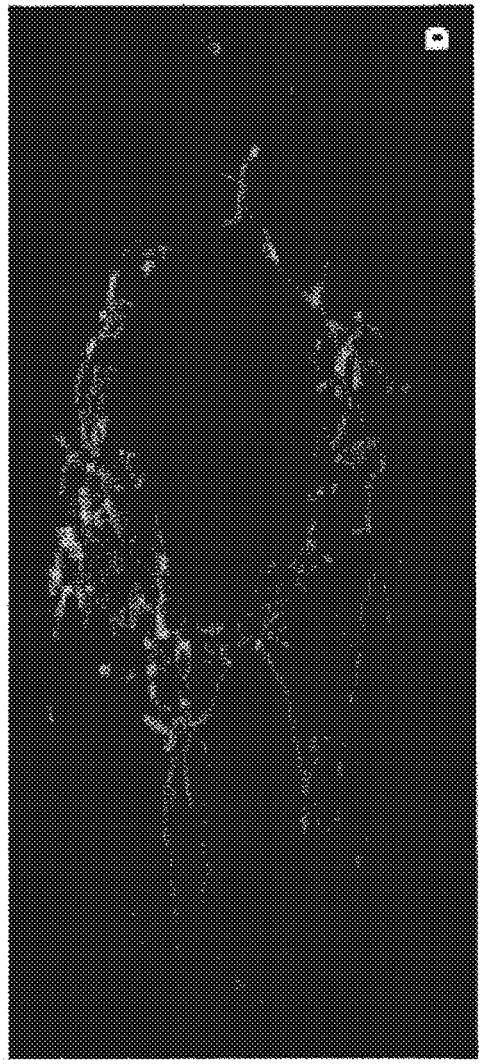
FIGURE 10

*Genome Sequence for VSV Mutant AV1*

ACGAAGACAAACAAACCATTATTATCATTAAAAGGCTCAGGAGAAACTTTAACAGTAATCAAAATGTCTGTT
ACAGTCAAGAGAATCATTGACAACACAGTCATAGTTCCAAAACTTCCTGCAAATGAGGATCCAGTGGAATAC
CCGGCAGATTACTTCAGAAAATCAAAGGAGATTCCTCTTTACATCAATACTACAAAAAGTTTGTCAGATCTA
AGAGGATATGTCTACCAAGGCCTCAAATCCGGAAATGTATCAATCATACATGTCAACAGCTACTTGTATGGA
GCATTGAAGGACATCCGGGGTAAGTTGGATAAAGATTGGTCAAGTTTCGGAATAAACATCGGGAAGGCAGGG
GATACAATCGGAATATTTGACCTTGTATCCTTGAAAGCCCTGGACGGTGTACTTCCAGATGGAGTATCGGAT
GCTTCCAGAACCAGCGCAGATGACAAATGGTTGCCTTTGTATCTACTTGGCTTATACAGAGTGGGCAGAACA
CAAATGCCTGAATACAGAAAAAGGCTCATGGATGGGCTGACAAATCAATGCAAAATGATCAATGAACAGTTT
GAACCTCTTGTGCCAGAAGGTCGTGACATTTTTGATGTGTGGGGAAATGACAGTAATTACACAAAAATTGTC
GCTGCAGTGGACATGTTCTTCCACATGTTCAAAAAACATGAATGTGCCTCGTTCAGATACGAACTATTGTT
TCCAGATTCAAAGATTGTGCTGCATTGGCAACATTTGGACACCTCTGCAAAATAACCGGAATGTCTACAGAA
GATGTAACGACCTGGATCTTGAACCGAGAAGTTGCAGATGAGATGGTCCAAATGATGCTTCCAGGCCAAGAA
ATTGACAAGGCCGATTCATACATGCCTTATTTGATCGACTTTGGATTGTCTTCTAAGTCTCCATATTCTTCC
GTCAAAAACCCTGCCTTCCACTTCTGGGGGCAATTGACAGCTCTTCTGCTCAGATCTACCAGAGCAAGGAAT
GCCCGACAGCCTGATGACATTGAGTATACATCTCTTACTACAGCAGGTTTGTTGTACGCTTATGCAGTAGGA
TCCTCTGCTGACTTGGCACAACAGTTTTGTGTTGGAGATAGCAAATACACTCCAGATGATAGTACCGGAGGA
TTGACGACTAATGCACCGCCACAAGGCAGAGATGTGGTCGAATGGCTCGGATGGTTTGAAGATCAAAACAGA
AAACCGACTCCTGATATGATGCAGTATGCGAAACGAGCAGTCATGTCACTGCAAGGCCTAAGAGAGAAGACA
ATTGGCAAGTATGCTAAGTCAGAATTTGACAAATGACCCTATAATTCTCAGATCACCTATTATATATTATGC
TACATATGAAAAAAACTAACAGATATCATGGATAATCTCACAAAAGTTCGTGAGTATCTCAAGTCCTATTCT
CGTCTAGATCAGGCGGTAGGAGAGATAGATGAGATCGAAGCACAACGAGCTGAAAAGTCCAATTATGAGTTG
TTCCAAGAGGACGGAGTGGAAGAGCATACTAGGCCCTCTTATTTTCAGGCAGCAGATGATTCTGACACAGAA
TCTGAACCAGAAATTGAAGACAATCAAGGCTTGTATGTACCAGATCCGGAAGCTGAGCAAGTTGAAGGCTTT
ATACAGGGGCCTTTAGATGACTATGCGGATGAGGACGTGGATGTTGTATTCACTTCGGACTGGAAACAGCCT
GAGCTTGAATCCGACGAGCATGGAAAGACCTTACGGTTGACATTGCCAGAGGGTTTAAGTGGAGAGCAGAAA
TCCCAGTGGCTTTTGACGATTAAAGCAGTCGTTCAAAGTGCCAAACACTGGAATCTGGCAGAGTGCACATTT
GAAGCATCGGGAGAAGGGGTCATCATAAAAAAGCGCCAGATAACTCCGGATGTATATAAGGTCACTCCAGTG
ATGAACACACATCCGTCCCAATCAGAAGCCGTATCAGATGTTTGGTCTCTCTCAAAGACATCCATGACTTTC
CAACCCAAGAAAGCAAGTCTTCAGCCTCTCACCATATCCTTGGATGAATTGTTCTCATCTAGAGGAGAATTC
ATCTCTGTCGGAGGTAACGGACGAATGTCTCATAAAGAGGCCATCCTGCTCGGTCTGAGGTACAAAAAGTTG
TACAATCAGGCGAGAGTCAAATATTCTCTGTAGACTATGAAAAAAAGTAACAGATATCACAATCTAAGTGTT
ATCCCAATCCATTCATCATGAGTTCCTTAAAGAAGATTCTCGGTCTGAAGGGGAAAGGTAAGAAATCTAAGA
AATTAGGGATCGCACCACCCCCTTATGAAGAGGACACTAACATGGAGTATGCTCCGAGCGCTCCAATTGACA
AATCCTATTTTGGAGTTGACGAGAGGGACACTCATGATCCGCATCAATTAAGATATGAGAAATTCTTCTTTA
CAGTGAAAATGACGGTTAGATCTAATCGTCCGTTCAGAACATACTCAGATGTGGCAGCCGCTGTATCCCATT

FIGURE 11

```
GGGATCACATGTACATCGGAATGGCAGGGAAACGTCCCTTCTACAAGATCTTGGCTTTTTTGGGTTCTTCTA
ATCTAAAGGCCACTCCAGCGGTATTGGCAGATCAAGGTCAACCAGAGTATCACGCTCACTGTGAAGGCAGGG
CTTATTTGCCACACAGAATGGGGAAGACCCCTCCCATGCTCAATGTACCAGAGCACTTCAGAAGACCATTCA
ATATAGGTCTTTACAAGGGAACGGTTGAGCTCACAATGACCATCTACGATGATGAGTCACTGGAAGCAGCTC
CTATGATCTGGGATCATTTCAATTCTTCCAAATTTTCTGATTTCAGAGAGAAGGCCTTAATGTTTGGCCTGA
TTGTCGAGAAAAAGGCATCTGGAGCTTGGGTCCTGGATTCTGTCAGCCACTTCAAATGAGCTAGTCTAGCTT
CCAGCTTCTGAACAATCCCCGGTTTACTCAGTCTCTCCTAATTCCAGCCTTTCGAACAACTAATATCCTGTC
TTTTCTATCCCTATGAAAAAAACTAACAGAGATCGATCTGTTTCCTTGACACCATGAAGTGCCTTTTGTACT
TAGCTTTTTTATTCATCGGGGTGAATTGCAAGTTCACCATAGTTTTTCCATACAACCGAAAAGGAAACTGGA
AAAATGTTCCTTCCAATTACCATTATTGCCCGTCAAGCTCAGATTTAAATTGGCATAATGACTTAATAGGCA
CAGCCTTACAAGTCAAAATGCCCAAGAGTCACAAGGCTATTCAAGCAGACGGTTGGATGTGTCATGCTTCCA
AATGGGTCACTACTTGTGATTTCCGCTGGTACGGACCGAAGTATATAACACATTCCATCCGATCCTTCACTC
CATCTGTAGAACAATGCAAGGAAAGCATTGAACAAACGAAACAAGGAACTTGGCTGAATCCAGGCTTCCCTC
CTCAAAGTTGTGGATATGCAACTGTGACGGATGCTGAAGCAGCGATTGTCCAGGTGACTCCTCACCATGTGC
TTGTTGATGAATACACAGGAGAATGGGTTGATTCACAGTTCATCAACGGAAAATGCAGCAATGACATATGCC
CCACTGTCCATAACTCCACAACCTGGCATTCCGACTATAAGGTCAAAGGGCTATGTGATTCTAACCTCATTT
CCATGGACATCACCTTCTTCTCAGAGGACGGAGAGCTATCATCCCTAGGAAAGGAGGGCACAGGGTTCAGAA
GTAACTACTTTGCTTATGAAACTGGAGACAAGGCCTGCAAAATGCAGTACTGCAAGCATTGGGGAGTCAGAC
TCCCATCAGGTGTCTGGTTCGAGATGGCTGATAAGGATCTCTTTGCTGCAGCCAGATTCCCTGAATGCCCAG
AAGGGTCAAGTATCTCTGCTCCATCTCAGACCTCAGTGGATGTAAGTCTCATTCAGGACGTTGAGAGGATCT
TGGATTATTCCCTCTGCCAAGAAACCTGGAGCAAAATCAGAGCGGGTCTTCCCATCTCTCCAGTGGATCTCA
GCTATCTTGCTCCTAAAAACCCAGGAACCGGTCCTGTCTTTACCATAATCAATGGTACCCTAAAATACTTTG
AGACCAGATACATCAGAGTCGATATTGCTGCTCCAATCCTCTCAAGAATGGTCGGAATGATCAGTGGAACTA
CCACAGAAAGGGAACTGTGGGATGACTGGGCTCCATATGAAGACGTGGAAATTGGACCCAATGGAGTTCTGA
GGACCAGTTCAGGATATAAGTTTCCTTTATATATGATTGGACATGGTATGTTGGACTCCGATCTTCATCTTA
GCTCAAAGGCTCAGGTGTTTGAACATCCTCACATTCAAGACGCTGCTTCGCAGCTTCCTGATGATGAGACTT
TATTTTTTGGTGATACTGGGCTATCCAAAAATCCAATCGAGTTTGTAGAAGGTTGGTTCAGTAGTTGGAAGA
GCTCTATTGCCTCTTTTTTCTTTATCATAGGGTTAATCATTGGACTATTCTTGGTTCTCCGAGTTGGTATTT
ATCTTTGCATTAAATTAAAGCACACCAAGAAAAGACAGATTTATACAGACATAGAGATGAACCGACTTGGGA
AGTAACTCAAATCCTGCACAACAGATTCTTCATGTTTGAACCAAATCAACTTGTGATATCATGCTCAAAGAG
GCCTTAATTATATTTTAATTTTTAATTTTTATGAAAAAACTAACAGCAATCATGGAAGTCCACGATTTTGA
GACCGACGAGTTCAATGATTTCAATGAAGATGACTATGCCACAAGAGAATTCCTGAATCCCGATGAGCGCAT
GACGTACTTGAATCATGCTGATTACAATTTGAATTCTCCTCTAATTAGTGATGATATTGACAATTTGATCAG
GAAATTCAATTCTCTTCCGATTCCCTCGATGTGGGATAGTAAGAACTGGGATGGAGTTCTTGAGATGTTAAC
ATCATGTCAAGCCAATCCCATCTCAACATCTCAGATGCATAAATGGATGGGAAGTTGGTTAATGTCTGATAA
TCATGATGCCAGTCAAGGGTATAGTTTTTTACATGAAGTGGACAAAGAGGCAGAAATAACATTTGACGTGGT
```

FIGURE 11 continued

```
GGAGACCTTCATCCGCGGCTGGGGCAACAAACCAATTGAATACATCAAAAAGGAAAGATGGACTGACTCATT
CAAAATTCTCGCTTATTTGTGTCAAAAGTTTTTGGACTTACACAAGTTGACATTAATCTTAAATGCTGTCTC
TGAGGTGGAATTGCTCAACTTGGCGAGGACTTTCAAAGGCAAAGTCAGAAGAAGTTCTCATGGAACGAACAT
ATGCAGGCTTAGGGTTCCCAGCTTGGGTCCTACTTTTATTTCAGAAGGATGGGCTTACTTCAAGAAACTTGA
TATTCTAATGGACCGAAACTTTCTGTTAATGGTCAAAGATGTGATTATAGGGAGGATGCAAACGGTGCTATC
CATGGTATGTAGAATAGACAACCTGTTCTCAGAGCAAGACATCTTCTCCCTTCTAAATATCTACAGAATTGG
AGATAAAATTGTGGAGAGGCAGGGAAATTTTTCTTATGACTTGATTAAAATGGTGGAACCGATATGCAACTT
GAGGCTGATGAAATTAGCAAGAGAATCAAGGCCTTTAGTCCCACAATTCCCTCATTTTGAAAATCATATCAA
GACTTCTGTTGATGAAGGGGCAAAAATTGACCGAGGTATAAGATTCCTCCATGATCAGATAATGAGTGTGAA
AACAGTGGATCTCACACTGGTGATTTATGGATCGTTCAGACATTGGGGTCATCCTTTTATAGATTATTACGC
TGGACTAGAAAAATTACATTCCCAAGTAACCATGAAGAAAGATATTGATGTGTCATATGCAAAAGCACTTGC
AAGTGATTTAGCTCGGATTGTTCTATTTCAACAGTTCAATGATCATAAAAAGTGGTTCGTGAATGGAGACTT
GCTCCCTCATGATCATCCCTTTAAAAGTCATGTTAAAGAAAATACATGGCCCACAGCTGCTCAAGTTCAAGA
TTTTGGAGATAAATGGCATGAACTTCCGCTGATTAAATGTTTTGAAATACCCGACTTACTAGACCCATCGAT
AATATACTCTGACAAAAGTCATTCAATGAATAGGTCAGAGGTGTTGAAACATGTCCGAATGAATCCGAACAC
TCCTATCCCTAGTAAAAAGGTGTTGCAGACTATGTTGGACACAAAGGCTACCAATTGGAAAGAATTTCTTAA
AGAGATTGATGAGAAGGGCTTAGATGATGATGATCTAATTATTGGtCTTAAAGGAAAGGAGAGGGAACTGAA
GTTGGCAGGTAGATTTTTCTCCCTAATGTCTTGGAAATTGCGAGAATACTTTGTAATTACCGAATATTTGAT
AAAGACTCATTTCGTCCCTATGTTTAAAGGCCTGACAATGGCGGACGATCTAACTGCAGTCATTAAAAAGAT
GTtAGATTCCTCATCCGGCCAAGGATTGAAGTCATATGAGGCAATTTGCATAGCCAATCACATTGATTACGA
AAAATGGAATAACCACCAAAGGAAGTTATCAAACGGCCCAGTGTTCCGAGTTATGGGCCAGTTCTTAGGTTA
TCCATCCTTAATCGAGAGAACTCATGAATTTTTTGAGAAAAGTCTTATATACTACAATGGAAGACCAGACTT
GATGCGTGTTCACAACAACACACTGATCAATTCAACCTCCCAACGAGTTTGTTGGCAAGGACAAGAGGGTGG
ACTGGAAGGTCTACGGCAAAAAGGATGGAGTATCCTCAATCTACTGGTTATTCAAAGAGAGGCTAAAATCAG
AAACACTGCTGTCAAAGTCTTGGCACAAGGTGATAATCAAGTTATTTGCACACAGTATAAAACGAAGAAATC
GAGAAACGTTGTAGAATTACAGGGTGCTCTCAATCAAATGGTTTCTAATAATGAGAAAATTATGACTGCAAT
CAAAATAGGGACAGGGAAGTTAGGACTTTTGATAAATGACGATGAGACTATGCAATCTGCAGATTACTTGAA
TTATGGAAAAATACCGATTTTCCGTGGAGTGATTAGAGGGTTAGAgCCAAGAGATGGTCACGAGTGACTTG
TGTCACCAATGACCAAATACCCACTTGTGCTAATATAATGAGCTCAGTTTCCACAAATGCTCTCACCGTAGC
TCATTTTGCTGAGAACCCAATCAATGCCATGATACAGTACAATTATTTTGGGACATTTGCTAGACTCTTGTT
GATGATGCATGATCCTGCTCTTCGTCAATCATTGTATGAAGTTCAAGATAAGATACCGGGCTTGCACAGTTC
TACTTTCAAATACGCCATGTTGTATTTGGACCCTTCCATTGGAGGAGTGTCGGGCATGTCTTTGTCCAGGTT
TTTGATTAGAGCCTTCCCAGATCCCGTAACAGAAAGTCTCTCATTCTGGAGATTCATCCATGTaCATGCTCG
AAGTGAGCATCTGAAGGAGATGAGTGCAGTATTTGGAAACCCCGAGATAGCCAAGTTTCGAATAACTCACAT
AGACAAGCTAGTAGAAGATCCAACCTCTCTGAACATCGCTATGGGAATGAGTCCAGCGAACTTGTTAAAGAC
TGAGGTTAAAAAATGCTTAATCGAATCAAGACAAACCATCAGGAACCAGGTGATTAAGGATGCAACCATATA
```

FIGURE 11 continued

```
TTTGTATCATGAAGAGGATCGGCTCAGAAGTTTCTTATGGTCAATAAATCCTCTGTTCCCTAGATTTTTAAG
TGAATTCAAATCAGGCACTTTTTTGGGAGTCGCAGACGGGCTCATCAGTCTATTTCAAAATTCTCGTACTAT
TCGGAACTCCTTTAAGAAAAAGTATCATAGGGAATTGGATGATTTGATTGTGAGGAGTGAGGTATCCTCTTT
GACACATTTAGGGAAACTTCATTTGAGAAGGGGATCATGTAAAATGTGGACATGTTCAGCTACTCATGCTGA
CACATTAAGATACAAATCCTGGGGCCGTACAGTTATTGGGACAACTGTACCCCATCCATTAGAAATGTTGGG
TCCACAACATCGAAAAGAGACTCCTTGTGCACCATGTAACACATCAGGGTTCAATTATGTTTCTGTGCATTG
TCCAGACGGGATCCATGACGTCTTTAGTTCACGGGACCATTGCCTGCTTATCTAGGGTCTAAAACATCTGA
ATCTACATCTATTTTGCAGCCTTGGGAAAGGGAAAGCAAAGTCCCACTGATTAAAAGAGCTACACGTCTTAG
AGATGCTATCTCTTGGTTTGTTGAACCCGACTCTAAACTAGCAATGACTATACTTTCTAACATCCACTCTTT
AACAGGCGAAGAATGGACCAAAAGGCAGCATGGGTTCAAAAGAACAGGGTCTGCCCTTCATAGGTTTTCGAC
ATCTCGGATGAGCCATGGTGGGTTCGCATCTCAGAGCACTGCAGCATTGACCAGGTTGATGGCAACTACAGA
CACCATGAGGGATCTGGGAGATCAGAaTTTCGACTTTTTATTCCAGGCAACGTTGCTCTATGCTCAGATTAC
CACCACTGTTGCAAGAGACGGATGGATCACCAGTTGTACAGATCATTATCATATTGCCTGTAAGTCCTGTTT
GAGACCCATAGAAGAGATCACCCTGGACTCAAGTATGGACTACACGCCCCAGATGTATCCCATGTGCTGAA
GACATGGAGGAATGGGGAAGGTTCGTGGGGACAAGAGATAAAACAGATCTATCCTTTAGAAGGGAATTGGAA
GAATTTAGCACCTGCTGAGCAATCCTATCAAGTCGGCAGATGTATAGGTTTTCTATATGGAGACTTGGCGTA
TAGAAAATCTACTCATGCCGAGGACAGTTCTCTATTTCCTCTATCTATACAAGGTCGTATTAGAGGTCGAGG
TTTCTTAAAAGGGTTGCTAGACGGATTAATGAGAGCAAGTTGCTGCCAAGTAATACACCGGAGAAGTCTGGC
TCATTTGAAGAGGCCGGCCAACGCAGTGTACGGAGGTTTGATTTACTTGATTGATAAATTGAGTGTATCACC
TCCATTCCTTTCTCTTACTAGATCAGGACCTATTAGAGACGAATTAGAAACGATTCCCCACAAGATCCCAAC
CTCCTATCCGACAAGCAACCGTGATATGGGGGTGATTGTCAGAAATTACTTCAAATACCAATGCCGTCTAAT
TGAAAAGGGAAAATACAGATCACATTATTCACAATTATGGTTATTCTCAGATGTCTTATCCATAGACTTCAT
TGGACCATTCTCTATTTCCACCACCCTCTTGCAAATCCTATACAAGCCATTTTTATCTGGGAAAGATAAGAA
TGAGTTGAGAGAGCTGGCAAATCTTTCTTCATTGCTAAGATCAGGAGAGGGGTGGGAAGACATACATGTAAA
ATTCTTCACCAAGGACATATTATTGTGTCCAGAGGAAATCAGACATGCTTGCAAGTTCGGGATTGCTAAGGA
TAATAATAAAGACATGAGCTATCCCCCTTGGGGAAGGGAATCCAGAGGGACAATTACAACAATCCCTGTTTA
TTATACGACCACCCCTTACCCAAAGATGCTAGAGATGCCTCCAAGAATCCAAAATCCCCTGCTGTCCGGAAT
CAGGTTGGGCCAGTTACCAACTGGCGCTCATTATAAAATTCGGAGTATATTACATGGAATGGGAATCCATTA
CAGGGACTTCTTGAGTTGTGGAGACGGCTCCGGAGGGATGACTGCTGCATTACTACGAGAAATGTGCATAG
CAGAGGAATATTCAATAGTCTGTTAGAATTATCAGGGTCAGTCATGCGAGGCGCCTCTCCTGAGCCCCCCAG
TGCCCTAGAAACTTTAGGAGGAGATAAATCGAGATGTGTAAATGGTGAAACATGTTGGGAATATCCATCTGA
CTTATGTGACCCAAGGACTTGGACTATTTCCTCCGACTCAAAGCAGGCTTGGGGCTTCAAATTGATTTAAT
TGTAATGGATATGGAAGTTCGGGATTCTTCTACTAGCCTGAAAATTGAGACGAATGTTAGAAATTATGTGCA
CCGGATTTTGGATGAGCAAGGAGTTTTAATCTACAAGACTTATGGAACATATATTTGTGAGAGCGAAAAGAA
TGCAGTAACAATCCTTGGTCCCATGTTCAAGACGGTCGACTTAGTTCAAACAGAATTTAGTAGTTCTCAAAC
GTCTGAAGTATATATGGTATGTAAAGGTTTGAAGAAATTAATCGATGAACCCAATCCCGATTGGTCTTCCAT
```

FIGURE 11 continued

```
CAATGAATCCTGGAAAAACCTGTACGCATTCCAGTCATCAGAACAGGAATTTGCCAGAGCAAAGAAGGTTAG
TACATACTTTACCTTGACAGGTATTCCCTCCCAATTCATTCCTGATCCTTTTGTAAACATTGAGACTATGCT
ACAAATATTCGGAGTACCCACGGGTGTGTCTCATGCGGCTGCCTTAAAATCATCTGATAGACCTGCAGATTT
ATTGACCATTAGCCTTTTTTATATGGCGATTATATCGTATTATAACATCAATCATATCAGAGTAGGACCGAT
ACCTCCGAACCCCCCATCAGATGGAATTGCACAAAATGTGGGGATCGCTATAACTGGTATAAGCTTTTGGCT
GAGTTTGATGGAGAAAGACATTCCACTATATCAACAGTGTTTAGCAGTTATCCAGCAATCATTCCCGATTAG
GTGGGAGGCTGTTTCAGTAAAAGGAGGATACAAGCAGAAGTGGAGTACTAGAGGTGATGGGCTCCCAAAAGA
TACCCGAATTTCAGACTCCTTGGCCCCAATCGGGAACTGGATCAGATCTCTGGAATTGGTCCGAAACCAAGT
TCGTCTGAATCCATTCAATGAGATCTTGTTCAATCAGCTATGTCGTACAGTGGATAATCATTTGAAATGGTC
AAATTTGCGAAAAAACACAGGAATGATTGAATGGATCAATAGACGAATTTCAAAAGAAGACCGGTCTATACT
GATGTTGAAGAGTGACCTACATGAGGAAAACTCTTGGAGAGATTAAAAAATCATGAGGAGACTCCAAACTTT
AAGTATGAAAAAAACTTTGATCCTTAAGACCCTCTTGTGGTTTTTATTTTTTATCTGGTTTTGTGGTCTTCG
T
```

FIGURE 11 continued

*Nucleic Acid Sequence of the M Protein Gene for VSV Mutant AV1*

ATGAGTTCCTTAAAGAAGATTCTCGGTCTGAAGGGGAAAGGTAAGAAATCTAAGAAATTAGGGATCGCACCA
CCCCCTTATGAAGAGGACACTAACATGGAGTATGCTCCGAGCGCTCCAATTGACAAATCCTATTTTGGAGTT
GACGAGATGGACACTCATGATCCGCATCAATTAAGATATGAGAAATTCTTCTTTACAGTGAAAATGACGGTT
AGATCTAATCGTCCGTTCAGAACATACTCAGATGTGGCAGCCGCTGTATCCCATTGGGATCACATGTACATC
GGAATGGCAGGGAAACGTCCCTTCTACAAGATCTTGGCTTTTTTGGGTTCTTCTAATCTAAAGGCCACTCCA
GCGGTATTGGCAGATCAAGGTCAACCAGAGTATCACGCTCACTGTGAAGGCAGGGCTTATTTGCCACACAGA
ATGGGGAAGACCCCTCCCATGCTCAATGTACCAGAGCACTTCAGAAGACCATTCAATATAGGTCTTTACAAG
GGAACGGTTGAGCTCACAATGACCATCTACGATGATGAGTCACTGGAAGCAGCTCCTATGATCTGGGATCAT
TTCAATTCTTCCAAATTTTCTGATTTCAGAGAGAAGGCCTTAATGTTTGGCCTGATTGTCGAGAAAAAGGCA
TCTGGAGCTTGGTTCCTGGATTCTGTCAGACACTTCAAATGA

FIGURE 12

*Amino Acid Sequence for the M Protein of VSV Mutant AV1*

MSSLKKILGLKGKGKKSKKLGIAPPPYEEDTNMEYAPSAPIDKSYFGVDERDTHDPHQLRYEKFFFTVKMTV
RSNRPFRTYSDVAAAVSHWDHMYIGMAGKRPFYKILAFLGSSNLKATPAVLADQGQPEYHAHCEGRAYLPHR
MGKTPPMLNVPEHFRRPFNIGLYKGTVELTMTIYDDESLEAAPMIWDHFNSSKFSDFREKALMFGLIVEKKA
SGAWVLDSVSHFK.

FIGURE 13

*Genome sequence for VSV Mutant AV2*

ACGAAGACAAACAAACCATTATTATCATTAAAAGGCTCAGGAGAAACTTTAACAGTAATCAAAATGTCTGTT
ACAGTCAAGAGAATCATTGACAACACAGTCATAGTTCCAAAACTTCCTGCAAATGAGGATCCAGTGGAATAC
CCGGCAGATTACTTCAGAAAATCAAAGGAGATTCCTCTTTACATCAATACTACAAAAAGTTTGTCAGATCTA
AGAGGATATGTCTACCAAGGCCTCAAATCCGGAAATGTATCAATCATACATGTCAACAGCTACTTGTATGGA
GCATTGAAGGACATCCGGGGTAAGTTGGATAAAGATTGGTCAAGTTTCGGAATAAACATCGGGAAGGCAGGG
GATACAATCGGAATATTTGACCTTGTATCCTTGAAAGCCCTGGACGGTGTACTTCCAGATGGAGTATCGGAT
GCTTCCAGAACCAGCGCAGATGACAAATGGTTGCCTTTGTATCTACTTGGCTTATACAGAGTGGGCAGAACA
CAAATGCCTGAATACAGAAAAAGGCTCATGGATGGGCTGACAAATCAATGCAAAATGATCAATGAACAGTTT
GAACCTCTTGTGCCAGAAGGTCGTGACATTTTTGATGTGTGGGGAAATGACAGTAATTACACAAAAATTGTC
GCTGCAGTGGACATGTTCTTCCACATGTTCAAAAAACATGAATGTGCCTCGTTCAGATACGGAACTATTGTT
TCCAGATTCAAAGATTGTGCTGCATTGGCAACATTTGGACACCTCTGCAAAATAACCGGAATGTCTACAGAA
GATGTAACGACCTGGATCTTGAACCGAGAAGTTGCAGATGAGATGGTCCAAATGATGCTTCCAGGCCAAGAA
ATTGACAAGGCCGATTCATACATGCCTTATTTGATCGACTTTGGATTGTCTTCTAAGTCTCCATATTCTTCC
GTCAAAAACCCTGCCTTCCACTTCTGGGGGCAATTGACAGCTCTTCTGCTCAGATCCACCAGAGCAAGGAAT
GCCCGACAGCCTGATGACATTGAGTATACATCTCTTACTACAGCAGGTTTGTTGTACGCTTATGCAGTAGGA
TCCTCTGCTGACTTGGCACAACAGTTTTGTGTTGGAGATAGCAAATACACTCCAGATGATAGTACCGGAGGA
TTGACGACTAATGCACCGCCACAAGGCAGAGATGTGGTCGAATGGCTCGGATGGTTTGAAGATCAAAACAGA
AAACCGACTCCTGATATGATGCAGTATGCGAAACGAGCAGTCATGTCACTGCAAGGCCTAAGAGAGAAGACA
ATTGGCAAGTATGCTAAGTCAGAATTTGACAAATGACCCTATAATTCTCAGATCACCTATTATATATTATGC
TACATATGAAAAAAACTAACAGATATCATGGATAATCTCACAAAAGTTCGTGAGTATCTCAAGTCCTATTCT
CGTCTAGATCAGGCGGTAGGAGAGATAGATGAGATCGAAGCACAACGAGCTGAAAAGTCCAATTATGAGTTG
TTCCAAGAGGACGGAGTGGAAGAGCATACTAGGCCCTCTTATTTTCAGGCAGCAGATGATTCTGACACAGAA
TCTGAACCAGAAATTGAAGACAATCAAGGCTTGTATGTACCAGATCCGGAAGCTGAGCAAGTTGAAGGCTTT
ATACAGGGGCCTTTAGATGACTATGCGGATGAGGACGTGGATGTTGTATTCACTTCGGACTGGAAACAGCCT
GAGCTTGAATCCGACGAGCATGGAAAGACCTTACGGTTGACATTGCCAGAGGGTTTAAGTGGAGAGCAGAAA
TCCCAGTGGCTTTTGACGATTAAAGCAGTCGTTCAAAGTGCCAAACACTGGAATCTGGCAGAGTGCACATTT
GAAGCATCGGGAGAAGGGGTCATCATAAAAAAGCGCCAGATAACTCCGGATGTATATAAGGTCACTCCAGTG
ATGAACACACATCCGTCCCAATCGGAAGCCGTATCAGATGTTTGGTCTCTCTCAAAGACATCCATGACTTTC
CAACCCAAGAAAGCAAGTCTTCAGCCTCTCACCATATCCTTGGATGAATTGTTCTCATCTAGAGGAGAATTC
ATCTCTGTCGGAGGTAACGGACGAATGTCTCATAAAGAGGCCATCCTGCTCGGTCTGAGGTACAAAAAGTTG
TACAATCAGGCGAGAGTCAAATATTCTCTGTAGACTATGAAAAAAAGTAACAGATATCACAATCTAAGTGTT
ATCCCAATCCATTCATCATGAGTTCCTTAAAGAAGATTCTCGGTCTGAAGGGGAAAGGTAAGAAATCTAAGA
AATTAGGGATCGCACCACCCCCTTATGAAGAGGACACTAACATGGAGTATGCTCCGAGCGCTCCAATTGACA
AATCCTATTTTGGAGTTGACGAGATGGACACTCATGATCCGCATCAATTAAGATATGAGAAATTCTTCTTTA
CAGTGAAAATGACGGTTAGATCTAATCGTCCGTTCAGAACATACTCAGATGTGGCAGCCGCTGTATCCCATT

Figure 14

```
GGGATCACATGTACATCGGAATGGCAGGGAAACGTCCCTTCTACAAGATCTTGGCTTTTTTGGGTTCTTCTA
ATCTAAAGGCCACTCCAGCGGTATTGGCAGATCAAGGTCAACCAGAGTATCACGCTCACTGTGAAGGCAGGG
CTTATTTGCCACACAGAATGGGGAAGACCCCTCCCATGCTCAATGTACCAGAGCACTTCAGAAGACCATTCA
ATATAGGTCTTTACAAGGGAACGGTTGAGCTCACAATGACCATCTACGATGATGAGTCACTGGAAGCAGCTC
CTATGATCTGGGATCATTTCAATTCTTCCAAATTTTCTGATTTCAGAGAGAAGGCCTTAATGTTTGGCCTGA
TTGTCGAGAAAAAGGCATCTGGAGCTTGGTTCCTGGATTCTGTCAGACACTTCAAATGAGCTAGTCTAGCTT
CCAGCTTCTGAACAATCCCCGGTTTACTCAGTCTCTCCTAATTCCAGCCTTTCGAACAACTAATATCCTGTC
TTTTCTATCCCTATGAAAAAACTAACAGAGATCGATCTGTTTCCTTGACACCATGAAGTGCCTTTTGTACT
TAGCTTTTTTATTCATCGGGGTGAATTGCAAGTTCACCATAGTTTTTCCATACAACCAAAAAGGAAACTGGA
AAAATGTTCCTTCCAATTACCATTATTGCCCGTCAAGCTCAGATTTAAATTGGCATAATGACTTAATAGGCA
CAGCCTTACAAGTCAAAATGCCCAAGAGTCACAAGGCTATTCAAGCAGACGGTTGGATGTGTCATGCTTCCA
AATGGGTCACTACTTGTGATTTCCGCTGGTACGGACCGAAGTATATAACACATTCCATCCGATCCTTCACTC
CATCTGTAGAACAATGCAAGGAAAGCATTGAACAAACGAAACAAGGAACTTGGCTGAATCCAGGCTTCCCTC
CTCAAAGTTGTGGATATGCAACTGTGACGGATGCTGAAGCAGCGATTGTCCAGGTGACTCCTCACCATGTGC
TTGTTGATGAATACACAGGAGAATGGGTTGATTCACAGTTCATCAACGGAAAATGCAGCAATGACATATGCC
CCACTGTCCATAACTCCACAACCTGGCATTCCGACTATAAGGTCAAAGGGCTATGTGATTCTAACCTCATTT
CCATGGACATCACCTTCTTCTCAGAGGACGGAGAGCTATCATCCCTAGGAAAGGAGGGCACAGGGTTCAGAA
GTAACTACTTTGCTTATGAAACTGGAGACAAGGCCTGCAAAATGCAGTACTGCAAGCGTTGGGGAGTCAGAC
TCCCATCAGGTGTATGGTTCGAGATGGCTGATAAGGATCTCTTTGCTGCAGCCAGATTCCCTGAATGCCCAG
AAGGGTCAAGTATCTCTGCTCCATCTCAGACCTCAGTGGATGTAAGTCTCATTCAGGACGTTGAGAGGATCT
TGGATTATTCCCTCTGCCAAGAAACCTGGAGCAAAATCAGAGCGGGTCTTCCCATCTCTCCAGTGGATCTCA
GCTATCTTGCTCCTAAAAACCCAGGAACCGGTCCTGTCTTTACCATAATCAATGGTACCCTAAAATACTTTG
AGACCAGATACATCAGAGTCGATATTGCTGCTCCAATCCTCTCAAGAATGGTCGGAATGATCAGTGGAACTA
CCACAGAAAGGGAACTGTGGGATGACTGGGCTCCATATGAAGACGTGGAAATTGGACCCAATGGAGTTCTGA
GGACCAGTTCAGGATATAAGTTTCCTTTATATATGATTGGACATGGTATGTTGGACTCCGATCTTCATCTTA
GCTCAAAGGCTCAGGTGTTTGAACATCCTCACATTCAAGACGCTGCTGCGCAGCTTCCTGATGATGAGACTT
TATTTTTGGTGATACTGGGCTATCCAAAAATCCAATCGAGTTTGTAGAAGGTTGGTTCAGTAGTTGGAAGA
GCTCTATTGCCTCTTTTTTCTTTATCATAGGGTTAATCATTGGACTATTCTTGGTTCTCCGAGTTGGTATTT
ATCTTTGCATTAAATTAAAGCACACCAAGAAAAGACAGATTTATACAGACATAGAGATGAACCGACTTGGGA
AGTAACTCAAATCCTGCACAACAGATTCTTCATGTTTGAACCAAATCAACTTGTGATATCATGCTCAAAGAG
GCCTTAATTATATTTTAATTTTTAATTTTTATGAAAAAAACTAACAGCAATCATGGAAGTCCACGATTTTGA
GACCGACGAGTTCAATGATTTCAATGAAGATGACTATGCCACAAGAGAATTCCTGAATCCCGATGAGCGCAT
GACGTACTTGAATCATGCTGATTACAATTTGAATTCTCCTCTAATTAGTGATGATATTGACAATTTGATCAG
GAAATTCAATTCTCTTCCGATTCCCTCGATGTGGGATAGTAAGAACTGGGATGGAGTTCTTGAGATGTTAAC
ATCATGTCAAGCCAATCCCATCTCAACATCTCAGATGCATAAATGGATGGGAAGTTGGTTAATGTCTGATAA
TCATGATGCCAGTCAAGGGTATAGTTTTTTACATGAAGTGGACAAAGAGGCAGAAATAACATTTGACGTGGT
```

Figure 14 continued

```
GGAGACCTTCATCCGCGGCTGGGGCAACAAACCAATTGAATACATCAAAAAGGAAAGATGGACTGACTCATT
CAAAATTCTCGCTTATTTGTGTCAAAAGTTTTTGGACTTACACAAGTTGACATTAATCTTAAATGCTGTCTC
TGAGGTGGAATTGCTCAACTTGGCGAGGACTTTCAAAGGCAAAGTCAGAAGAAGTTCTCATGGAACGAACAT
ATGCAGGCTTAGGGTTCCCAGCTTGGGTCCTACTTTTATTTCAGAAGGATGGGCTTACTTCAAGAAACTTGA
TATTCTAATGGACCGAAACTTTCTGTTAATGGTCAAAGATGTGATTATAGGGAGGATGCAAACGGTGCTATC
CATGGTATGTAGAATAGACAACCTGTTCTCAGAGCAAGACATCTTCTCCCTTCTAAATATCTACAGAATTGG
AGATAAAATTGTGGAGAGGCAGGGAAATTTTTCTTATGACTTGATTAAAATGGTGGAACCGATATGCAACTT
GAAGCTGATGAAATTAGCAAGAGAATCAAGGCCTTTAGTCCCACAATTCCCTCATTTTGAAAATCATATCAA
GACTTCTGTTGATGAAGGGGCAAAAATTGACCGAGGTATAAGATTCCTCCATGATCAGATAATGAGTGTGAA
AACAGTGGATCTCACACTGGTGATTTATGGATCGTTCAGACATTGGGGTCATCCTTTTATAGATTATTACGC
TGGACTAGAAAAATTACATTCCCAAGTAACCATGAAGAAAGATATTGATGTGTCATATGCAAAGCACTTGC
AAGTGATTTAGCTCGGATTGTTCTATTTCAACAGTTCAATGATCATAAAAAGTGGTTCGTGAATGGAGACTT
GCTCCCTCATGATCATCCCTTTAAAAGTCATGTTAAAGAAAATACATGGCCCACAGCTGCTCAAGTTCAAGA
TTTTGGAGATAAATGGCATGAACTTCCGCTGATTAAATGTTTTGAAATACCCGACTTACTAGACCCATCGAT
AATATACTCTGACAAAAGTCATTCAATGAATAGGTCAGAGGTGTTGAAACATGTCCGAATGAATCCGAACAC
TCCTATCCCTAGTAAAAAGGTGTTGCAGACTATGTTGGACACAAAGGCTACCAATTGGAAAGAATTTCTTAA
AGAGATTGATGAGAAGGGCTTAGATGATGATGATCTAATTATTGGTCTTAAAGGAAAGGAGAGGGAACTGAA
GTTGGCAGGTAGATTTTTCTCCCTAATGTCTTGGAAATTGCGAGAATACTTTGTAATTACCGAATATTTGAT
AAAGACTCATTTCGTCCCTATGTTTAAAGGCCTGACAATGGCGGACGATCTAACTGCAGTCATTAAAAAGAT
GTTAGATTCCTCATCCGGCCAAGGATTGAAGTCATATGAGGCAATTTGCATAGCCAATCACATTGATTACGA
AAAATGGAATAACCACCAAAGGAAGTTATCAAACGGCCCAGTGTTCCGAGTTATGGGCCAGTTCTTAGGTTA
TCCATCCTTAATCGAGAGAACTCATGAATTTTTTGAGAAAAGTCTTATATACTACAATGGAAGACCAGACTT
GATGCGTGTTCACAACAACACACTGATCAATTCAACCTCCCAACGAGTTTGTTGGCAAGGACAAGAGGGTGG
ACTGGAAGGTCTACGGCAAAAAGGATGGAGTATCCTCAATCTACTGGTTATTCAAAGAGAGGCTAAAATCAG
AAACACTGCTGTCAAAGTCTTGGCACAAGGTGATAATCAAGTTATTTGCACACAGTATAAAACGAAGAAATC
GAGAAACGTTGTAGAATTACAGGGTGCTCTCAATCAAATGGTTTCTAATAATGAGAAAATTATGACTGCAAT
CAAAATAGGGACAGGGAAGTTAGGACTTTTGATAAATGACGATGAGACTATGCAATCTGCAGATTACTTGAA
TTATGGAAAAATACCGATTTTCCGTGGAGTGATTAGAGGGTTAGAGACCAAGAGATGGTCACGAGTGACTTG
TGTCACCAATGACCAAATACCCACTTGTGCTAATATAATGAGCTCAGTTTCCACAAATGCTCTCACCGTAGC
TCATTTTGCTGAGAACCCAATCAATGCCATGATACAGTACAATTATTTTGGGACATTTGCTAGACTCTTGTT
GATGATGCATGATCCTGCTCTTCGTCAATCATTGTATGAAGTTCAAGATAAGATACCGGGCTTGCACAGTTC
TACTTTCAAATACGCCATGTTGTATTTGGACCCTTCCATTGGAGGAGTGTCGGGCATGTCTTTGTCCAGGTT
TTTGATTAGAGCCTTCCCAGATCCCGTAACAGAAAGTCTCTCATTCTGGAGATTCATCCATGTACATGCTCG
AAGTGAGCATCTGAAGGAGATGAGTGCAGTATTTGGAAACCCCGAGATAGCCAAGTTTCGAATAACTCACAT
AGACAAGCTAGTAGAAGATCCAACCTCTCTGAACATCGCTATGGGAATGAGTCCAGCGAACTTGTTAAAGAC
TGAGGTTAAAAAATGCTTAATCGAATCAAGACAAACCATCAGGAACCAGGTGATTAAGGATGCAACCATATA
```

Figure 14 continued

```
TTTGTATCATGAAGAGGATCGGCTCAGAAGTTTCTTATGGTCAATAAATCCTCTGTTCCCTAGATTTTTAAG
TGAATTCAAATCAGGCACTTTTTTGGGAGTCGCAGACGGGCTCATCAGTCTATTTCAAAATTCTCGTACTAT
TCGGAACTCCTTTAAGAAAAAGTATCATAGGGAATTGGATGATTTGATTGTGAGGAGTGAGGTATCCTCTTT
GACACATTTAGGGAAACTTCATTTGAGAAGGGGATCATGTAAAATGTGGACATGTTCAGCTACTCATGCTGA
CACATTAAGATACAAATCCTGGGGCCGTACAGTTATTGGGACAACTGTACCCCATCCATTAGAAATGTTGGG
TCCACAACATCGAAAGAGACTCCTTGTGCACCATGTAACACATCAGGGTTCAATTATGTTTCTGTGCATTG
TCCAGACGGGATCCATGACGTCTTTAGTTCACGGGACCATTGCCTGCTTATCTAGGGTCTAAAACATCTGA
ATCTACATCTATTTTGCAGCCTTGGGAAAGGGAAAGCAAAGTCCCACTGATTAAAAGAGCTACACGTCTTAG
AGATGCTATCTCTTGGTTTGTTGAACCCGACTCTAAACTAGCAATGACTATACTTTCTAACATCCACTCTTT
AACAGGCGAAGAATGGaCCAAAAGGCAGCATGGGTTCAAAAGAACAGGGTCTGCCCTTCATAGGTTTTCGAC
ATCTCGGATGAGCCATGGTGGGTTCGCATCTCAGAGCACTGCAGCATTGACCAGGTTGATGGCAaCTACAGA
CACCATGAGGGATCTGGGAGATCAGAATTTCGACTTTTTATTCCAGGCAACGTTGCTCTATGCTCAGATTAC
CACCACTGTTGCAAGAGACGGATGGATCACCAGTTGTACAGATCATTATCATATTGCCTGTAAGTCCTGTTT
GAGACCCATAGAAGAGATCACCCTGGACTCAAGTATGGACTACACGCCCCAGATGTATCCCATGTGCTGAA
GACATGGAGGAATGGGGAAGGTTCGTGGGGACAAGAGATAAAACAGATCTATCCTTTAGAAGGGAATTGGAA
GAATTTAGCACCTGCTGAGCAATCCTATCAAGTCGGCAGATGTATAGGTTTTCTATATGGAGACTTGGCGTA
TAGAAAATCTACTCATGCCGAGGACAGTTCTCTATTTCCTCTATCTATACAAGGTCGTATTAGAGGTCGAGG
TTTCTTAAAAGGGTTGCTAGACGGATTAATGAGAGCAAGTTGCTGCCAAGTAATACACCGGAGAAGTCTGGC
TCATTTGAAGAGGCCGGCCAACGCAGTGTACGGAGGTTTGATTTACTTGATTGATAAATTGAGTGtATCACC
TCCATTCCTTTCTCTTACTAGATCAGGACCTATTAGAGACGAATTAGAAACGATTCCCCACAAGATCCCAAC
CTCCTATCCGACAAGCAACCGTGATATGGGGGTGATTGTCAGAAATTACTTCAAATACCAATGCCGTCTAAT
TGAAAAGGGAAAATACAGATCACATTATTCACAATTATGGTTATTCTCAGATGTCTTATCCATAGACTTCAT
TGGACCATTCTCTATTTCCACCACCCTCTTGCAAATCCTATACAAGCCATTTTTATCTGGGAAAGATAAGAA
TGAGTTGAGAGAGCTGGCAAATCTTTCTTCATTGCTAAGATCAGGAGAGGGGTGGGAAGACATACATGTAAA
ATTCTTCACCAAGGACATATTATTGTGTCCAGAGGAAATCAGACATGCTTGCAAGTTCGGGATTGCTAAGGA
TAATAATAAAGACATGAGCTATCCCCCTTGGGGAAGGGAATCCAGAGGGACAATTACAACAATCCCTGTTTA
TTATACGACCACCCCTTACCCAAAGATGCTAGAGATGCCTCCAAGAATCCAAAATCCCCTGCTGTCCGGAAT
CAGGTTGGGCCAGTTACCAACTGGCGCTCATTATAAAATTCGGAGTATATTACATGGAATGGGAATCCaTTA
CAGGGACTTCTTGAGTTGTGGAGACGGCTCCGGAGGGATGACTGCTGCATTACTACGAGAAAATGTGCATAG
CAGAGGAATATTCAATAGTCTGTTAGAATTATCAGGGTCAGTCATGCGAGGCGCCTCTCCTGAGCCCCCCAG
TGCCCTAGAAACTTTAGGAGGAGATAAATCGAGATGTGTAAATGGTGAAACATGTTGGGAATATCCATCTGA
CTTATGTGACCCAAGGACTTGGGACTATTTCCTCCGACTCAAAGCAGGCTTGGGGCTTCAAATTGATTTAAT
TGTAATGGATATGGAAGTTCGGGATTCTTCTACTAGCCTGAAAATTGAGACGAATGTTAGAAATTATGTGCA
CCGGATTTTGGATGAGCAAGGAGTTTTAATCTACAAGACTTATGGAACATATATTTGTGAGAGCGAAAAGAA
TGCAGTAACAATCCTTGGTCCCATGTTCAAGACGGTCGACTTAGTTCAAACAGAATTTAGTAGTTCTCAAAC
GTCTGAAGTATATATGGTATGTAAAGGTTTGAAGAAATTAATCGATGAACCCAATCCCGATTGGTCTTCCAT
```

Figure 14 continued

```
CAATGAATCCTGGAAAAACCTGTACGCATTCCAGTCATCAGAACAGGAATTTGCCAGAGCAAAGAAGGTTAG
TACATACTTTACCTTGACAGGTATTCCCTCCCAATTCATTCCTGATCCTTTTGTGAACATTGAGACTATGCT
ACAAATATTCGGAGTACCCACGGGTGTGTCTCATGCGGCTGCCTTAAAATCATCTGATAGACCTGCAGATTT
ATTGACCATTAGCCTTTTTTATATGGCGATTATATCGTATTATAACATCAATCATATCAGAGTAGGACCGAT
ACCTCCGAACCCCCCATCAGATGGAATTGCACAAAATGTGGGGATCGCTATAACTGGTATAAGCTTTTGGCT
GAGTTTGATGGAGAAAGACATTCCACTATATCAACAGTGTTTAGCAGTTATCCAGCAATCATTCCCGATTAG
GTGGGAGGCTGTTTCAGTAAAAGGAGGATACAAGCAGAAGTGGAGTACTAGAGGTGATGGGCTCCCAAAAGA
TACCCGAATTTCAGACTCCTTGGCCCCAATCGGGAACTGGATCAGATCTCTGGAATTGGTCCGAAACCAAGT
TCGTCTGAATCCATTCAATGAGATCTTGTTCAATCAGCTATGTCGTACAGTGGATAATCATTTGAAATGGTC
AAATTTGCGAAAAAACACAGGAATGATTGAATGGATCAATAGACGAATTTCAAAAGAAGACCGGTCTATACT
GATGTTGAAGAGTGACCTACATGAGGAAAACTCTTGGAGAGATTAAAAAATCATGAGGAGACTCCAAACTTT
AAGTATGAAAAAACTTTGATCCTTAAGACCCTCTTGTGGTTTTTATTTTTATCTGGTTTTGTGGTCTTCG
T
```

Figure 14 continued

*Nucleic Acid Sequence of the M Protein Gene for VSV Mutant AV2*

ATGAGTTCCTTAAAGAAGATTCTCGGTCTGAAGGGGAAAGGTAAGAAATCTAAGAAATTAGGGATCGCACCA
CCCCCTTATGAAGAGGACACTAACATGGAGTATGCTCCGAGCGCTCCAATTGACAAATCCTATTTTGGAGTT
GACGAGAGGGACACTCATGATCCGCATCAATTAAGATATGAGAAATTCTTCTTTACAGTGAAAATGACGGTT
AGATCTAATCGTCCGTTCAGAACATACTCAGATGTGGCAGCCGCTGTATCCCATTGGGATCACATGTACATC
GGAATGGCAGGGAAACGTCCCTTCTACAAGATCTTGGCTTTTTTGGGTTCTTCTAATCTAAAGGCCACTCCA
GCGGTATTGGCAGATCAAGGTCAACCAGAGTATCACGCTCACTGTGAAGGCAGGGCTTATTTGCCACACAGA
ATGGGGAAGACCCCTCCCATGCTCAATGTACCAGAGCACTTCAGAAGACCATTCAATATAGGTCTTTACAAG
GGAACGGTTGAGCTCACAATGACCATCTACGATGATGAGTCACTGGAAGCAGCTCCTATGATCTGGGATCAT
TTCAATTCTTCCAAATTTTCTGATTTCAGAGAGAAGGCCTTAATGTTTGGCCTGATTGTCGAGAAAAAGGCA
TCTGGAGCTTGGGTCCTGGATTCTGTCAGCCACTTCAAATGA

FIGURE 15

*Amino Acid Sequence for the M Protein of VSV Mutant AV2*

MSSLKKILGLKGKGKKSKKLGIAPPPYEEDTNMEYAPSAPIDKSYFGVDEMDTHDPHQLRYEKFFFTVKMTV
RSNRPFRTYSDVAAAVSHWDHMYIGMAGKRPFYKILAFLGSSNLKATPAVLADQGQPEYHAHCEGRAYLPHR
MGKTPPMLNVPEHFRRPFNIGLYKGTVELTMTIYDDESLEAAPMIWDHFNSSKFSDFREKALMFGLIVEKKA
SGAWFLDSVRHFK

FIGURE 16

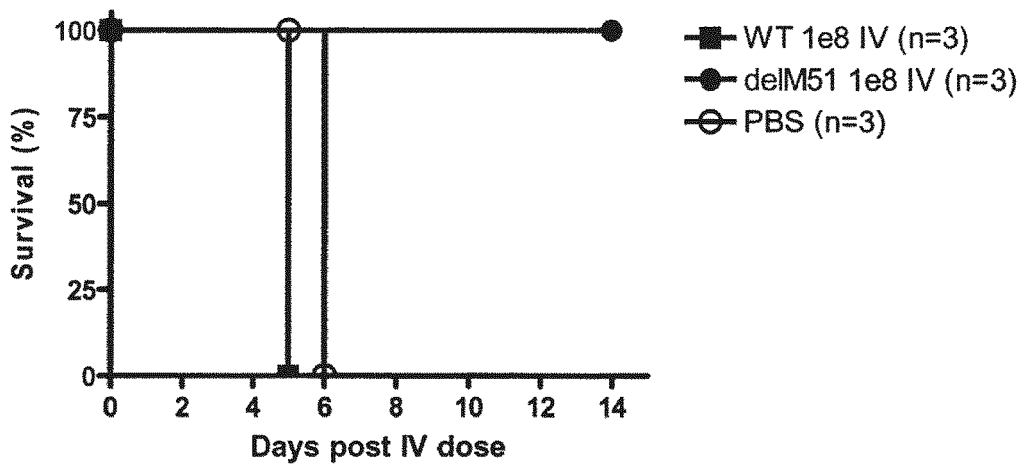
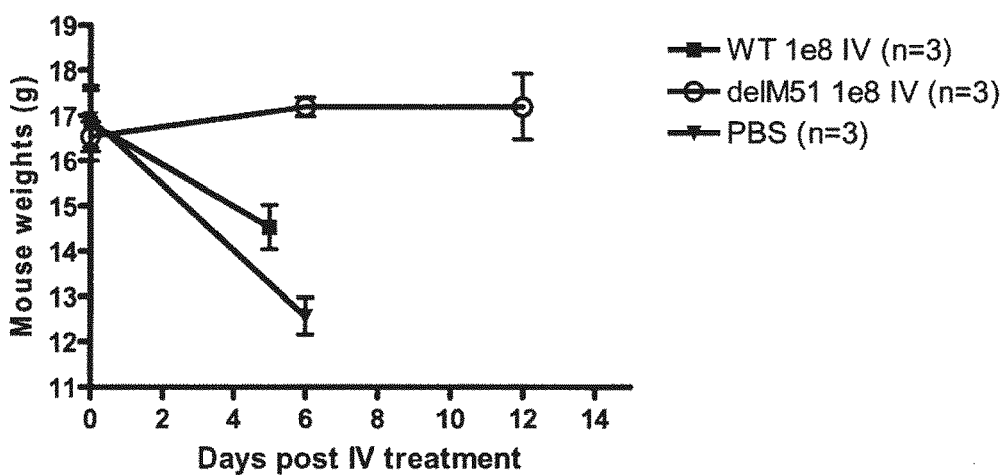
FIGURE 17A-B

A
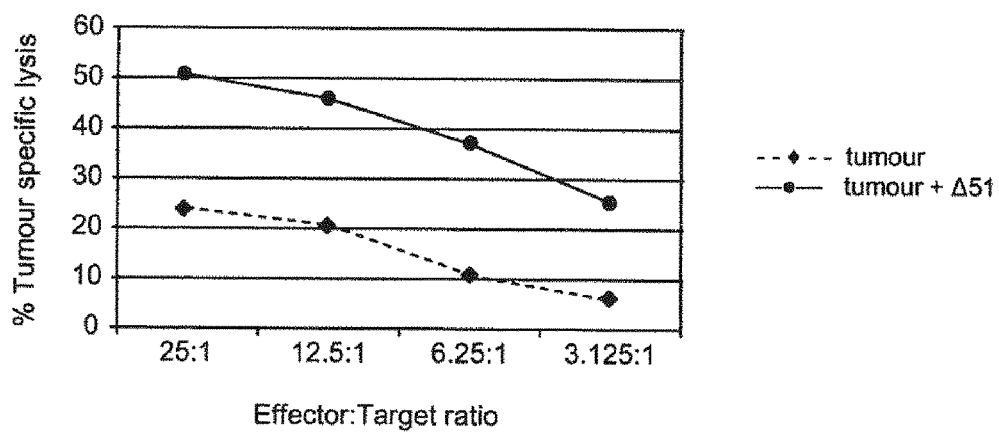
B
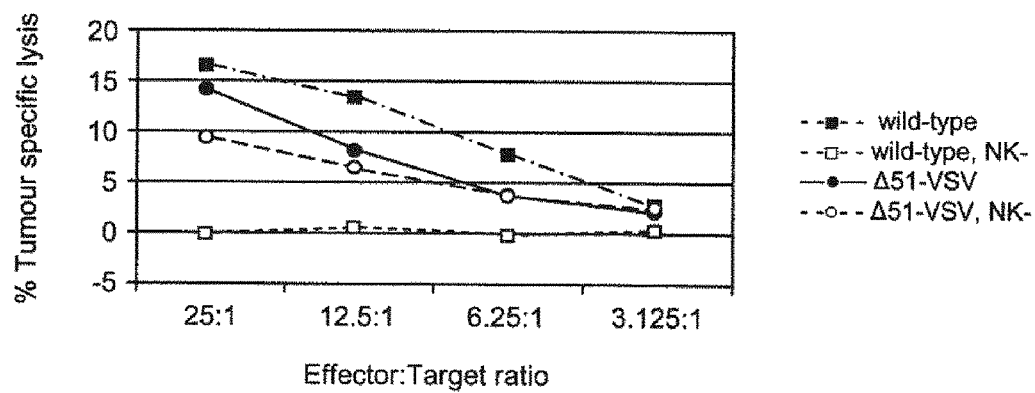
FIGURE 19

SEQUENCE LISTING

```
<160> NUMBER OF SEQ ID NOS: 32

<210> SEQ ID NO 1
<211> LENGTH: 11161
<212> TYPE: DNA
<213> ORGANISM: Vesicular stomatitis virus

<400> SEQUENCE: 1
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga atacccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact tgtatggagc attgaaggac     300
atccggggta agttggataa agattggtca agtttcggaa taaacatcgg gaaggcaggg     360
```

```
gatacaatcg gaatatttga ccttgtatcc ttgaaagccc tggacggtgt acttccagat    420
ggagtatcgg atgcttccag aaccagcgca gatgacaaat ggttgccttt gtatctactt    480
ggcttataca gagtgggcag aacacaaatg cctgaataca gaaaaaggct catggatggg    540
ctgacaaatc aatgcaaaat gatcaatgaa cagtttgaac ctcttgtgcc agaaggtcgt    600
gacatttttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca catttggac acctctgcaa ataaccgga     780 atgtctacag aagatgtaac gacctggatc ttgaaccgag aagttgcaga tgagatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tctaccagag caaggaatgc ccgacagcct   1020
gatgacattg agtatacatc tcttactaca gcaggtttgt tgtacgctta tgcagtagga   1080
tcctctgctg acttggcaca acagttttgt gttggagata gcaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaacga   1260
gcagtcatgt cactgcaagg cctaagagag aagacaattg gcaagtatgc taagtcagaa   1320
tttgacaaat gaccctataa ttctcagatc acctattata tattatgcta catatgaaaa   1380
aaactaacag atatcatgga taatctcaca aaagttcgtg agtatctcaa gtcctattct   1440
cgtctagatc aggcggtagg agagatagat gagatcgaag cacaacgagc tgaaaagtcc   1500
aattatgagt tgttccaaga ggacggagtg aagagcata ctaggccctc ttattttcag    1560
gcagcagatg attctgacac agaatctgaa ccagaaattg aagacaatca aggcttgtat   1620
gtaccagatc cggaagctga gcaagttgaa ggctttatac aggggccttt agatgactat   1680
gcggatgagg acgtggatgt tgtattcact tcggactgga acagcctga gcttgaatcc   1740 gacgagcatg gaaagacctt acggttgaca ttgccagagg gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt cccaatcaga agccgtatca   1980
gatgtttggt ctctctcaaa gacatccatg actttccaac caagaaagc aagtcttcag    2040 cctctcacca tatccttgga tgaattgttc tcatctagag gagaattcat ctctgtcgga   2100
ggtaacggac gaatgtctca taagaggcc atcctgctcg gtctgaggta caaaaagttg    2160
tacaatcagg cgagagtcaa atattctctg tagactatga aaaaaagtaa cagatatcac   2220
aatctaagtg ttatcccaat ccattcatca tgagttcctt aaagaagatt ctcggtctga   2280
aggggaaagg taagaaatct aagaaattag ggatcgcacc acccccttat gaagaggaca   2340
ctaacatgga gtatgctccg agcgctccaa ttgacaaatc ctattttgga gttgacgaga   2400
gggacactca tgatccgcat caattaagat atgagaaatt cttctttaca gtgaaaatga   2460
cggttagatc taatcgtccg ttcagaacat actcagatgt ggcagccgct gtatcccatt   2520
gggatcacat gtcatcgga atggcaggga acgtcccctt ctacaagatc ttggcttttt    2580
tgggttcttc taatctaaag gccactccag cggtattggc agatcaaggt caaccagagt   2640
atcacgctca ctgtgaaggc agggcttatt tgccacacag aatggggaag accccctccca  2700 tgctcaatgt accagagcac ttcagaagac cattcaatat aggtctttac aagggaacgg    2760
```

```
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcttggg tcctggattc tgtcagccac ttcaaatgag   2940
ctagtctagc ttccagcttc tgaacaatcc ccggtttact cagtctctcc taattccagc   3000
ctttcgaaca actaatatcc tgtcttttct atccctatga aaaaactaa cagagatcga   3060 tctgttttcct tgacaccatg aagtgccttt tgtacttagc tttttattc atcggggtga   3120 attgcaagtt caccatagtt tttccataca accgaaaagg aaactggaaa aatgttcctt   3180
ccaattacca ttattgcccg tcaagctcag atttaaattg gcataatgac ttaataggca   3240
cagccttaca agtcaaaatg cccaagagtc acaaggctat tcaagcagac ggttggatgt   3300
gtcatgcttc caaatgggtc actacttgtg atttccgctg gtacggaccg aagtatataa   3360
cacattccat ccgatccttc actccatctg tagaacaatg caaggaaagc attgaacaaa   3420
cgaaacaagg aacttggctg aatccaggct tccctcctca aagttgtgga tatgcaactg   3480
tgacggatgc tgaagcagcg attgtccagg tgactcctca ccatgtgctt gttgatgaat   3540
acacaggaga atgggttgat tcacagttca tcaacgaaa atgcagcaat gacatatgcc   3600
ccactgtcca taactccaca acctggcatt ccgactataa ggtcaaaggg ctatgtgatt   3660
ctaacctcat ttccatggac atcaccttct tctcagagga cggagagcta tcatccctag   3720
gaaaggaggg cacagggttc agaagtaact actttgctta tgaaactgga gacaaggcct   3780
gcaaaatgca gtactgcaag cattgggag tcagactccc atcaggtgtc tggttcgaga   3840
tggctgataa ggatctcttt gctgcagcca gattccctga tgcccagaa gggtcaagta   3900 tctctgctcc atctcagacc tcagtggatg taagtctcat tcaggacgtt gagaggatct   3960
tggattattc cctctgccaa gaaacctgga gcaaaatcag agcgggtctt cccatctctc   4020
cagtggatct cagctatctt gctcctaaaa acccaggaac cggtcctgtc tttaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggctcc atatgaagac gtggaaattg gacccaatgg agttctgagg accagttcag   4260
gatataagtt tcctttatat atgattggac atggtatgtt ggactccgat cttcatctta   4320
gctcaaaggc tcaggtgttt gaacatcctc acattcaaga cgctgcttcg cagcttcctg   4380
atgatgagac tttatttttt ggtgatactg ggctatccaa aaatccaatc gagttttgtag   4440 aaggttggtt cagtagttgg aagagctcta ttgcctcttt tttctttatc atagggttaa   4500
tcattggact attcttggtt ctccgagttg gtatttatct ttgcattaaa ttaaagcaca   4560
ccaagaaaag acagatttat acagacatag agatgaaccg acttgggaag taactcaaat   4620
cctgcacaac agattcttca tgtttgaacc aaatcaactt gtgatatcat gctcaaagag   4680
gccttaatta tattttaatt tttaattttt atgaaaaaaa ctaacagcaa tcatggaagt   4740
ccacgatttt gagaccgacg agttcaatga tttcaatgaa gatgactatg ccacaagaga   4800
attcctgaat cccgatgagc gcatgacgta cttgaatcat gctgattaca atttgaattc   4860
tcctctaatt agtgatgata ttgacaattt gatcaggaaa ttcaattctc ttccgattcc   4920
ctcgatgtgg gatagtaaga actgggatgg agttcttgag atgttaacat catgtcaagc   4980
caatcccatc tcaacatctc agatgcataa atggatggga agttggttaa tgtctgataa   5040
tcatgatgcc agtcaagggt atagttttt acatgaagtg gacaaagagg cagaaataac   5100
atttgacgtg gtggagacct tcatccgcgg ctggggcaac aaaccaattg aatacatcaa   5160
```

```
aaaggaaaga tggactgact cattcaaaat tctcgcttat ttgtgtcaaa agttttttgga    5220
cttacacaag ttgacattaa tcttaaatgc tgtctctgag gtggaattgc tcaacttggc    5280
gaggactttc aaaggcaaag tcagaagaag ttctcatgga acgaacatat gcaggcttag    5340
ggttcccagc ttgggtccta cttttatttc agaaggatgg gcttacttca agaaacttga    5400
tattctaatg gaccgaaact ttctgttaat ggtcaaagat gtgattatag ggaggatgca    5460
aacggtgcta tccatggtat gtagaataga caacctgttc tcagagcaag acatcttctc    5520
ccttctaaat atctcacagaa ttggagataa aattgtggag aggcagggaa attttttctta   5580
tgacttgatt aaaatggtgg aaccgatatg caacttgagg ctgatgaaat tagcaagaga    5640
atcaaggcct ttagtcccac aattccctca ttttgaaaat catatcaaga cttctgttga    5700
tgaagggca aaaattgacc gaggtataag attcctccat gatcagataa tgagtgtgaa     5760
aacagtggat ctcacactgg tgatttatgg atcgttcaga cattgggtc atccttttat     5820
agattattac gctggactag aaaaattaca ttcccaagta accatgaaga aagatattga    5880
tgtgtcatat gcaaaagcac ttgcaagtga tttagctcgg attgttctat ttcaacagtt    5940
caatgatcat aaaaagtggt tcgtgaatgg agacttgctc cctcatgatc atccctttaa    6000
aagtcatgtt aaagaaaata catggcccac agctgctcaa gttcaagatt ttggagataa    6060
atggcatgaa cttccgctga ttaaatgttt tgaaataccc gacttactag acccatcgat    6120
aatatactct gacaaaagtc attcaatgaa taggtcagag gtgttgaaac atgtccgaat    6180
gaatccgaac actcctatcc ctagtaaaaa ggtgttgcag actatgttgg acacaaaggc    6240
taccaattgg aaagaatttc ttaaagagat tgatgagaag ggcttagatg atgatgatct    6300
aattattggt cttaaaggaa aggagaggga actgaagttg gcaggtagat ttttctccct    6360
aatgtcttgg aaattgcgag aatactttgt aattaccgaa tatttgataa agactcattt    6420
cgtccctatg tttaaaggcc tgacaatggc ggacgatcta actgcagtca ttaaaaagat    6480
gttagattcc tcatccggcc aaggattgaa gtcatatgag gcaatttgca tagccaatca    6540
cattgattac gaaaaatgga ataaccacca aaggaagtta tcaaacggcc cagtgttccg    6600
agttatgggc cagttcttag gttatccatc cttaatcgag agaactcatg aatttttttga   6660
gaaaagtctt atatactaca atggaagacc agacttgatg cgtgttcaca acaacacact    6720
gatcaattca acctcccaac gagtttgttg gcaaggacaa gagggtggac tggaaggtct    6780
acggcaaaaa ggatggagta tcctcaatct actggttatt caagagagg ctaaaatcag     6840
aaacactgct gtcaaagtct tggcacaagg tgataatcaa gttatttgca cacagtataa    6900
aacgaagaaa tcgagaaacg ttgtagaatt acagggtgct ctcaatcaaa tggtttctaa    6960
taatgagaaa attatgactg caatcaaaat agggacaggg aagttaggac ttttgataaa    7020
tgacgatgag actatgcaat ctgcagatta cttgaattat ggaaaaatac cgattttccg    7080
tggagtgatt agagggttag agaccaagag atggtcacga gtgacttgtg tcaccaatga    7140
ccaaataccc acttgtgcta atataatgag ctcagtttcc acaaatgctc tcaccgtagc    7200
tcattttgct gagaacccaa tcaatgccat gatacagtac aattatttttg ggacatttgc   7260
tagactcttg ttgatgatgc atgatcctgc tcttcgtcaa tcattgtatg aagttcaaga    7320
taagataccg ggcttgcaca gttctacttt caaatacgcc atgttgtatt tggacccttc    7380
cattggagga gtgtcgggca tgtctttgtc caggttttttg attagagcct tcccagatcc    7440
cgtaacagaa agtctctcat tctggagatt catccatgta catgctcgaa gtgagcatct    7500
gaaggagatg agtgcagtat ttggaaaccc cgagatagcc aagtttcgaa taactcacat    7560
```

```
agacaagcta gtagaagatc caacctctct gaacatcgct atgggaatga gtccagcgaa   7620
cttgttaaag actgaggtta aaaaatgctt aatcgaatca agacaaacca tcaggaacca   7680
ggtgattaag gatgcaacca tatatttgta tcatgaagag gatcggctca gaagtttctt   7740
atggtcaata atcctctgt tccctagatt tttaagtgaa ttcaaatcag gcactttttt   7800
gggagtcgca gacgggctca tcagtctatt tcaaaattct cgtactattc ggaactcctt   7860
taagaaaaag tatcataggg aattggatga tttgattgtg aggagtgagg tatcctcttt   7920
gacacattta gggaaacttc atttgagaag gggatcatgt aaaatgtgga catgttcagc   7980
tactcatgct gacacattaa gatacaaatc ctggggccgt acagttattg ggacaactgt   8040
accccatcca ttagaaatgt tgggtccaca acatcgaaaa gagactcctt gtgcaccatg   8100
taacacatca gggttcaatt atgtttctgt gcattgtcca gacgggatcc atgacgtctt   8160
tagttcacgg ggaccattgc ctgcttatct agggtctaaa acatctgaat ctacatctat   8220
tttgcagcct tgggaaaggg aaagcaaagt cccactgatt aaaagagcta cacgtcttag   8280
agatgctatc tcttggtttg ttgaacccga ctctaaacta gcaatgacta actttctaa    8340 catccactct ttaacaggcg aagaatggac caaaaggcag catgggttca aaagaacagg   8400
gtctgccctt cataggtttt cgacatctcg gatgagccat ggtgggttcg catctcagag   8460
cactgcagca ttgaccaggt tgatggcaac tacagacacc atgagggatc tgggagatca   8520
gaatttcgac ttttttattcc aggcaacgtt gctctatgct cagattacca ccactgttgc   8580
aagagacgga tggatcacca gttgtacaga tcattatcat attgcctgta agtcctgttt   8640
gagacccata aagagatca ccctggactc aagtatggac tacacgcccc cagatgtatc   8700
ccatgtgctg aagacatgga ggaatgggga aggttcgtgg ggacaagaga taaaacagat   8760
ctatccttta gaagggaatt ggaagaattt agcacctgct gagcaatcct atcaagtcgg   8820
cagatgtata ggttttctat atggagactt ggcgtataga aaatctactc atgccgagga   8880
cagttctcta tttcctctat ctatacaagg tcgtattaga ggtcgaggtt tcttaaaagg   8940
gttgctagac ggattaatga gagcaagttg ctgccaagta atacaccgga gaagtctggc   9000
tcatttgaag aggccggcca acgcagtgta cggaggtttg atttacttga ttgataaatt   9060
gagtgtatca cctccattcc tttctcttac tagatcagga cctattagag acgaattaga   9120
aacgattccc cacaagatcc caacctccta tccgacaagc aaccgtgata tgggggtgat   9180
tgtcagaaat tacttcaaat accaatgccg tctaattgaa aagggaaaat acagatcaca   9240
ttattcacaa ttatggttat tctcagatgt cttatccata gacttcattg gaccattctc   9300
tatttccacc accctcttgc aaatcctata caagccattt ttatctggga agataagaa    9360 tgagttgaga gagctggcaa atctttcttc attgctaaga tcaggagagg ggtgggaaga   9420
catacatgta aaattcttca ccaaggacat attattgtgt ccagaggaaa tcagacatgc   9480
ttgcaagttc gggattgcta aggataataa taaagacatg agctatcccc cttggggaag   9540
ggaatccaga gggacaatta caacaatccc tgtttattat acgaccaccc cttacccaaa   9600
gatgctagag atgcctccaa gaatccaaaa tcccctgctg tccggaatca ggttgggcca   9660
gttaccaact ggcgctcatt ataaaattcg gagtatatta catggaatgg gaatccatta   9720
cagggacttc ttgagttgtg gagacggctc cggagggatg actgctgcat tactacgaga   9780
aaatgtgcat agcagaggaa tattcaatag tctgttagaa ttatcagggt cagtcatgcg   9840
aggcgcctct cctgagcccc ccagtgccct agaaacttta ggaggagata aatcgagatg   9900
tgtaaatggt gaaacatgtt gggaatatcc atctgactta tgtgacccaa ggacttggga   9960
```

```
ctatttcctc cgactcaaag caggcttggg gcttcaaatt gatttaattg taatggatat   10020
ggaagttcgg gattcttcta ctagcctgaa aattgagacg aatgttagaa attatgtgca   10080
ccggattttg gatgagcaag gagttttaat ctacaagact tatggaacat atatttgtga   10140
gagcgaaaag aatgcagtaa caatccttgg tcccatgttc aagacggtcg acttagttca   10200
aacagaattt agtagttctc aaacgtctga agtatatatg gtatgtaaag gtttgaagaa   10260
attaatcgat gaacccaatc ccgattggtc ttccatcaat gaatcctgga aaaacctgta   10320
cgcattccag tcatcagaac aggaatttgc cagagcaaag aaggttagta catactttac   10380
cttgacaggt attccctccc aattcattcc tgatcctttt gtaaacattg agactatgct   10440
acaaatattc ggagtaccca cgggtgtgtc tcatgcggct gccttaaaat catctgatag   10500
acctgcagat ttattgacca ttagccttt ttatatggcg attatatcgt attataacat   10560
caatcatatc agagtaggac cgataacctcc gaacccccca tcagatggaa ttgcacaaaa   10620
tgtggggatc gctataactg gtataagctt ttggctgagt ttgatggaga agacattcc   10680 actatatcaa cagtgtttag cagttatcca gcaatcattc ccgattaggt gggaggctgt   10740
ttcagtaaaa ggaggataca agcagaagtg gagtactaga ggtgatgggc tcccaaaaga   10800
tacccgaatt tcagactcct tggccccaat cgggaactgg atcagatctc tggaattggt   10860
ccgaaaccaa gttcgtctga atccattcaa tgagatcttg ttcaatcagc tatgtcgtac   10920
agtggataat catttgaaat ggtcaaattt gcgaaaaaac acaggaatga ttgaatggat   10980
caatagacga atttcaaaag aagaccggtc tatactgatg ttgaagagtg acctacatga   11040
ggaaaactct tggagagatt aaaaaatcat gaggagactc caaactttaa gtatgaaaaa   11100
aactttgatc cttaagaccc tcttgtggtt tttattttt atctggtttt gtggtcttcg   11160
t                                                                   11161

<210> SEQ ID NO 2
<211> LENGTH: 690
<212> TYPE: DNA
<213> ORGANISM: Vesicular stomatitis virus

<400> SEQUENCE: 2
atgagttcct taaagaagat tctcggtctg aaggggaaag gtaagaaatc taagaaatta     60
gggatcgcac cacccccctta tgaagaggac actaacatgg agtatgctcc gagcgctcca    120
attgacaaat cctatttggg agttgacgag atggacactc atgatccgca tcaattaaga    180
tatgagaaat tcttctttac agtgaaaatg acggttagat ctaatcgtcc gttcagaaca    240
tactcagatg tggcagccgc tgtatcccat tgggatcaca tgtacatcgg aatggcaggg    300
aaacgtccct tctacaagat cttggctttt ttgggttctt ctaatctaaa ggccactcca    360
gcggtattgg cagatcaagg tcaaccagag tatcacgctc actgtgaagg cagggcttat    420
ttgccacaca gaatggggaa gacccctccc atgctcaatg taccagagca cttcagaaga    480
ccattcaata taggtctttta caagggaacg gttgagctca caatgaccat ctacgatgat    540
gagtcactgg aagcagctcc tatgatctgg gatcattca attcttccaa attttctgat    600
ttcagagaga aggccttaat gtttggcctg attgtcgaga aaaaggcatc tggagcttgg    660
ttcctggatt ctgtcagaca cttcaaatga                                     690

<210> SEQ ID NO 3
<211> LENGTH: 229
<212> TYPE: PRT
<213> ORGANISM: Vesicular stomatitis virus
```

<400> SEQUENCE: 3

```
Met Ser Ser Leu Lys Lys Ile Leu Gly Leu Lys Gly Lys Gly Lys Lys
1               5                   10                  15
Ser Lys Lys Leu Gly Ile Ala Pro Pro Tyr Glu Glu Asp Thr Asn
            20                  25                  30
Met Glu Tyr Ala Pro Ser Ala Pro Ile Asp Lys Ser Tyr Phe Gly Val
            35                  40                  45
Asp Glu Arg Asp Thr His Asp Pro His Gln Leu Arg Tyr Glu Lys Phe
            50                  55                  60
Phe Phe Thr Val Lys Met Thr Val Arg Ser Asn Arg Pro Phe Arg Thr
65                  70                  75                  80
Tyr Ser Asp Val Ala Ala Val Ser His Trp Asp His Met Tyr Ile
                    85                  90                  95
Gly Met Ala Gly Lys Arg Pro Phe Tyr Lys Ile Leu Ala Phe Leu Gly
                100                 105                 110
Ser Ser Asn Leu Lys Ala Thr Pro Ala Val Leu Ala Asp Gln Gly Gln
                115                 120                 125
Pro Glu Tyr His Ala His Cys Glu Gly Arg Ala Tyr Leu Pro His Arg
    130                 135                 140
Met Gly Lys Thr Pro Pro Met Leu Asn Val Pro Glu His Phe Arg Arg
145                 150                 155                 160
Pro Phe Asn Ile Gly Leu Tyr Lys Gly Thr Val Glu Leu Thr Met Thr
                165                 170                 175
Ile Tyr Asp Asp Glu Ser Leu Glu Ala Ala Pro Met Ile Trp Asp His
                180                 185                 190
Phe Asn Ser Ser Lys Phe Ser Asp Phe Arg Glu Lys Ala Leu Met Phe
                195                 200                 205
Gly Leu Ile Val Glu Lys Lys Ala Ser Gly Ala Trp Val Leu Asp Ser
            210                 215                 220
Val Ser His Phe Lys
225
```

<210> SEQ ID NO 4
<211> LENGTH: 11161
<212> TYPE: DNA
<213> ORGANISM: Vesicular stomatitis virus

<400> SEQUENCE: 4

```
acgaagacaa acaaaccatt attatcatta aaaggctcag gagaaacttt aacagtaatc    60
aaaatgtctg ttacagtcaa gagaatcatt gacaacacag tcatagttcc aaaacttcct   120
gcaaatgagg atccagtgga atacccggca gattacttca aaaatcaaa ggagattcct   180
ctttacatca atactacaaa aagtttgtca gatctaagag atatgtcta ccaaggcctc   240
aaatccggaa atgtatcaat catacatgtc aacagctact gtatggagc attgaaggac   300
atccggggta agttggataa agattggtca gtttcggaa taaacatcgg aaggcaggg   360
gatacaatcg gaatatttga ccttgtatcc ttgaaagccc tggacggtgt acttccagat   420
ggagtatcgg atgcttccag aaccagcgca gatgacaaat ggttgccttt gtatctactt   480
ggcttataca gagtgggcag aacacaaatg cctgaataca gaaaaggct catggatggg   540
ctgacaaatc aatgcaaaat gatcaatgaa cagtttgaac ctcttgtgcc agaaggtcgt   600
gacatttttg atgtgtgggg aaatgacagt aattacacaa aaattgtcgc tgcagtggac   660
atgttcttcc acatgttcaa aaaacatgaa tgtgcctcgt tcagatacgg aactattgtt   720
```

```
tccagattca aagattgtgc tgcattggca acatttggac acctctgcaa aataaccgga    780
atgtctacag aagatgtaac gacctggatc ttgaaccgag aagttgcaga tgagatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgctg acttggcaca acagttttgt gttggagata gcaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaacga   1260
gcagtcatgt cactgcaagg cctaagagag aagacaattg caagtatgc taagtcagaa    1320
tttgacaaat gaccctataa ttctcagatc acctattata tattatgcta catatgaaaa   1380
aaactaacag atatcatgga taatctcaca aaagttcgtg agtatctcaa gtcctattct   1440
cgtctagatc aggcggtagg agagatagat gagatcgaag cacaacgagc tgaaaagtcc   1500
aattatgagt tgttccaaga ggacggagtg gaagagcata ctaggccctc ttattttcag   1560
gcagcagatg attctgacac agaatctgaa ccagaaattg aagacaatca aggcttgtat   1620
gtaccagatc cggaagctga gcaagttgaa ggctttatac aggggccttt agatgactat   1680
gcggatgagg acgtggatgt tgtattcact tcggactgga acagcctga gcttgaatcc    1740
gacgagcatg gaaagacctt acggttgaca ttgccagagg gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt cccaatcgga agccgtatca   1980
gatgtttggt ctctctcaaa gacatccatg actttccaac ccaagaaagc aagtcttcag   2040
cctctcacca tatccttgga tgaattgttc tcatctagag gagaattcat ctctgtcgga   2100
ggtaacggac gaatgtctca taagagggcc atcctgctcg gtctgaggta caaaaagttg   2160
tacaatcagg cgagagtcaa atattctctg tagactatga aaaaaagtaa cagatatcac   2220
aatctaagtg ttatcccaat ccattcatca tgagttcctt aaagaagatt ctcggtctga   2280
aggggaaagg taagaaatct aagaaattag ggatcgcacc acccccttat gaagaggaca   2340
ctaacatgga gtatgctccg agcgctccaa ttgacaaatc ctattttgga gttgacgaga   2400
tggacactca tgatccgcat caattaagat atgagaaatt cttctttaca gtgaaaatga   2460
cggttagatc taatcgtccg ttcagaacat actcagatgt ggcagccgct gtatcccatt   2520
gggatcacat gtcatcgga atggcaggga acgtcccctt ctacaagatc ttggcttttt    2580
tgggttcttc taatctaaag gccactccag cggtattggc agatcaaggt caaccagagt   2640
atcacgctca ctgtgaaggc agggcttatt tgccacacag aatggggaag acccctccca   2700
tgctcaatgt accagagcac ttcagaagac cattcaatat aggtctttac aagggaacgg   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcttggt tcctggattc tgtcagacac ttcaaatgag   2940
ctagtctagc ttccagcttc tgaacaatcc ccggtttact cagtctctcc taattccagc   3000
ctttcgaaca actaatatcc tgtctttcct atccctatga aaaaaactaa cagagatcga   3060
tctgtttcct tgacaccatg aagtgccttt tgtacttagc tttttattc atcggggtga    3120
```

```
attgcaagtt caccatagtt tttccataca accaaaaagg aaactggaaa aatgttcctt    3180
ccaattacca ttattgcccg tcaagctcag atttaaattg gcataatgac ttaataggca    3240
cagccttaca agtcaaaatg cccaagagtc acaaggctat tcaagcagac ggttggatgt    3300
gtcatgcttc caaatgggtc actacttgtg atttccgctg gtacggaccg aagtatataa    3360
cacattccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc tgaagcagcg attgtccagg tgactcctca ccatgtgctt gttgatgaat    3540
acacaggaga atgggttgat tcacagttca tcaacggaaa atgcagcaat gacatatgcc    3600
ccactgtcca taactccaca acctggcatt ccgactataa ggtcaaaggg ctatgtgatt    3660
ctaacctcat ttccatggac atcaccttct tctcagagga cggagagcta tcatccctag    3720
gaaaggaggg cacagggttc agaagtaact actttgctta tgaaactgga gacaaggcct    3780
gcaaaatgca gtactgcaag cgttggggag tcagactccc atcaggtgta tggttcgaga    3840
tggctgataa ggatctcttt gctgcagcca gattccctga atgcccagaa gggtcaagta    3900
tctctgctcc atctcagacc tcagtggatg taagtctcat tcaggacgtt gagaggatct    3960
tggattattc cctctgccaa gaaacctgga gcaaaatcag agcgggtctt cccatctctc    4020
cagtggatct cagctatctt gctcctaaaa acccaggaac cggtcctgtc tttaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggctcc atatgaagac gtggaaattg gacccaatgg agttctgagg accagttcag    4260
gatataagtt tcctttatat atgattggac atggtatgtt ggactccgat cttcatctta    4320
gctcaaaggc tcaggtgttt gaacatcctc acattcaaga cgctgctgcg cagcttcctg    4380
atgatgagac tttattttt ggtgatactg gctatccaa aaatccaatc gagtttgtag    4440
aaggttggtt cagtagttgg aagagctcta ttgcctcttt tttctttatc ataggttaa    4500 tcattggact attcttggtt ctccgagttg gtatttatct ttgcattaaa ttaaagcaca    4560
ccaagaaaag acagatttat acagacatag agatgaaccg acttgggaag taactcaaat    4620
cctgcacaac agattcttca tgtttgaacc aaatcaactt gtgatatcat gctcaaagag    4680
gccttaatta tattttaatt tttaattttt atgaaaaaaa ctaacagcaa tcatggaagt    4740
ccacgatttt gagaccgacg agttcaatga tttcaatgaa gatgactatg ccacaagaga    4800
attcctgaat cccgatgagc gcatgacgta cttgaatcat gctgattaca atttgaattc    4860
tcctctaatt agtgatgata ttgacaattt gatcaggaaa ttcaattctc ttccgattcc    4920
ctcgatgtgg gatagtaaga actgggatgg agttcttgag atgttaacat catgtcaagc    4980 caatccatc tcaacatctc agatgcataa atggatggga agttggttaa tgtctgataa    5040
tcatgatgcc agtcaaggt atagttttt acatgaagtg gacaaagagg cagaaataac    5100
atttgacgtg gtggagacct tcatccgcgg ctggggcaac aaaccaattg aatacatcaa    5160
aaaggaaaga tggactgact cattcaaaat tctcgcttat ttgtgtcaaa agttttggga    5220
cttacacaag ttgacattaa tcttaaatgc tgtctctgag gtggaattgc tcaacttggc    5280
gaggactttc aaaggcaaag tcagaagaag ttctcatgga acgaacatat gcaggcttag    5340
ggttcccagc ttgggtccta cttttatttc agaaggatgg gcttacttca agaaacttga    5400
tattctaatg gaccgaaact ttctgttaat ggtcaaagat gtgattatag ggaggatgca    5460
aacggtgcta tccatggtat gtagaataga caacctgttc tcagagcaag acatcttctc    5520
```

```
ccttctaaat atctacagaa ttggagataa aattgtggag aggcaggaa attttttctta    5580 tgacttgatt aaaatggtgg aaccgatatg caacttgaag ctgatgaaat tagcaagaga    5640
atcaaggcct ttagtcccac aattccctca ttttgaaaat catatcaaga cttctgttga    5700 tgaagggca aaaattgacc gaggtataag attcctccat gatcagataa tgagtgtgaa    5760
aacagtggat ctcacactgg tgatttatgg atcgttcaga cattggggtc atccttttat    5820
agattattac gctggactag aaaaattaca ttcccaagta accatgaaga aagatattga    5880
tgtgtcatat gcaaaagcac ttgcaagtga tttagctcgg attgttctat ttcaacagtt    5940
caatgatcat aaaaagtggt tcgtgaatgg agacttgctc cctcatgatc atccctttaa    6000
aagtcatgtt aaagaaaata catggcccac agctgctcaa gttcaagatt ttggagataa    6060
atggcatgaa cttccgctga ttaaatgttt tgaaataccc gacttactag acccatcgat    6120
aatatactct gacaaaagtc attcaatgaa taggtcagag gtgttgaaac atgtccgaat    6180
gaatccgaac actcctatcc ctagtaaaaa ggtgttgcag actatgttgg acacaaaggc    6240
taccaattgg aaagaattc ttaaagagat tgatgagaag ggcttagatg atgatgatct    6300
aattattggt cttaaaggaa aggagaggga actgaagttg gcaggtagat ttttctccct    6360
aatgtcttgg aaattgcgag aatactttgt aattaccgaa tatttgataa agactcattt    6420
cgtccctatg tttaaaggcc tgacaatggc ggacgatcta actgcagtca ttaaaaagat    6480
gttagattcc tcatccggcc aaggattgaa gtcatatgag gcaatttgca tagccaatca    6540
cattgattac gaaaaatgga ataaccacca aaggaagtta tcaaacggcc cagtgttccg    6600
agttatgggc cagttcttag gttatccatc cttaatcgag agaactcatg aattttttga    6660
gaaaagtctt atatactaca atggaagacc agacttgatg cgtgttcaca acaacacact    6720
gatcaattca acctcccaac gagtttgttg gcaaggacaa gagggtggac tggaaggtct    6780
acggcaaaaa ggatggagta tcctcaatct actggttatt caagagagg ctaaaatcag    6840 aaacactgct gtcaaagtct tggcacaagg tgataatcaa gttatttgca cacagtataa    6900
aacgaagaaa tcgagaaacg ttgtagaatt acagggtgct ctcaatcaaa tggttttctaa    6960 taatgagaaa attatgactg caatcaaaat agggacaggg aagttaggac tttttgataaa    7020 tgacgatgag actatgcaat ctgcagatta cttgaattat ggaaaaatac cgattttccg    7080
tggagtgatt agagggttag agaccaagag atggtcacga gtgacttgtg tcaccaatga    7140
ccaaataccc acttgtgcta atataatgag ctcagtttcc acaaatgctc tcaccgtagc    7200
tcattttgct gagaacccaa tcaatgccat gatacagtac aattattttg ggacatttgc    7260
tagactcttg ttgatgatgc atgatcctgc tcttcgtcaa tcattgtatg aagttcaaga    7320
taagataccg gcttgcaca gttctacttt caaatacgcc atgttgtatt tggacccttc    7380
cattggagga gtgtcgggca tgtctttgtc caggttttg attagagcct cccagatcc    7440 cgtaacagaa agtctctcat tctggagatt catccatgta catgctcgaa gtgagcatct    7500
gaaggagatg agtgcagtat ttggaaaccc cgagatagcc aagtttcgaa taactcacat    7560
agacaagcta gtagaagatc aacctctct gaacatcgct atgggaatga gtccagcgaa    7620
cttgttaaag actgaggtta aaaatgctt aatcgaatca agacaaacca tcaggaacca    7680
ggtgattaag gatgcaacca tatttgta tcatgaagag gatcggctca gaagtttctt    7740
atggtcaata atcctctgt tccctagatt tttaagtgaa ttcaaatcag gcactttttt    7800
gggagtcgca gacgggctca tcagtctatt tcaaaattct cgtactattc ggaactcctt    7860
taagaaaaag tatcataggg aattggatga tttgattgtg aggagtgagg tatcctcttt    7920
```

-continued

```
gacacattta gggaaacttc atttgagaag gggatcatgt aaaatgtgga catgttcagc    7980
tactcatgct gacacattaa gatacaaatc ctggggccgt acagttattg ggacaactgt    8040
accccatcca ttagaaatgt tgggtccaca acatcgaaaa gagactcctt gtgcaccatg    8100
taacacatca gggttcaatt atgtttctgt gcattgtcca gacgggatcc atgacgtctt    8160
tagttcacgg ggaccattgc ctgcttatct agggtctaaa acatctgaat ctacatctat    8220
tttgcagcct tgggaaaggg aaagcaaagt cccactgatt aaaagagcta cacgtcttag    8280
agatgctatc tcttggtttg ttgaacccga ctctaaacta gcaatgacta actttctaa    8340
catccactct ttaacaggcg aagaatggac caaaaggcag catgggttca aaagaacagg    8400
gtctgccctt cataggtttt cgacatctcg gatgagccat ggtgggttcg catctcagag    8460
cactgcagca ttgaccaggt tgatggcaac tacagacacc atgagggatc tgggagatca    8520
gaatttcgac ttttttattcc aggcaacgtt gctctatgct cagattacca ccactgttgc    8580
aagagacgga tggatcacca gttgtacaga tcattatcat attgcctgta agtcctgttt    8640
gagacccata aagagatca ccctggactc aagtatggac tacacgcccc cagatgtatc    8700
ccatgtgctg aagacatgga ggaatgggga aggttcgtgg ggacaagaga taaaacagat    8760
ctatcctttta aagggaatt ggaagaattt agcacctgct gagcaatcct atcaagtcgg    8820
cagatgtata ggttttctat atggagactt ggcgtataga aaatctactc atgccgagga    8880
cagttctcta tttcctctat ctatacaagg tcgtattaga ggtcgaggtt cttaaaagg    8940
gttgctagac ggattaatga gagcaagttg ctgccaagta atacaccgga gaagtctggc    9000
tcatttgaag aggccggcca acgcagtgta cggaggtttg atttacttga ttgataaatt    9060
gagtgtatca cctccattcc tttctcttac tagatcagga cctattagag acgaattaga    9120
aacgattccc cacaagatcc caacctccta tccgacaagc aaccgtgata tgggggtgat    9180
tgtcagaaat tacttcaaat accaatgccg tctaattgaa aagggaaaat acagatcaca    9240
ttattcacaa ttatggttat tctcagatgt cttatccata gacttcattg gaccattctc    9300
tatttccacc accctcttgc aaatcctata caagccattt ttatctggga aagataagaa    9360
tgagttgaga gagctggcaa atctttcttc attgctaaga tcaggagagg ggtgggaaga    9420
catacatgta aaattcttca ccaaggacat attattgtgt ccagaggaaa tcagacatgc    9480
ttgcaagttc gggattgcta aggataataa taaagacatg agctatcccc cttggggaag    9540
ggaatccaga gggacaatta caacaatccc tgtttattat acgaccaccc cttacccaaa    9600
gatgctagag atgcctccaa gaatccaaaa tccctgctg tccggaatca ggttgggcca    9660
gttaccaact ggcgctcatt ataaaattcg gagtatatta catggaatgg gaatccatta    9720
cagggacttc ttgagttgtg gagacggctc cggaggatg actgctgcat tactacgaga    9780
aaatgtgcat agcagaggaa tattcaatag tctgttagaa ttatcagggt cagtcatgcg    9840
aggcgcctct cctgagcccc ccagtgccct agaaacttta ggaggagata aatcgagatg    9900
tgtaaatggt gaaacatgtt gggaatatcc atctgactta tgtgacccaa ggacttggga    9960
ctatttcctc cgactcaaag caggcttggg gcttcaaatt gatttaattg taatggatat   10020
ggaagttcgg gattcttcta ctagcctgaa aattgagacg aatgttagaa attatgtgca   10080
ccggattttg gatgagcaag gagttttaat ctacaagact tatggaacat atatttgtga   10140
gagcgaaaag aatgcagtaa caatccttgg tcccatgttc aagacggtcg acttagttca   10200
aacagaattt agtagttctc aaacgtctga agtatatatg gtatgtaaag gtttgaagaa   10260
attaatcgat gaacccaatc ccgattggtc ttccatcaat gaatcctgga aaaacctgta   10320
```

-continued

```
cgcattccag tcatcagaac aggaatttgc cagagcaaag aaggttagta catactttac   10380
cttgacaggt attccctccc aattcattcc tgatccttt gtgaacattg agactatgct    10440
acaaatattc ggagtaccca cgggtgtgtc tcatgcggct gccttaaaat catctgatag   10500
acctgcagat ttattgacca ttagccttt ttatatggcg attatatcgt attataacat    10560
caatcatatc agagtaggac cgataccctcc gaaccccca tcagatggaa ttgcacaaaa   10620
tgtggggatc gctataactg gtataagctt ttggctgagt ttgatggaga agacattcc    10680 actatatcaa cagtgtttag cagttatcca gcaatcattc ccgattaggt gggaggctgt   10740
ttcagtaaaa ggaggataca agcagaagtg gagtactaga ggtgatgggc tcccaaaaga   10800
tacccgaatt tcagactcct tggccccaat cgggaactgg atcagatctc tggaattggt   10860
ccgaaaccaa gttcgtctga atccattcaa tgagatcttg ttcaatcagc tatgtcgtac   10920
agtggataat catttgaaat ggtcaaattt gcgaaaaaac acaggaatga ttgaatggat   10980 caatagcga atttcaaaag aagaccggtc tatactgatg ttgaagagtg acctacatga    11040
ggaaaactct tggagagatt aaaaaatcat gaggagactc caaactttaa gtatgaaaaa   11100
aactttgatc cttaagaccc tcttgtggtt tttattttt atctggtttt gtggtcttcg    11160
t                                                                   11161
```

<210> SEQ ID NO 5
<211> LENGTH: 690
<212> TYPE: DNA
<213> ORGANISM: Vesicular stomatitis virus

<400> SEQUENCE: 5

```
atgagttcct taaagaagat tctcggtctg aaggggaaag gtaagaaatc taagaaatta    60
gggatcgcac cacccctta tgaagaggac actaacatgg agtatgctcc gagcgctcca    120
attgacaaat cctattttgg agttgacgag agggacactc atgatccgca tcaattaaga    180
tatgagaaat tcttctttac agtgaaaatg acggttagat ctaatcgtcc gttcagaaca    240
tactcagatg tggcagccgc tgtatcccat tgggatcaca tgtacatcgg aatggcaggg    300
aaacgtccct tctacaagat cttggctttt ttgggttctt ctaatctaaa ggccactcca    360
gcggtattgg cagatcaagg tcaaccagag tatcacgctc actgtgaagg cagggcttat    420
ttgccacaca gaatggggaa gaccccctccc atgctcaatg taccagagca cttcagaaga    480
ccattcaata taggtctttta caagggaacg gttgagctca caatgaccat ctacgatgat    540
gagtcactgg aagcagctcc tatgatctgg gatcatttca attcttccaa attttctgat    600
ttcagagaga aggccttaat gtttggcctg attgtcgaga aaaaggcatc tggagcttgg    660
gtcctggatt ctgtcagcca cttcaaatga                                    690
```

<210> SEQ ID NO 6
<211> LENGTH: 229
<212> TYPE: PRT
<213> ORGANISM: Vesicular stomatitis virus

<400> SEQUENCE: 6

```
Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Asn
            20                  25                  30

Met Glu Tyr Ala Pro Ser Ala Pro Ile Asp Lys Ser Tyr Phe Gly Val
        35                  40                  45

Asp Glu Met Asp Thr His Asp Pro His Gln Leu Arg Tyr Glu Lys Phe
```

```
            50                  55                  60
Phe Phe Thr Val Lys Met Thr Val Arg Ser Asn Arg Pro Phe Arg Thr
 65                  70                  75                  80

Tyr Ser Asp Val Ala Ala Val Ser His Trp Asp His Met Tyr Ile
             85                  90                  95

Gly Met Ala Gly Lys Arg Pro Phe Tyr Lys Ile Leu Ala Phe Leu Gly
                100                 105                 110

Ser Ser Asn Leu Lys Ala Thr Pro Ala Val Leu Ala Asp Gln Gly Gln
                115                 120                 125

Pro Glu Tyr His Ala His Cys Glu Gly Arg Ala Tyr Leu Pro His Arg
            130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Val Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
            195                 200                 205

Gly Leu Ile Val Glu Lys Lys Ala Ser Gly Ala Trp Phe Leu Asp Ser
    210                 215                 220

Val Arg His Phe Lys
225
```

<210> SEQ ID NO 7
<211> LENGTH: 41
<212> TYPE: DNA
<213> ORGANISM: Artificial Sequence
<220> FEATURE:
<223> OTHER INFORMATION: PCR primer

<400> SEQUENCE: 7
atcgctcgag aacagatgac tacaaagacg atgacgacaa g        41

<210> SEQ ID NO 8
<211> LENGTH: 45
<212> TYPE: DNA
<213> ORGANISM: Artificial Sequence
<220> FEATURE:
<223> OTHER INFORMATION: PCR primer

<400> SEQUENCE: 8
atcggctagc agttttttc agggatccag ctctaggtgg gctgc        45

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
ttgtgcttct ccactacagc        20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
ctgtaagtct gttaatgaag                                        20

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
tgacactggc aaaacaatgc a                                      21

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
ggtccttttc accagcaagc t                                      21

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
atggttgttt ccgaagtgga c                                      21

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
tttcttcagt ttcagcacca g                                      21

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
atgtctgtta cagtcaagag aatc                                   24

<210> SEQ ID NO 16
<211> LENGTH: 27
<212> TYPE: DNA
<213> ORGANISM: Artificial Sequence
<220> FEATURE:
<223> OTHER INFORMATION: PCR primer

<400> SEQUENCE: 16
tcatttgtca aattctgact tagcata                                27

<210> SEQ ID NO 17
<211> LENGTH: 28
<212> TYPE: DNA
<213> ORGANISM: Artificial Sequence

```
<220> FEATURE:
<223> OTHER INFORMATION: PCR primer

<400> SEQUENCE: 17
tacaccagtg gcaagtgctc caacccag                                          28

<210> SEQ ID NO 18
<211> LENGTH: 28
<212> TYPE: DNA
<213> ORGANISM: Artificial Sequence
<220> FEATURE:
<223> OTHER INFORMATION: PCR primer

<400> SEQUENCE: 18
gtctcgaact cctgacctca agtgatcc                                          28

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
acaatgagct gctggtggct                                                   20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
gatgggcaca gtgtgggtga                                                   20

<210> SEQ ID NO 21
<211> LENGTH: 10
<212> TYPE: PRT
<213> ORGANISM: Artificial Sequence
<220> FEATURE:
<223> OTHER INFORMATION: sequence from a VSV M protein

<400> SEQUENCE: 21

Glu Met Asp Thr His Asp Pro His Gln Leu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: sequence from a VSV M protein

<400> SEQUENCE: 22

Ala Trp Val Leu Asp Ser Val Ser His Phe Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: sequence from a mutant VSV M protein

<400> SEQUENCE: 23

Glu Arg Asp Thr His Asp Pro His Gln Leu
```

1           5               10

<210> SEQ ID NO 24
<211> LENGTH: 10
<212> TYPE: PRT
<213> ORGANISM: Artificial Sequence
<220> FEATURE:
<223> OTHER INFORMATION: sequence from a mutant VSV M protein

<400> SEQUENCE: 24

Glu Ala Asp Thr His Asp Pro His Gln Leu
1               5               10

<210> SEQ ID NO 25
<211> LENGTH: 9
<212> TYPE: PRT
<213> ORGANISM: Artificial Sequence
<220> FEATURE:
<223> OTHER INFORMATION: sequence from a mutant VSV M protein

<400> SEQUENCE: 25

Glu Asp Thr His Asp Pro His Gln Leu
1               5

<210> SEQ ID NO 26
<211> LENGTH: 6
<212> TYPE: PRT
<213> ORGANISM: Artificial Sequence
<220> FEATURE:
<223> OTHER INFORMATION: sequence from a mutant VSV M protein

<400> SEQUENCE: 26

Glu Asp Pro His Gln Leu
1               5

<210> SEQ ID NO 27
<211> LENGTH: 3
<212> TYPE: PRT
<213> ORGANISM: Artificial Sequence
<220> FEATURE:
<223> OTHER INFORMATION: sequence from a mutant VSV M protein

<400> SEQUENCE: 27

Glu Gln Leu
1

<210> SEQ ID NO 28
<211> LENGTH: 11
<212> TYPE: PRT
<213> ORGANISM: Artificial Sequence
<220> FEATURE:
<223> OTHER INFORMATION: mutant VSV M protein

<400> SEQUENCE: 28

Ala Trp Phe Leu Asp Ser Val Arg His Phe Lys
1               5               10

<210> SEQ ID NO 29
<211> LENGTH: 11
<212> TYPE: PRT
<213> ORGANISM: Artificial Sequence
<220> FEATURE:
<223> OTHER INFORMATION: sequence from a mutant VSV M protein

<400> SEQUENCE: 29

Ala Trp Val Leu Asp Ser Val Arg His Phe Lys
1               5               10

```
<210> SEQ ID NO 30
<211> LENGTH: 11
<212> TYPE: PRT
<213> ORGANISM: Artificial Sequence
<220> FEATURE:
<223> OTHER INFORMATION: sequence from a mutant VSV M protein

<400> SEQUENCE: 30

Ala Trp Phe Leu Asp Ser Val Ser His Phe Lys
1               5                   10

<210> SEQ ID NO 31
<211> LENGTH: 5
<212> TYPE: PRT
<213> ORGANISM: Artificial Sequence
<220> FEATURE:
<223> OTHER INFORMATION: sequence from a mutant VSV M protein

<400> SEQUENCE: 31

Ala Trp His Phe Lys
1               5

<210> SEQ ID NO 32
<211> LENGTH: 10
<212> TYPE: PRT
<213> ORGANISM: Artificial Sequence
<220> FEATURE:
<223> OTHER INFORMATION: sequence from a mutant VSV M protein

<400> SEQUENCE: 32

Glu Ala Ala Ala Ala Asp Pro His Gln Leu
1               5                   10
```

MUTANT VIRUSES AND USES THEREOF

REFERENCE TO PRIOR APPLICATIONS

This is a continuation of U.S. patent application No. 10/551,103, filed Oct. 16, 2006, now U.S. Pat. No. 7,731,974, which is a §371 of PCT/CA2004/000460, filed Mar. 29, 2004, which claims the benefit of U.S. Provisional Application No. 60/457,591, filed Mar. 27, 2003, the disclosures of which are incorporated herein by reference in their entireties.

INCORPORATION-BY-REFERENCE OF MATERIAL SUBMITTED IN A SEQUENCE LISTING "TXT" FILE

The material in the text file named "Sequence_listing_18041B-PCTUS_Oct_2008_ST25.txt" created on Oct. 16, 2008, which has a size of 40 kilobytes, is incorporated herein by reference in its entirety.

FIELD OF THE INVENTION

The present invention pertains to the field of viruses and in particular to mutant viruses that are useful as viral vectors and vaccines.

BACKGROUND

Attenuated viruses or those that have reduced replication potential have been widely used for a number of therapeutic applications, for example, as vaccines or vaccine vectors, or as gene therapy vectors. Production of attenuated viruses has typically involved the isolation of chance mutations by repeated passage of wild-type virus through unnatural hosts. Advances in recombinant DNA technology and genetic engineering techniques have provided the tools to better develop viruses as therapeutic and prophylactic agents. Recombinant techniques permit the introduction of specific mutations into a selected region of the viral genome and also minimise the reversion of the mutant virus to wild-type.

The ability of many viruses to stimulate both humoral and cell-mediated immunity makes them ideal vaccine vectors and a number of viruses, therefore, have been developed as vaccine vectors for a wide range of diseases including HIV, HCV and cancer. Viruses are also well suited for use as gene therapy vectors. Gene therapy, i.e. the modification of gene expression by the transient or permanent transfer of functional genes to somatic cells, is being intensively developed as a novel approach for preventing and treating disease. Although a variety of physical and chemical methods are known for introducing exogenous nucleic acids into eukaryotic cells, viruses have generally been proven to be much more efficient for this purpose. Several viruses such as parvoviruses, adenoviruses, herpesviruses, retroviruses, rhabdoviruses and poxviruses, have been explored as possible gene therapy vectors (see, for example, U.S. Pat. Nos. 6,440,422; 6,531,123 and 6,451,323).

The engineering of a number of viruses to produce recombinant viruses with specific properties has been described. For example, U.S. Pat. No. 6,497,873 describes a recombinant Rhabdovirus that expresses the F protein of the Paramyxovirus SV5 strain. In this recombinant virus, the F protein is expressed as a fusion protein with a portion of the Rhabdovirus G protein. U.S. Pat. Nos. 6,022,726 and 6,468,544 describe engineered attenuated viruses that include a mutation in a non-coding or coding sequence of a viral non-structural (NS) gene. Chimeric attenuated viruses which express altered or chimeric viral proteins are also described. U.S. Pat. No. 6,468,544 further describes a live attenuated influenza virus which can induce interferon production in an infected cell.

Engineered viruses have also been described as oncolytic agents, which exploit genetic defects unique to neoplastic cells to replicate in and lyse neoplastic cells, but not non-neoplastic cells. For example, International Patent Applications WO 97/26904 and WO 96/03997 disclose a mutant herpes simplex virus (HSV-1716) that inhibits tumour cell growth, U.S. Pat. No. 6,296,845 describes a mutated adenovirus that is believed to replicate preferentially in p53 negative tumour cells, U.S. Pat. No. 6,110,461 teaches use of a Reovirus for treatment of Ras-mediated neoplasm, and U.S. Pat. No. 6,531,456 describes a recombinant adeno-associated virus vector carrying a drug susceptibility gene and a second gene capable of producing an ancillary effect (such as an interferon or tumour suppressor gene) for use in the treatment of cancer.

As an alternative to genetically engineering viruses, non-pathogenic viruses may be employed, for example, WO 01/19380 describes the use of a Rhabdovirus, and in particular vesicular stomatitis virus (VSV), as a selective oncolytic agent against tumour cells characterized by having low levels of, or no, PKR (double stranded RNA dependent kinase) activity. WO 01/19380 also describes the identification of four mutant VSVs that were susceptible to interferon and their use as oncolytic agents.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide mutant viruses and uses thereof. In accordance with an aspect of the present invention, there is provided a mutant Rhabdovirus having one or more mutation in a gene encoding a protein involved in blocking nuclear transport of mRNA or protein in an infected cell, wherein said mutation results in the mutant Rhabdovirus having a decreased ability to block nuclear transport of mRNA or protein when compared to the wild-type virus.

In accordance with another aspect of the invention, there is provided a viral vector comprising a mutant Rhabdovirus having one or more mutation in a gene encoding a protein involved in blocking nuclear transport of mRNA or protein in an infected cell, wherein said mutation results in the mutant Rhabdovirus having a decreased ability to block nuclear transport of mRNA or protein when compared to the wild-type virus.

In accordance with another aspect of the invention, there is provided a vaccine vector comprising a mutant Rhabdovirus having one or more mutation in a gene encoding a protein involved in blocking nuclear transport of mRNA or protein in an infected cell and a heterologous nucleic acid encoding one or more antigen, wherein said mutation results in the mutant Rhabdovirus having a decreased ability to block nuclear transport of mRNA or protein when compared to the wild-type virus.

In accordance with a further aspect of the invention, there is provided a vaccine adjuvant comprising a mutant Rhabdovirus having one or more mutation in a gene encoding a protein involved in blocking nuclear transport of mRNA or protein in an infected cell and optionally a pharmaceutically acceptable carrier, said mutant Rhabdovirus being capable of triggering the production of one or more cytokine in an infected cell, wherein said mutation results in the mutant Rhabdovirus having a decreased ability to block nuclear transport of mRNA or protein when compared to the wild-type virus.

In accordance with another aspect of the invention, there is provided a selective oncolytic agent comprising a mutant Rhabdovirus having one or more mutation in a gene encoding a protein involved in blocking nuclear transport of mRNA or protein in an infected cell and optionally a pharmaceutically acceptable carrier, wherein said mutation results in the mutant Rhabdovirus having a decreased ability to block nuclear transport of mRNA or protein when compared to the wild-type virus.

In accordance with a further aspect of the invention, there is provided a pharmaceutical composition comprising a mutant Rhabdovirus having one or more mutation in a gene encoding a protein involved in blocking nuclear transport of mRNA or protein in an infected cell and a pharmaceutically acceptable carrier, wherein said mutation results in the mutant Rhabdovirus having a decreased ability to block nuclear transport of mRNA or protein when compared to the wild-type virus.

In accordance with another aspect of the invention, there is provided an immunogenic composition comprising a mutant Rhabdovirus having one or more mutation in a gene encoding a protein involved in blocking nuclear transport of mRNA or protein in an infected cell and a pharmaceutically acceptable carrier, said mutant Rhabdovirus being capable of triggering the production of one or more cytokine in an infected cell, wherein said mutation results in the mutant Rhabdovirus having a decreased ability to block nuclear transport of mRNA or protein when compared to the wild-type virus.

In accordance with a further aspect of the invention, there is provided a use of the mutant Rhabdovirus as described above as an additive for pharmaceutical preparations of viruses to protect against virulent revertants arising in the preparation.

In accordance with another aspect of the invention, there is provided a use of the mutant Rhabdovirus as described above in the treatment of a disease or disorder that can be alleviated by cytokine release.

In accordance with a further aspect of the invention, there is provided a use of the mutant Rhabdovirus as described above as a viral vector for delivery of said heterologous nucleic acid to a subject in need thereof.

In accordance with another aspect of the invention, there is provided a kit comprising one or more containers and a mutant Rhabdovirus having one or more mutation in a gene encoding a protein involved in blocking nuclear transport of mRNA or protein in an infected cell, wherein said mutation results in the mutant Rhabdovirus having a decreased ability to block nuclear transport of mRNA or protein when compared to the wild-type virus.

BRIEF DESCRIPTION OF THE FIGURES

FIG. 1 depicts that the decreased in vivo toxicity of mutant VSV viruses AV1 and AV2 is mediated by interferon. (A) Human prostate carcinoma cells (PC3) and human renal carcinomas cells (CAM-1) were either mock infected or infected with wild-type (WT), AV1 or AV2 strains of VSV. Culture media were assayed by ELISA to detect human IFN-α production 18 hours post-infection. (B) In vivo toxicity of WT versus mutant VSV strains by route and mouse strain. IN=intranasal; IV=intravenous; nd=not determined. (C) AV2 can protect mice in trans against lethal WT VSV infection. $PKR^{-/-}$ mice were infected intranasally at various doses with either WT, AV2 or combinations of both strains and monitored for morbidity or mortality. Values denote number of mice per group showing signs of infection (morbidity) or number of mice per group which succumbed to the infection (mortality). (D) Balb/C and Balb/C $IFNR^{-/-}$ mice were infected intranasally with WT VSV, AV1 or AV2 virus and monitored for morbidity.

FIG. 2 depicts that the secondary transcriptional response is inhibited by WT VSV but not AV1 or AV2. (A) Primary response to viral infection is mediated by IRF-3, cJUN/ATF-2, and NFκB (shown here forming part of the enhansosome complex at the IFN-β promoter). Microarrray data indicates primary transcriptional response genes robustly upregulated in both WT and mutant virus infected cells. (a: ISG15 is known to require ISGF3 for full induction). Values represent fold induction over mock infected. (B) IFN-β is then translated and secreted to stimulate, in an autocrine fashion, JAK/STAT signalling to form ISGF3 complexes in the nucleus, which mediates the induction of genes of the secondary transcriptional response. While cells infected with AV1 or AV2 show robust upregulation of these genes, WT infected cells show no expression at all (A=absent). (C) Without the consequent expression of IRF-7 in cells infected with WT VSV the tertiary transcriptional wave, which includes almost all IFN-α genes, cannot take place (b: IFN-α7 is marginally detected by the array in WT samples). In contrast, AV1 and AV2 infected cells efficiently induce the expression of IFN-α genes. (D) RT-PCR data at 4 hours post infection of A549 cells showed primary response genes RANTES and IFN-β induced to similar levels in WT and mutant VSV infected cells, while upregulation of MX1 (secondary response) was impaired in WT infected cells. (E) Western blot analysis showed similar kinetics of IRF-3 activation between WT and mutant VSVs, however, ISG56 (primary response) protein expression was severely impaired in WT infected cells. IRF-7 protein is detected only in AV1 and AV2 infected cells. IRF-7Δ appears to be able to induce the expression of endogenous IRF-7.

FIG. 4 depicts that the mutant VSV strains demonstrate in vivo efficacy in a variety of tumour models. (A) Mutant VSV is effective in treating xenograft human ovarian ascites tumours by intraperitoneal treatment. Human ES-2 ovarian carcinoma cells were injected into the intraperitoneal cavity of CD-1 nude mice to establish ascites tumours. Twelve days after injection of $1\times10^6$ ES-2 cells, animals were treated every other day (3 doses total) with either AV2 VSV or UV inactivated AV2 VSV. Each dose ($1\times10^9$ pfu) was administered into the intraperitoneal cavity Animals were assessed for morbidity and mortality and were euthanized following the appearance of moderate ascites formation. "n" denotes number of animals per group. (B) Systemic treatment of subcutanenous tumours in an immune competent animal. Subcutaneous tumours were established in Balb/C mice by injecting $1\times10^6$ CT26 colon carcinoma cells into the hind flank region. When tumours reached approximately 10 mm³, mice were treated every other day for 10 days (6 doses total) with an intravenous injection of 5×10⁸ pfu of the indicated virus. "Trojan" refers to the injection of 3×10⁵ CT26 cells infected with AV1 VSV at an MOI of 20. Control mice received 6 doses of 5×10⁸ pfu equivalents of UV inactivated AV2 VSV. Tumours were measured daily to calculate tumour volumes Animals were euthanized when their tumours burden was deemed excessive (approximately 750 mm³) (C) Shows the change in mouse weights measured daily, for each group, for the 3 days before treatment, to day 11 post treatment. Error bars denote SEM. (D) Treatment of disseminated lung tumours in an immune-competent mouse model. Lung tumours are established injecting 3×10⁵ CT26 cells into the tail vein of Balb/C mice. On day 12, mice were treated as follows: UV AV2 IV=1 dose intravenously (5×10⁸ pfu equivalents), AV2 IV=1 dose of mutant 3 VSV intravenously (5×10⁸ pfu), AV2 IN=1 dose of AV2 VSV intransally (5×10⁷ pfu), AV2 IV & IN=1 dose of AV2 VSV intravenously (5×10⁸ pfu) and 1 dose of AV2 VSV intransally (5×10⁷ pfu). Four days after treatment all mice were sacrificed and their lungs were removed (hearts are visible for scale). Arrows indicate residual tumours. (E) Lung tumours were established as described above. On day 12, mice are treated as indicated with 5×10⁷ pfu delivered by intranasal instillation, every other day for 2 weeks (6 doses total). Morbidity and mortality are monitored daily, and mice which show signs of respiratory distress are euthanized and their examined for tumour burden. "n" denotes number of mice in treatment group.

FIG. 5 presents a model depicting how mutant VSV strains may be able to prevent the emergence of virulent WT strains from a mixed population. (A) WT VSV can block IFN secretion from infected cells rendering neighbouring cells unprotected and susceptible to nascent viral particles, which results in viral spread. (B) A "Cytokine cloud" of IFNs, and perhaps other cytokines, is induced following infection with VSV strains coding for M proteins defective in blocking nuclear/cytoplasmic transport. The neighbouring cells are protected from infection by mutant VSV and any putative revertant strains attempting to emerge from the population.

FIGS. 10A, B and C depicts images of a live cell co-transfected with the amino terminal 72 amino acids of VSV M fused to GFP (WT+72-GFP-N1, green) and OCT-DsRed2 (mitochondrial marker, red). Merged images indicate co-localisation as well as the progressive fragmentation of the initially reticular mitochondria in this cell as the cell is killed by this toxic protein. D A live cell co-transfected as above. Again this indicates the co-localisation of WT+72-GFP-N1 and OCT-DsRed2 with relative concentration of the VSV M-GFP fusion protein and bulges and junctions in the mitochondria (green).

FIG. 11 depicts the nucleic acid sequence for the genome of the VSV mutant AV1 [SEQ ID NO:1].

FIG. 12 depicts the nucleic acid sequence for the mutant M protein gene of the VSV mutant AV1 [SEQ ID NO:2].

FIG. 13 depicts the amino acid sequence for the mutant M protein of the VSV mutant AV1 [SEQ ID NO:3].

FIG. 14 depicts the nucleic acid sequence for the genome of the VSV mutant AV2 [SEQ ID NO:4].

FIG. 15 depicts the nucleic acid sequence for the mutant M protein gene of the VSV mutant AV2 [SEQ ID NO:5].

FIG. 16 depicts the amino acid sequence for the mutant M protein of the VSV mutant AV2 [SEQ ID NO:6].

FIGS. 17A and B graphically demonstrate the protective effect of a mutant VSV according to one embodiment of the present invention, wherein FIG. 17A depicts percent survival of mice following administration of a lethal intracranial dose of VSV; and FIG. 17B depicts changes in mouse weights over time following administration of the lethal intracranial dose of VSV.

FIGS. 19A and B graphically depicts anti-CT26 cytotoxic T lymphocyte activity from splenocytes obtained from WT VSV and ΔM51 VSV treated mice having established CT26 tumours (FIG. 19A) and NK-dependent and -independent CT26 cell lysis caused by splenocytes obtained from non-tumour bearing mice treated with WT VSV and ΔM51 VSV (FIG. 19B).

DETAILED DESCRIPTION OF THE INVENTION

Figure 3:
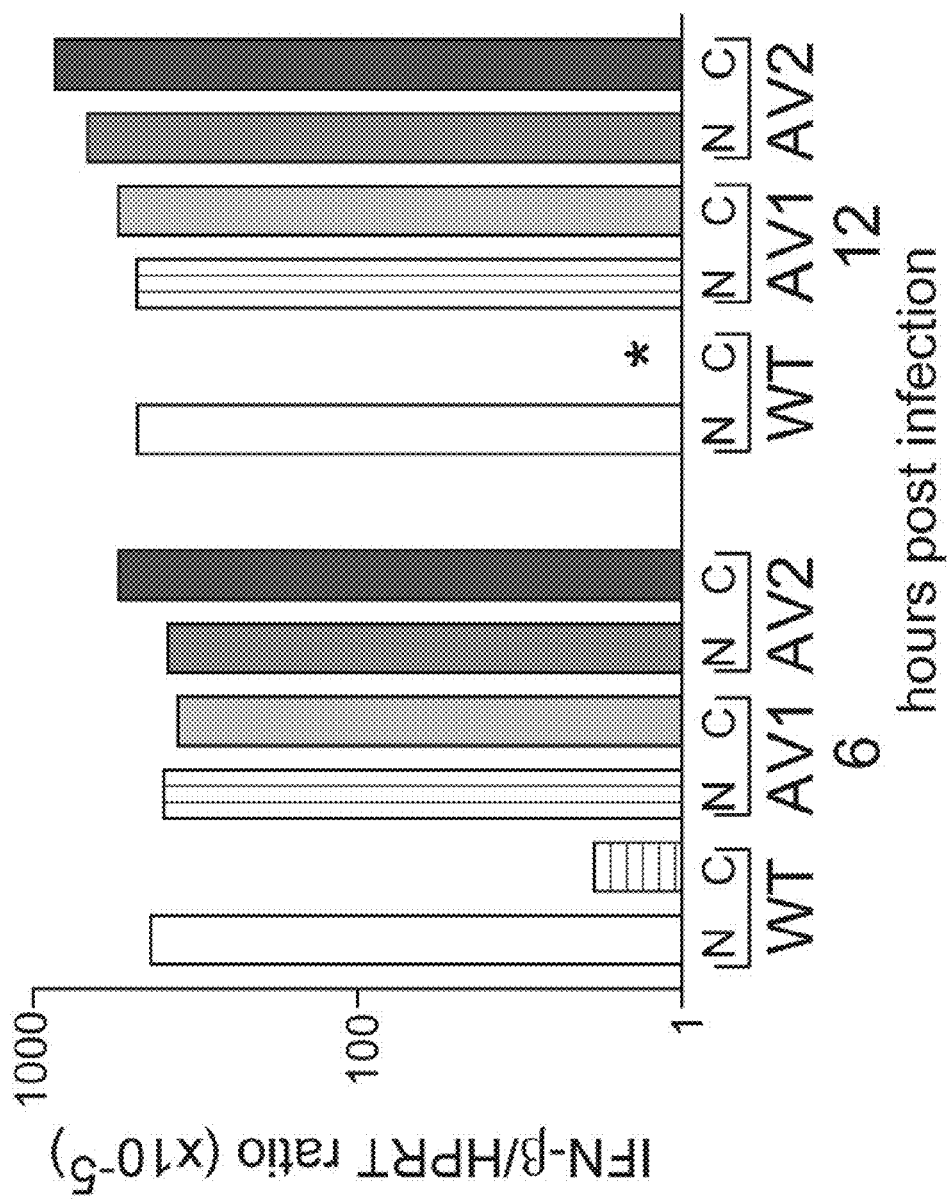
FIG. 3 shows that IFN-β mRNAs are severely depleted in cytoplasmic fractions from WT VSV infected cells as determined by quantitative RT-PCR. (A) Nuclear (N) and cytoplasmic (C) total RNA fractions from cells infected with WT, AV1 or AV2 VSV were assayed for IFN-β mRNA; normalized to HPRT mRNA from the same sample. * indicated no IFN-β mRNA detected. (B) Cells infected with either WT or mutant VSV strains were assayed by ELISA for IFN-β production. AV1 and AV2 infected cells and not WT VSV infected cell show detectable secreted IFN-β.

The present invention provides mutant viruses carrying one or more mutation in a gene encoding a protein responsible for blocking nuclear transport of mRNA or protein in an infected cell. The mutant viruses thus have a decreased ability to block nuclear transport when compared to the wild-type virus and are attenuated in vivo. The mutant viruses may be capable of triggering the anti-viral systems of a normal host cell while remaining sensitive to the effects of these systems. The mutant viruses are suitable for a broad range of applications including, but not limited to, therapeutics for the treatment of cancer and chronic infections, as vaccines and adjuvants, as viral vectors, and as oncolytic and cytolytic agents for the selective lysis of malignant or infected cells.

Definitions

Unless defined otherwise, all technical and scientific terms used herein have the same meaning as commonly understood by one of ordinary skill in the art to which this invention pertains. Standard three- and one-letter notations for amino acids are used interchangeably herein.

The term "heterologous nucleic acid sequence," as used herein in relation to a specific virus, refers to a nucleic acid sequence that originates from a source other than the specified virus.

The term "mutation," as used herein, refers to a deletion, an insertion of heterologous nucleic acid, an inversion or a substitution.

The term "gene," as used herein, refers to a segment of nucleic acid that encodes an individual protein or RNA (also referred to as a "coding sequence" or "coding region") together with associated regulatory regions such as promoters, operators, terminators and the like, that may be located upstream or downstream of the coding sequence.

The term "mutant virus," as used herein, refers to a virus comprising one or more mutations in its genome, including but not limited to deletions, insertions of heterologous nucleic acids, inversions, substitutions, or combinations thereof.

The term "naturally-occurring," as used herein, with reference to a virus indicates that the virus can be found in nature, i.e. it can be isolated from a source in nature and has not been intentionally modified by man in the laboratory.

The term "wild-type virus," as used herein, refers to the most frequent genotype of a virus found in nature and against which mutants are defined.

The term "anti-viral systems," as used herein, refers to the components of a cell's response to viral infection and include, for example, interferons and other cytokines, nitric oxide synthase, double stranded RNA dependent kinase (PKR), oligoadenylate synthase (OAS), Mx A and Mx B GTPases, and the like.

The term "anti-viral response," as used herein, refers to a cell's response to viral infection and includes, for example, production of interferons, cytokine release, production of chemokines, production of lymphokines, or a combination thereof.

The term "normal host cell," as used herein, refers to a non-cancerous, non-infected cell with an intact anti-viral response.

The term "vaccine," as used herein, refers to a preparation of material capable of stimulating an immune response in an animal without inducing disease.

The term "oncolytic agent," as used herein, refers to an agent capable of inhibiting the growth of and/or killing tumour cells.

The term "adjuvant," as used herein, refers to a substance which, when added to a vaccine, is capable of enhancing the immune response stimulated by the vaccine in a subject.

Mutant Viruses

The present invention provides mutant viruses comprising one or more mutation in a gene which encodes a protein that is involved in blocking nuclear transport of mRNA or protein in an infected host cell. As a result, the mutant viruses have a reduced ability to block nuclear transport and are attenuated in vivo. Blocking nuclear export of mRNA or protein cripples the anti-viral systems within the infected cell, as well as the mechanism by which the infected cell can protect surrounding cells from infection (i.e. the early warning system), and ultimately leads to cytolysis. In one embodiment of the present invention, therefore, the mutant viruses have decreased cytolytic properties compared to their wild-type counterpart.

Since the mutant virus is unable to block nuclear transport of mRNA or protein, infection of a normal host cell by the mutant virus can result in the triggering of the anti-viral systems of the cell, which are normally blocked or bypassed by the wild-type virus. In accordance with another embodiment of the present invention, therefore, the mutant virus is capable of triggering, and is sensitive to, the anti-viral systems of a normal host cell.

A variety of viruses that block nuclear transport of mRNA or protein in an infected cell as part of their replicative cycle are known and are thus suitable for mutation in order to produce a mutant virus in accordance with the present invention. The virus can be a DNA virus, a positive-strand RNA virus, or a negative-strand RNA virus. Examples of suitable DNA viruses include Herpesvirus, Adenovirus, Parvovirus, Papovavirus, Iridovirus, Hepadenavirus, Poxvirus, mumps virus, human parainfluenza virus, measles virus or rubella virus. Examples of suitable positive-sense RNA viruses include Togavirus, Flavivirus, Picornavirus, or Coronavirus. Examples of suitable negative-sense RNA viruses include those from the families Orthomyxoviridae, Rhabdoviridae and Paramyxoviridae.

In one embodiment of the present invention, the virus is selected from the families Poxyiridae, Picornaviridae, Orthomyxoviridae or Rhabdoviridae, for example, the virus can be a vaccinia virus, poliovirus, rhinovirus, influenza virus, rabies virus, vesicular stomatitis virus, Newcastle disease virus or vesiculovirus.

In another embodiment of the present invention, the virus is a member of the Rhabdoviridae. Rhabdoviruses are particularly well-suited for therapeutic use as they are not common human pathogens. A pre-existing immune response to a viral strain similar to the one used as a therapeutic agent may attenuate the effectiveness of the mutant virus as therapeutic agent and is, therefore, undesirable. In addition, Rhabdoviruses are RNA viruses that spend their entire lifecycle in the cytoplasm, thus minimising the danger of unwanted integration into the genome of a patient.

In another embodiment of the present invention, the Rhabdovirus is a vesiculovirus. Examples of suitable vesiculoviruses include, but are not limited to, Piry, Chandipura and vesicular stomatitis virus (VSV).

VSV is a member of the Vesiculoviridae that has demonstrated therapeutic potential. VSV infections in humans are either asymptomatic or manifest as a mild "flu." There have been no reported cases of severe illness or death among VSV-infected humans. Other useful characteristics of VSV include the fact that it replicates quickly and can be readily concentrated to high titres, it is a simple virus comprising only five genes and is thus readily amenable to genetic manipulation, and it has a broad host range and is capable of infecting most types of human cells. In one embodiment of the present invention, the mutant virus is a mutant VSV. A number of different strains of VSV are known in the art and are suitable for use in the present invention. Examples include, but are not limited to, the Indiana and New Jersey strains. A worker skilled in the art will appreciate that new strains of VSV will emerge and/or be discovered in the future which are also suitable for use in the present invention. Such strains are also considered to fall within the scope of the invention.

1. Preparation of Mutant Viruses

In accordance with the present invention, the mutant viruses can be naturally-occurring mutants or they may be genetically engineered mutants. The mutant viruses, therefore, can be obtained by selection using defined growth conditions or selection pressures, or they can be recombinant viruses that have been specifically engineered using genetic engineering techniques known in the art.

For example, for selection of those mutant viruses that trigger and remain sensitive to anti-viral systems in an infected cell, a population of the virus can be grown on cells which are normally susceptible to infection by the wild-type virus and those viruses that grow poorly (i.e. form smaller plaques) on these cells are isolated. These isolated viruses are candidate mutant viruses. An example of such a selection technique for viruses such as VSV, which normally block the interferon response in infected cells, would be selection for poor growth on interferon responsive cells, such as epithelial cell lines, when compared to wild-type virus. Formation of large plaques when these candidate mutants are grown on interferon non-responsive cells (such as tumour cells) would confirm that the poor growth is due to the interferon response (see, for example, International Patent Application WO 01/19380).

Once a naturally-occurring mutant virus has been identified and isolated, the position of mutation(s) in the viral genome can be determined using standard techniques, for example, sequencing techniques, restriction analysis, hybridisation techniques, microarray analysis, or combinations of these techniques. A recombinant mutant virus can then be genetically engineered using standard techniques (see below) to contain either identical mutation(s), or similar mutation(s) in the same region of the genome. Viruses that have been genetically engineered (i.e. recombinant viruses) to contain deletion or insertion mutations typically have a lower reversion rate than naturally-occurring mutants and are, therefore, particularly well-suited for therapeutic purposes.

Alternatively, if a candidate gene has already been identified in a virus, recombinant mutant viruses can be genetically engineered using techniques well known in the art (see, for example, Sambrook et al., 1989, A Laboratory Manual. New York: Cold Spring Harbor Laboratory Press). A candidate gene in this regard would be a gene suspected of encoding a protein that is involved in blocking nuclear transport of mRNA or protein in an infected cell. In one embodiment of the present invention, the mutant virus is a recombinant mutant virus.

For example, DNA viruses (e.g., vaccinia, adenoviruses, baculovirus) and positive strand RNA viruses (e.g., poliovirus) can be engineered using recombinant DNA techniques such as those described in U.S. Pat. No. 4,769,330; U.S. Pat. No. 4,215,051 and by Racaniello et al. (1981, Science 214: 916-919). Negative strand RNA viruses (e.g., influenza and VSV) can be genetically engineered using well-established "reverse genetics" techniques, such as the reverse genetics system that has been established for VSV (Roberts A. and J. K. Rose, Virology, 1998, 247: 1-6).

Genetic techniques, such as those described above, can thus be utilised to engineer one or more mutation in a candidate gene. A worker skilled in the art will appreciate that the gene may encode a structural or non-structural protein, depending on the particular virus being used. The mutation can be a nucleotide deletion, insertion, inversion, or substitution of one or more nucleotide, or an insertion of a heterologous nucleic acid, or a combination thereof. As is known in the art, mutant viruses are sometimes capable of reversion to wild-type by correction of the introduced mutation. Mutations that are difficult to correct, such as deletions and/or multiple-nucleotide mutations, therefore, can be used to create mutant viruses in order to minimise reversion. In one embodiment of the present invention, the introduced mutation is a deletion. In another embodiment, the introduced mutation is a mutation involving two, three or more nucleotides. It is well known in the art that protein expression can be affected by mutations in either the coding region of a gene or the regulatory regions associated therewith. Mutations in a non-coding region or a coding region of a candidate gene, or combinations thereof, are encompassed by the present invention. In one embodiment, one or more mutation is engineered into the coding region of a gene. In another embodiment, one or more mutation is engineered into the coding region of a gene that encodes a non-structural protein.

An example of a suitable gene encoding a non-structural protein is the gene encoding the matrix, or M, protein of Rhabdoviruses. The M protein from VSV has been well studied and has been shown to be a multifunctional protein required for several key viral functions including: budding (Jayakar, et al. 2000, J Virol, 74(21): 9818-27), virion assembly (Newcomb, et al. 1982, J Virol, 41(3): 1055-62), cytopathic effect (Blondel, et al. 1990, J Virol, 64(4): 1716-25), and inhibition of host gene expression (Lyles, et al. 1996, Virology 225(1): 172-80). The latter property has been shown herein to be due to inhibition of the nuclear transport of both proteins and mRNAs into and out of the host nucleus. Examples of suitable mutations that can be made in the gene encoding the VSV M protein include, but are not limited to, insertions of heterologous nucleic acids into the coding region, deletions of one or more nucleotide in the coding region, or mutations that result in the substitution or deletion of one or more of the amino acid residues at positions 33, 51, 52, 53, 54, 221, 226 of the M protein, or a combination thereof.

The amino terminus of VSV M protein has been shown to target the protein to the mitochondria, which may contribute to the cytotoxicity of the protein. A mutation introduced into this region of the protein, therefore, could result in increased or decreased virus toxicity. Examples of suitable mutations that can be made in the region of the M protein gene encoding the N-terminus of the protein include, but are not limited to, those that result in one or more deletion, insertion or substitution in the first (N-terminal) 72 amino acids of the protein.

The amino acid numbers referred to above describe positions in the M protein of the Indiana strain of VSV. It will be readily apparent to one skilled in the art that the amino acid sequence of M proteins from other VSV strains and Rhabdoviridae may be slightly different to that of the Indiana VSV M protein due to the presence or absence of some amino acids resulting in slightly different numbering of corresponding amino acids. Alignments of the relevant protein sequences with the Indiana VSV M protein sequence in order to identify suitable amino acids for mutation that correspond to those described herein can be readily carried out by a worker skilled in the art using standard techniques and software (such as the BLASTX program available at the National Center for Biotechnology Information website). The amino acids thus identified are candidates for mutation in accordance with the present invention.

Figure 6:
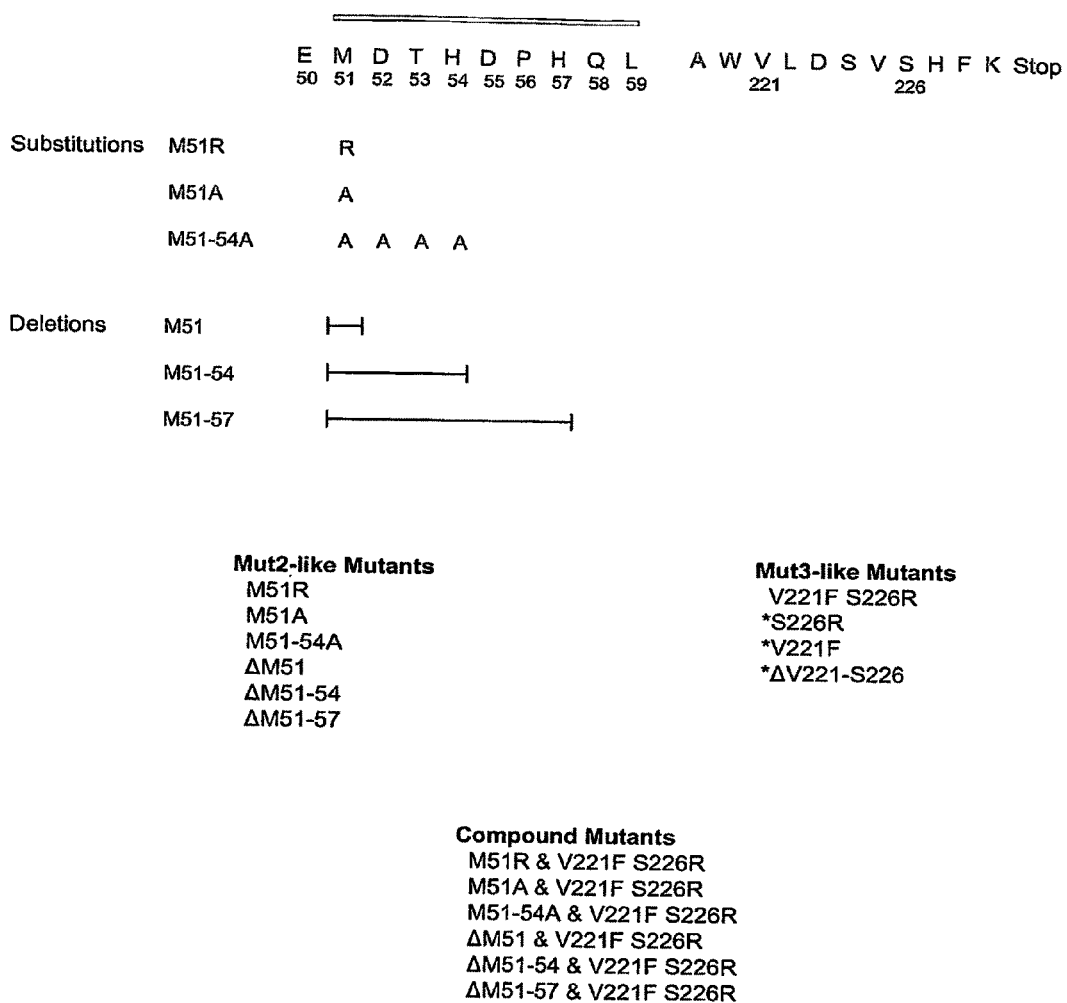
FIG. 6 depicts examples of mutations that can be made in accordance with the present invention in the gene encoding the M protein of VSV. (SEQ ID NO: 21-32)

In one embodiment of the present invention, the mutant virus is a VSV with one or more of the following mutations introduced into the gene encoding the M protein (notation is: wild-type amino acid/amino acid position/mutant amino acid; the symbol Δ indicates a deletion and X indicates any amino acid): M51R, M51A, M51-54A, ΔM51, ΔM51-54, ΔM51-57, V221F, S226R, ΔV221-S226, M51X, V221X, S226X, or combinations thereof. In another embodiment, the mutant virus is a VSV with one of the following combinations of mutations introduced into the gene encoding the M protein: double mutations—M51R and V221F; M51A and V221F; M51-54A and V221F; ΔM51 and V221F; ΔM51-54 and V221F; ΔM51-57 and V221F; M51R and S226R; M51A and S226R; M51-54A and S226R; ΔM51 and S226R; ΔM51-54 and S226R; ΔM51-57 and S226R; triple mutations—M51R, V221F and S226R; M51A, V221F and S226R; M51-54A, V221F and S226R; ΔM51, V221F and S226R; ΔM51-54, V221F and S226R; ΔM51-57, V221F and S226R. Examples of mutant M proteins are depicted in FIG. 6.

The present invention is also directed to isolated nucleic acid molecules (DNA or RNA) having a sequence of the mutant virus, or a fragment thereof, and sequences complementary thereto. Such sequences are useful in the generation of recombinant mutant viruses, or as primers or probes. In one embodiment, isolated nucleic acid molecules are provided having a sequence of a mutant VSV, fragments thereof and sequences complementary thereto. In another embodiment, isolated nucleic acid molecules are provided having a sequence of a VSV with one or more mutation in the M protein, fragments thereof and sequences complementary thereto.

2. Testing Mutant Viruses

In accordance with the present invention, the mutant viruses are characterised by a decreased ability to block nuclear mRNA or protein transport when compared to the wild-type virus. Loss of this ability may result in the mutant viruses exhibiting decreased cytolytic activity and/or in the mutant viruses triggering the anti-viral systems of the cell, which are normally blocked by the wild-type virus.

2.1 In Vitro Testing

Candidate mutant viruses can be screened in vitro for a decrease in, or the loss of, their ability to block nuclear mRNA or protein transport. For example, an appropriate cell line can be infected with a candidate mutant virus, the cells can be harvested and nuclear and cytoplasmic fractions isolated. mRNA can be isolated from each of these fractions and assayed using techniques well known in the art, for example, by RT-PCR, Northern blot or microarray analysis. The mRNA content of the nuclear and cytoplasmic fractions can then be compared with suitable controls, such as the mRNA content of analogous fractions for cells infected with wild-type virus and/or for mock-infected cells.

Alternatively, in situ hybridisation assays can be used to test candidate mutant viruses. Such assays can be set up using one or more target mRNAs that either intrinsically have, or can be engineered to have, short half-lives. In situ hybridisation is then employed to detect these target mRNAs in cells previously infected with a candidate mutant virus. Detection of the target mRNA(s) in the cytoplasm after infection indicates a diminished ability of the candidate virus to block mRNA export out of the nucleus when compared to uninfected controls, and/or controls infected with a wild-type virus. This type of assay can be readily adapted for high-throughput screening by those skilled in the art.

Similarly, assays to test candidate mutants can be set up using a cell line that has been engineered by standard techniques to express a fluorescent protein encoded by a mRNA that has a short half-life. Cells from this engineered cell line are then separately infected with wild-type virus and a candidate mutant virus and monitored for fluorescence using established techniques. In those cells infected with wild-type virus, fluorescence will be lost due to the block by the virus of nuclear cytoplasmic transport of the nascent mRNA coding for the fluorescent protein. Mutant viruses which have a diminished ability to block mRNA transport, on the other hand, will fluoresce for a longer period of time. This type of assay also can be readily adapted for high-throughput screening by those skilled in the art.

In cells that are infected with a mutant virus, more of a particular reference mRNA will be detected in the cytoplasm than is detected in the cytoplasm of cells infected with the wild-type virus. In accordance with the present invention, infection of a cell with a mutant virus results in at least a 20-fold increase in the amount of a reference mRNA in the cytoplasm of the cell compared to the amount in the cytoplasm of a cell infected with the wild-type virus. In one embodiment, infection of a cell with a mutant virus results in at least a 50-fold increase in the amount of a reference mRNA in the cytoplasm of the cell. In other embodiments, the increase is 100-fold, 250-fold, 500-fold or at least 1000-fold.

As indicated above, the mutant viruses may trigger anti-viral systems in an infected cell that are normally blocked or bypassed by the wild-type virus. Candidate mutant viruses can, therefore, also be screened based on their poor growth on cells with intact anti-viral systems when compared to wild-type virus. The mutant viruses should be able to grow as well as wild-type virus on cells deficient in one or more components of the anti-viral response. For example, mutant viruses that trigger the interferon system would grow poorly on interferon-responsive cells, but would grow as well as the wild-type virus on cells in which the interferon response has been disabled, such as tumour cells. The ability of the mutant viruses to trigger anti-viral systems in cells can also be determined by analysing the expression of those genes encoding components of the anti-viral response in infected cells by standard techniques, for example by Western blot or Northern analysis, or by microarray analysis, and comparing levels of expression to appropriate controls.

Mutant viruses that trigger an anti-viral response may also be able to protect neighbouring cells against infection by the wild-type virus. This ability can be tested by co-infection experiments using the mutant and wild-type viruses with cells that are normally susceptible to infection by the wild-type virus and determining the growth of the wild-type virus on the co-infected cells. Methods of conducting co-infection experiments are known in the art.

2.2 In Vivo Testing

Once appropriate mutant viruses have been identified, suitable animal models can be used to evaluate the efficacy and toxicity of the mutant viruses using standard techniques known in the art.

For example, toxicity can be determined by conducting $LD_{50}$ tests. In one embodiment of the present invention, the mutant virus has a $LD_{50}$ between about 10 and about 10,000 fold greater than that of the wild-type virus. Alternatively, appropriate animal models can be treated with varying concentrations of the mutant virus and the toxic effects of the virus can then be evaluated over an appropriate time period by monitoring the general health and body weight of the animals. After the completion of the period of assessment, the animals can be sacrificed and the appearance and weight of the relevant organs determined. Examples of suitable animal models include, but are not limited to, Balb/C mice and CD-1 mice. Other suitable animal models include those that are particularly susceptible to infection by a wild-type virus, such as those that are defective in a component of the anti-viral response. An example would be PKR−/− mice, which have been shown to be exquisitely susceptible to VSV infection.

The ability of the mutant viruses to trigger an anti-viral response can be tested in vivo using standard techniques. For example, animals can be treated with the mutant virus and subsequently challenged with the wild-type virus or a second virus. The survival of these animals can be compared to a control group that did not receive prior treatment with the mutant virus.

As indicated above, mutant viruses that trigger an immune response may also be able to protect a subject against simultaneous co-infection by the wild-type virus. To evaluate this protective effect of the mutant virus, the anti-viral response and toxicity profile can be determined for animals co-infected with wild-type and mutant virus and can be compared to animals infected with wild-type virus alone.

Uses

It will be readily apparent to a worker skilled in the art that the mutant viruses of the present invention are useful in a broad range of applications. Non-limiting examples are provided below.

1. Viral Vectors

The present invention provides for the use of the mutant viruses of the invention as viral vectors. When used as viral vectors, the mutant viruses are engineered to incorporate at least one heterologous nucleic acid sequence encoding a therapeutically active molecule. The viral vector can be used to infect cells, which then express the therapeutically active molecule encoded by the heterologous nucleic acid sequence. Viral vectors can thus be used to deliver the heterologous nucleic acid to the cells of a subject for in vivo expression of the therapeutically active molecule.

The heterologous nucleic acid sequence incorporated into the viral vector can be derived from genomic DNA, cDNA, or RNA, for example, through the use of standard cloning and/or nucleic acid amplification techniques, or it can be chemically synthesised by methods known in the art. The nucleic acid sequence can be inserted into a non-essential region or gene in the genome of the virus or into a gene encoding a protein involved in blocking nuclear mRNA or protein transport using methods known in the art and described herein and elsewhere.

For the purposes of the present invention, the therapeutically active molecule encoded by the heterologous nucleic acid sequence can, for example, be a protein that, when expressed in a cell, supplements or supplies an activity that is deficient in the cell, thus enabling the cell to combat a pathological condition. Such proteins include, but are not limited to, enzymes, blood derivatives, hormones, lymphokines, growth factors, neurotransmitters, trophic factors, apolipoproteins, and tumour-suppressing genes, viral or tumour specific antigens or antigenic epitopes, immune modulators, interferon regulatory factors, cytokines and suicide genes. Those skilled in the art will understand that the inserted heterologous DNA/RNA may further include promoters, enhancers, terminators, polyadenylation signals, internal ribosomal entry sites, and other regulatory elements required for efficient expression of a gene encoded by the DNA or RNA. Alternatively, expression of the heterologous nucleic acid may be dependent, in whole or in part, on endogenous regulatory sequences of the viral vector.

The present invention also contemplates heterologous nucleic acid sequences that encode antisense oligonucleotides, ribozymes or siRNAs. Expression of these sequences in the target cell enables expression of cellular genes and/or the transcription of cellular mRNA to be controlled.

In one embodiment of the present invention, the mutant virus for use as a viral vector is a mutant Rhabdovirus. In another embodiment, the mutant virus is a Rhabdovirus containing one or more mutation in the M protein. In another embodiment, the mutant virus is VSV comprising one or more mutation in the M protein.

When used as viral vectors, the mutant viruses of the present invention can be used to engineer donor cells ex vivo, with the engineered cells then being returned to the donor or to another patient, or the mutant viruses of the invention can be used to engineer a patient's cells in vivo. Such methods are well-known in the art.

In one embodiment of the present invention, the viral vectors are used as "gene therapy vectors" for the delivery to a subject of a heterologous nucleic acid encoding a protein, which when expressed in the cells of the subject, supplements or supplies an activity that is otherwise deficient in the cell.

In another embodiment of the present invention, the viral vectors are used as vaccine vectors which carry a heterologous nucleic acid sequence encoding one or more antigen and are used to immunise an individual against disease and/or infection. The antigen can be, for example, a tumour, viral or bacterial antigen. The use of the viral vectors as "polyvalent" vaccine vectors is also contemplated wherein the vector comprises antigens against different organisms and thus provides immunisation against more than one disease or against infection by more than one organism.

Mutant viruses that trigger the anti-viral systems of a host cell, such as production of various cytokines, are particularly useful as vaccine vectors. Induction of cytokines can lead to stimulation of both humoral and cellular immune responses and thus improve the efficacy of the vaccine vector.

The effective amount of the mutant virus of the invention to be administered to a subject when used as a vaccine vector will vary depending on the encoded antigen(s), the age, weight and sex of the subject, and the mode of administration. A worker skilled in the art can determine the dosage required for immunization of a specific subject using standard techniques well-known in the art.

In order to evaluate the efficacy of the mutant viruses of the invention as vaccine vectors, challenge studies can be conducted. Such challenge studies are typically conducted using laboratory animals and involve the inoculation of groups of animals with a mutant virus by various techniques, e.g. intranasally, intramuscularly. Control groups to which the effects of the mutant virus can be compared should be set up in parallel. Control groups can include non-inoculated animals and animals inoculated with, for example, commercially available alternative vaccines. After an appropriate period of time post-inoculation, the animals are challenged with the pathogenic agent (i.e. the micro-organism, virus, or tumour cells). Blood samples collected from the animals pre- and post-inoculation, as well as post-challenge are then analysed for an antibody response to the pathogenic agent. Suitable tests for the antibody response include, but are not limited to, Western blot analysis and Enzyme-Linked Immunosorbent Assay (ELISA). Alternatively, when the animals have been challenged with tumour cells, the growth of the tumour cells is monitored, for example, by monitoring the increase in the size or weight of the tumour.

Cellular immune response can also be assessed by techniques such as lymphocyte blastogenesis, to monitor induction of cellular immunity (T lymphocyte), and interferon release, to monitor induction of cytokines.

2. Oncolytic Agents

As is known in the art, certain viruses are capable of acting as selective oncolytic agents. Examples include, VSV, Newcastle disease virus, parvovirus H-1 and certain engineered viruses, such as the ONYX-015 human adenovirus (see, for example, International PCT applications WO 01/19380 and WO 00/62735 and Bell, J C, Lichty B D, and Stojdl D. 2003 *Cancer Cell* 4:7-11). The effectiveness of oncolytic virus suppression of tumour cell growth in part resides in the differential susceptibility of tumour cells, compared to normal cells, to viral infection. Cancer cells gain a survival advantage over their normal counterparts by acquiring mutations in growth inhibitory or apoptotic pathways. One defect, frequently selected for during tumour evolution, is a loss of interferon (IFN) responsiveness. Interferon is also a key mediator of the individual cell's anti-viral response and thus tumour cells that acquire mutations allowing them to escape interferon mediated growth control programs, will simultaneously compromise their innate anti-viral response.

In such cells, where the innate anti-viral response is compromised the inability of the mutant viruses to block nuclear export of mRNA or protein will not affect the ability of the mutant virus to replicate in the cell. The mutant viruses of the present invention, which are capable of triggering anti-viral systems in an infected cell while remaining sensitive to those anti-viral systems, will thus be able to selectively replicate in and inhibit the growth of, or kill, tumour cells, but will be unable to replicate in normal cells. Accordingly, the present invention provides for the use of the mutant viruses as improved oncolytic agents.

It will be appreciated that viral proteins involved in blocking nuclear mRNA or protein transport may also have other effects on an infected cell. For example, the VSV M protein has been shown to be important for targeting the protein to the mitochondria of an infected cell leading to cytotoxic effects. The M protein has also been shown to interact with the host protein TSG101 to promote efficient budding of progeny virions from the infected cell.

The present invention, therefore, provides for recombinant mutant Rhabdoviruses having one or more mutation in the M protein that not only decreases the ability of the mutant virus to block nuclear transport, but also alters the interaction of the M protein with the mitochondria of the host cell. The N-terminus of VSV M protein has been shown to be important for the targeting of this protein to the mitochondria of an infected cell. Mutations in this region of the protein that enhance or abrogate this localisation will thus modulate the cytotoxic properties of the viral vector. Depending on the introduced mutation, the cytotoxicity of the mutant virus may be increased or decreased. Those mutant viruses engineered to have one or more mutation in the M protein resulting in an increased cytotoxicity would be particularly efficient oncolytic agents.

The present invention further contemplates the use of recombinant Rhabdoviruses having one or more mutation in the M protein that alter the interaction of the virus with the host protein TSG101. TSG101 is a tumour suppressor protein, the expression and function of which is often altered in malignant cells. Introduction of mutations into the M protein that interfere with this interaction can result in recombinant viruses that replicate more efficiently in tumour cells, leading to more effective oncolytic agents.

The oncolytic activity of the mutant viruses of the invention can be determined using standard xenograft tumour models, in which a human tumour has been implanted into an immune comprised animal. Examples of xenograft models of human cancer include, but are not limited to, human solid tumour xenografts in mice, implanted by sub-cutaneous injection and used in tumour growth assays; human solid tumour isografts in mice, implanted by fat pad injection and used in tumour growth assays; experimental models of lymphoma and leukaemia in mice, used in survival assays, and experimental models of lung metastasis in mice.

The oncolytic activity of the mutant viruses can be determined by comparing tumour growth in xenograft animals treated with mutant virus and untreated controls. Control animals that have been infected with the wild-type oncolytic virus may also be used. The mutant viruses can be administered directly to the tumour or systemically, or they can be used to infect cells ex vivo with the cells subsequently being administered to the animal. Syngeneic mouse model systems in which tumours are established sub-cutaneously or by intravenous injection (to form lung tumours) can also be used to test the oncolytic activity of the mutant viruses.

3. Vaccine Adjuvants

Mutant viruses of the invention that are capable of triggering the anti-viral systems in a host cell are ideal candidates for vaccine adjuvants. As is known in the art, many antigens are not strongly immunogenic and, when used as vaccines, require the addition of an adjuvant to stimulate a strong immune response in the subject. The present invention contemplates the use of the mutant viruses as vaccine adjuvants to enhance the immunogenicity of the vaccine by triggering the host anti-viral response. In one embodiment of the present invention, the mutant virus acts as a vaccine adjuvant by stimulating production of interferons and other cytokines.

4. Protective Agents in Pharmaceutical Preparations

As indicated above, mutant viruses of the present invention that trigger the anti-viral systems of the cells which they infect can limit replication of the wild-type virus and other viruses attempting to infect neighbouring cells. Infection of cells with these mutant viruses, therefore, is not only self-limiting but also protects against the emergence of revertants. The mutant viruses can thus be used as additives for pharmaceutical preparations of viruses that protect against virulent revertants arising in the preparations either during production, or after administration to a subject.

5. Other Therapeutic Applications

As indicated above, triggering of the anti-viral systems of the host cell by a mutant virus of the invention results in production of various cytokines. These mutant viruses, therefore, can be used in the treatment of diseases or disorders that can be alleviated by cytokine release, for example, cancer, autoimmune diseases and bacterial, viral and fungal infections.

6. Other Cytolytic Applications

As is known in the art, many viruses, such as HIV and HCV, downregulate the anti-viral systems of the infected cell. Other viruses, such as Poxvirus, BVDV, Bunyaviridae, Rotavirus, Influenza virus and HPV, block the anti-viral response of a host cell as part of their replicative cycle. As a result, cells infected with one of these viruses may have an increased susceptibility to infection by the mutant viruses of the invention. As indicated above, in cells with compromised anti-viral responses, the mutant viruses will still be able to replicate. Accordingly, the mutant viruses of the present invention can be used as cytolytic agents that can selectively replicate in and kill such infected cells.

Pharmaceutical Compositions

The present invention further provides pharmaceutical compositions comprising the viruses of the invention and a pharmaceutically acceptable carrier.

The pharmaceutical compositions can be in the form of aqueous suspensions which contain the mutant virus in admixture with suitable excipients including but not limited to for example, suspending agents, such as sodium carboxymethylcellulose, methyl cellulose, hydropropylmethylcellulose, sodium alginate, polyvinylpyrrolidone, gum tragacanth and gum acacia; dispersing or wetting agents such as a naturally-occurring phosphatide, for example, lecithin, The aqueous suspensions may also contain one or more preservatives, for example ethyl, or n-propyl p-hydroxy-benzoate. The pharmaceutical compositions may be in the form of a sterile injectable suspension. This suspension may be formulated according to known art using suitable dispersing or wetting agents and suspending agents such as those mentioned above. The sterile injectable preparation may also be a sterile injectable solution or suspension in a non-toxic parentally acceptable diluent or solvent. Acceptable vehicles and solvents that may be employed include, but are not limited to, water, Ringer's solution, lactated Ringer's solution and isotonic sodium chloride solution.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philiedelphia, Pa. (2000).

Kits

The present invention provides for kits containing a mutant virus of the invention for use in immunisation, and for kits containing a mutant virus of the invention carrying one or more heterologous genes for use as a vector for the delivery of a heterologous gene(s) to a subject. The mutant viruses may be provided in the kits in the form of pharmaceutical compositions. Individual components of the kits would be packaged in separate or common containers and, associated with such containers, can be a notice in the form prescribed by a governmental agency regulating the manufacture, use or sale of pharmaceuticals or biological products, which notice may reflect approval by the agency of manufacture, use or sale for animal or human administration.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a subject. Such an instrument may be an inhalant, syringe, pipette, eye dropper or similar medically approved delivery vehicle.

EXAMPLES

Example 1

Oncolytic VSV Strains with Defects in the Shutdown of IFN-β Signalling

Materials and Methods
Viruses

The Indiana serotype of VSV was used throughout this study and was propagated in L929 cells. T1026R (Desforges, et al. 2001, *Virus Research* 76(1): 87-102), and TP3 (Desforges, et al. 2001, ibid) herein referred to as AV1 (or Mut2) and AV2 (or Mut3) respectively, were shown in this study and elsewhere to be IFN-inducing mutants of the HR strain of wild-type VSV Indiana (Francoeur, et al. 1987, *Virology* 160 (1): 236-45).
IFN Production ELISA Interferon-α levels were measured in cell culture media using Human Interferon-Alpha ELISA kit (PBL Biomedical) per manufacturer's directions. Briefly, 100 µl of culture medium was collected at 48 hours post-infection and incubated in a 96-well microtiter plate along with blanks and standards supplied by manufacturer. Samples were processed as per manufacturer's instructions and then read on a DYNEX™ plate reader at 450 nm.
Determination of In Vivo Toxicity of VSV Mutant Viruses Eight (8) to 10 week old female mice (strains as indicated) were divided into groups of 5 and infected with 1 log or ½ log dilutions of virus from $1\times10^{10}$ pfu to $1\times10^2$ pfu (depending on the virus and mouse strain) by the indicated route. Animals were monitored for weight loss, dehydration, piloerection, huddling behaviour, respiratory distress and hind limb paralysis. Mice showing moderate to severe morbidity were euthanized as per good laboratory practices prescribed by the CCAS. Lethal dose 50 values were calculated by the Karber-Spearman method.

Four week old Balb/C mice or Balb/C interferon alpha receptor knock out mice (IFNAR$^{-/-}$) (Steinhoff et al., 1995, *J. Virol.*, 69:2153-2158) were infected intranasally with $10^4$ pfu of either: WT VSV, AV1 or AV2. Mice were monitored for signs of morbidity and were euthanized upon signs of severe respiratory distress.

Determination of In Vivo Toxicity of Mixed Samples of Wild-Type and Mutant VSV Strains Balb/C PKR$^{-/-}$ mice were previously determined to be highly sensitive to intranasal infection with WT VSV with an LD100 of approximately 10 pfu (Stojdl et al., 2000, *J. Virol.*, 79:9580-9585). Groups of 3 mice were infected by intranasal instillation with either: WT, AV2 or mixtures of these strains. Mice were monitored for signs of morbidity and were euthanized upon signs of severe respiratory distress or hind limb paralysis.
Ovarian Xenograft Cancer Model in Athymic Mice Approximately $1\times10^6$ ES-2 human ovarian carcinoma cells were injected into the peritoneal cavity of CD-1 athymic mice. Ascites development is generally observed by day 15 after cell injection. On days 12, 14, and 16, mice were treated with $1\times10^9$ AV2 virus or $1\times10^9$ pfu equivalent of UV-inactivated AV2 VSV, intraperitoneal injection. Mice were monitored for morbidity and euthanized upon development of ascites.
Subcutaneous Tumour Model To establish subcutaneous tumours, 8-10 week old Balb/c female mice were shaved on the right flank and injected with $1\times10^6$ CT26 colon carcinoma cells (Kashtan, et al. 1992, *Surg Oncol* 1(3): 251-6) syngeneic for Balb/c mice. These tumours were allowed to develop until they reached approximately 10 mm$^3$ at which time virus treatments were initiated. Groups of animals received 1, 6 or 12 doses of the indicated virus, every other day. Each dose of $5\times10^8$ pfu was administered by tail vein injection. Tumours were measured daily and volumes calculated using the formula ½(L×W×H). Mice were weighed daily and monitored for weight loss, dehydration, piloerection, huddling behaviour, respiratory distress and hind limb paralysis Animals were euthanized when their tumour burden reached end point (750 mm$^3$)
Lung Model Lung tumours were established in 8-10 week old female Balb/c mice by tail vein injection of $3\times10^5$ CT26 cells (Specht, et al. 1997, *J Exp Med* 186(8): 1213-21). On days 10, 12, 14, 17, 19 and 21, groups of mice received $5\times10^7$ pfu of the indicated virus by intranasal instillation as described elsewhere (Stojdl, et al. 2000, *Journal of Virology* 74(20): 9580-5). Mice were weighed daily and monitored for weight loss, dehydration, piloerection, huddling behaviour, respiratory distress and hind limb paralysis Animals were euthanized at the onset of respiratory distress and their lungs examined to confirm tumour development.
MTS Assay In each experiment, the test cell line was seeded into 96-well plates at $3\times10^4$ cells/well in growth medium (DMEM-F12-HAM+10% FBS). Following overnight incubation (37° C., 5% CO$_2$), media was removed by aspiration and to each well was added 20 µl of virus-containing media (α-MEM, no serum) ranging in 10-fold increments from $3\times10^6$ pfu/well to 3 pfu/well or negative control media containing no virus. Each virus dose tested was done in replicates of six. After a 60 minute incubation to allow virus attachment, 80 µl of growth medium was added to each well and the plates were incubated for another 48 hours. Cell viability was measured using the CellTitre 96™ AQ$_{ueous}$ MTS reagent (Promega Corp.), which makes use of solutions of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS). MTS is bioreduced by cells into a formazan product that is soluble in tissue culture medium. The absorbance of the formazan product at 490 nm can be measured directly from 96-well assay plates. The quantity of formazan product, as determined from the absorbance at 490 nm, is directly proportional to the number of living cells in culture.

To assay for IFN defects, cell lines were pretreated with either 5 units/ml of IFN-α or IFN-β for 12 hours and then challenged with a range of doses of WT VSV as described above. A standard MTS assay was performed and the results compared with results from non-pretreated cells.

Microarray

OVCAR4 cells either mock treated or infected with wild-type (WT) and mutant VSV strains were harvested in PBS, pelleted and resuspended in 250 µl of resuspension buffer (10 mM Tris pH 7.4, 15 mM NaCl, 12.5 mM $MgCl_2$). 600 µl of Lysis buffer (25 mM Tris pH 7.4, 15 mM NaCl, 12.5 mM $MgCl_2$ 5% sucrose and 1% NP-40) was added and the lysates were incubated at 4° C. for 10 min. with occasional vortexing. Nuclei were collected by centrifugation at 1000×g for 3 min The supernatant (cytoplasmic fraction) was collected and frozen at −80° C., while the pellet (nuclear fraction) was washed once with 250 µl of lysis buffer and frozen. Total RNA was isolated from both nuclear and cytoplasmic fractions using the Qiagen RNeasy™ kit (as per manufacturer's instructions; Qiagen, Mississauga, Canada) followed by LiCl precipitation to concentrate each sample. Twenty micrograms of each RNA sample was processed according to manufacturer's standard protocol (Affymetrix; Santa Clara Calif., USA) and hybridized to an Affymetrix GeneChip™ Human Genome U133A Array (HG U133A chip). Each chip was scaled to 1500, normalized to the 100 normalization control genes present on each HG U133A chip, then all nuclear samples were normalized to the mock nuclear sample on a per gene basis, and the cytoplasmic fractions were normalized to the corresponding mock cytoplasmic sample. Data was analysed using Genespring™ software (Silicon Genetics; Redwood City Calif., USA).

Western Blotting

OVCAR4 cells were grown in RPMI (Wisent) supplemented with 10% Fetal Bovine Serum (Wisent). $1.0×10^7$ cells were plated in 10 cm dishes the day prior to infection. Upon infection, the media was removed and replaced with RPMI alone prior to the addition of $5×10^7$ pfu per VSV viral strain. One hour after virus addition, media was removed and replaced with RPMI supplemented with 10% FBS for the remaining duration of the experiment. Cells were lysed in standard NP-40 lysis buffer and 75 µg of whole cell extract were run on SDS-polyacrylamide gel and blotted with the following antibodies as indicated: IRF-7 (sc-9083), IRF-3 (sc-9082), ISG56 (a gift from Genes Sen), VSV-N (polyclonal directed against the full length Indiana N protein), and Actin (sc-8432).

Constructs and Viral Rescue

Creation of the constitutively active IRF-74 (IRF-7Δ 247-467) has been previously described elsewhere (Lin et al., 2000, *J. Biol. Chem.*, 275:34320-34327). IRF-7Δ 247-467 was amplified by PCR using a forward primer to the Flag epitope with an additional 5' VSV cap signal and an Xho1 linker:

```
                                      [SEQ ID NO: 7]
5'-ATCGCTCGAGAACAGATGACTACAAAGACGATGACGACAAG-3'
``` together with a specific IRF-7 reverse primer containing a VSV poly A signal and an NheI linker:

```
                                      [SEQ ID NO: 8]
5'-ATCGGCTAGCAGTTTTTTTCAGGGATCCAGCTCTAGGTGGGCTGC-
3'
```

The PCR fragment was then cloned into the Xho1 and Nhe1 sites of the rVSV replicon vector pVSV-XN2 (provided by John Rose). Recovery of rVSV has been previously described (Lawson et al., 1995, *Proc. Natl. Acad. Sci. USA*, 92:4477-4481).

Quantitative PCR of Interferon beta mRNA

Nuclear and cytoplasmic total RNA from infected or mock infected OVCAR4 cells was isolated as per manufacturers instruction (RNeasy; Qiagen, Mississauga, Canada). Four micrograms of total RNA was DNase treated and reverse transcribed. Quantitative PCR was performed in triplicate to amplify IFN-β and hypoxanthine-guanine phosphoribosyl-transferase (HPRT) targets from each using Roche Lightcycler™ technology (Roche Diagnostics, Laval, Canada). Crossing points were converted to absolute quantities based on standard curves generated for each target amplicon. IFN-β signal was subsequently normalized to HPRT as HPRT levels are unchanged during the course of these infections, data not shown. Primers used to amplify IFN-β were:

```
sense
5'-TTGTGCTTCTCCACTACAGC-3';       [SEQ ID NO: 9]

antisense
5'-CTGTAAGTCTGTTAATGAAG-3'        [SEQ ID NO: 10]
``` and HPRT primers were:

```
sense
5'-TGACACTGGCAAAACAATGCA-3';      [SEQ ID NO: 11]

antisense
5'-GGTCCTTTTCACCAGCAAGCT-3'.      [SEQ ID NO: 12]
```

RT-PCR of Interferon Alpha and Interferon Stimulated Genes

A549 cells cultured in F12K medium supplemented with 10% FBS were infected with WT or mutant VSV strains (MOI 10, wherein MOI refers to Multiplicity Of Infection, which is the ratio of infectious virus particles to cells). RNA was extracted 4 hours post infection using Trizol (Invitrogen) according to the manufacturer's instructions. One microgram of RNA was reverse transcribed with Oligo dT primers and 5% of RT was used as template in a Taq PCR. Primers used were as follows:

```
Mx forward primer
                                      [SEQ ID NO: 13]
5'-ATG GTT GTT TCC GAA GTG GAC-3';

Mx reverse primer
                                      [SEQ ID NO: 14]
5'-TTT CTT CAG TTT CAG CAC CAG-3';

VSV N forward primer
                                      [SEQ ID NO: 15]
5'-ATG TCT GTT ACA GTC AAG AGA ATC-3';

VSV N reverse primer
                                      [SEQ ID NO: 16]
5'-TCA TTT GTC AAA TTC TGA CTT AGC ATA-3';
```

-continued

RANTES forward primer

[SEQ ID NO: 17]
5'-TAC ACC AGT GGC AAG TGC TCC AAC CCA G-3';

RANTES reverse primer

[SEQ ID NO: 18]
5'-GTC TCG AAC TCC TGA CCT CAA GTG ATC C-3';

β-Actin forward primer

[SEQ ID NO: 19]
5'-ACA ATG AGC TGC TGG TGG CT-3'
and

β-Actin reverse primer

[SEQ ID NO: 20]
5'-GAT GGG CAC AGT GTG GGT GA-3'.

Results

Attenuation of VSV In Vivo is Dependent Upon Intact Interferon Pathways

Figure 1D:
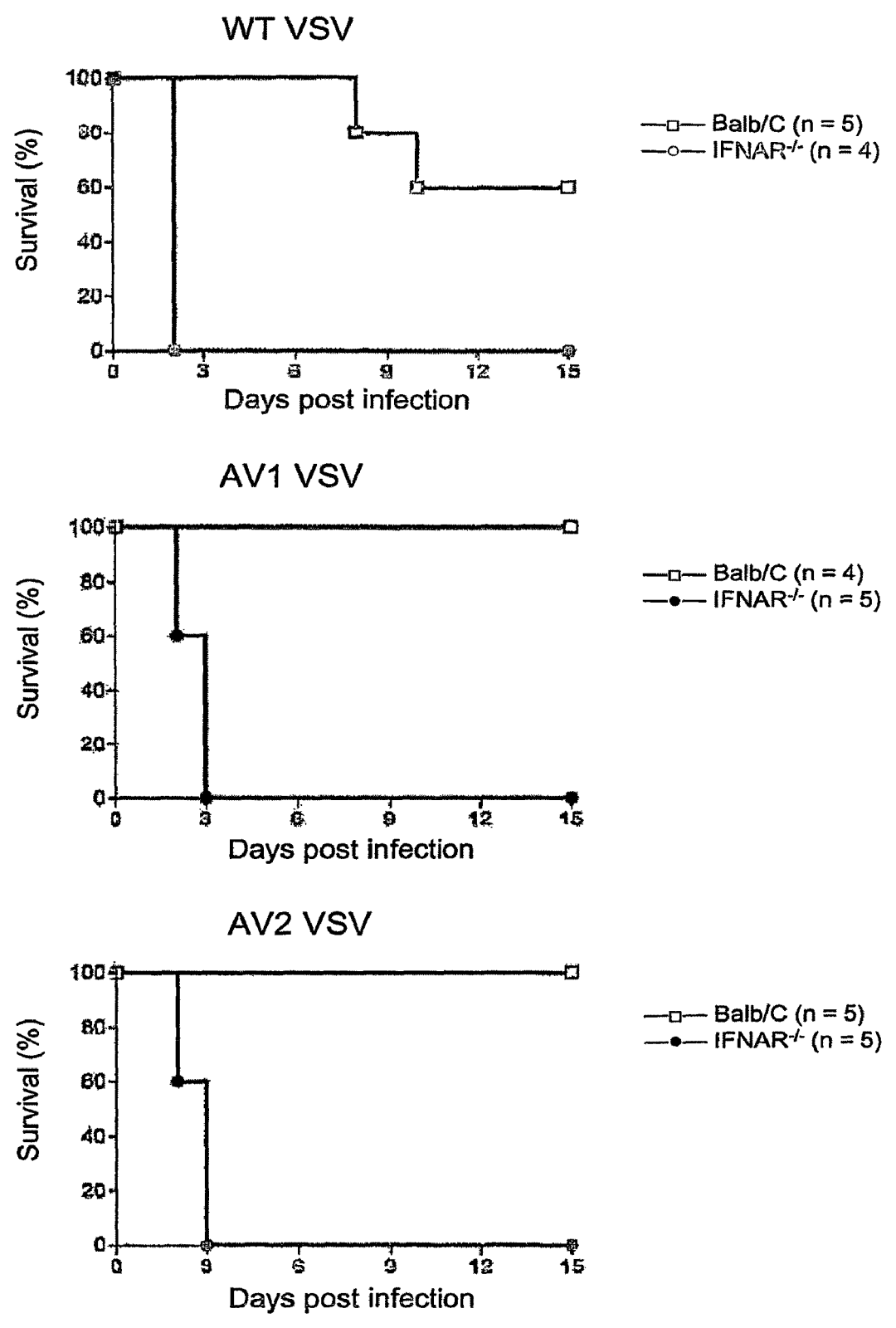

Two variants of VSV which produce small plaques on interferon responsive cells (herein referred to as AV1 and AV2), were found to induce from twenty to fifty times more interferon alpha (IFN-α), than wild type (WT) VSV following infection of epithelial cell lines (FIG. 1A). Complete genomic sequencing of the variants revealed that they differed from the wild type strain in their M proteins with only a single amino acid substitution in the case of AV1 (M51R) and two amino acids (V221F and S226R) in AV2. The $LD_{50}$ of AV1 and AV2 when delivered intranasally to Balb/C mice was determined to be 10,000 times greater than WT VSV delivered by the same route (FIG. 1B). Similar results were seen in CD-1 mice (WT=$1 \times 10^6$; AV1=$2 \times 10^8$ pfu). Significantly, AV1 and AV2 were as toxic as wild type virus when used to infect interferon receptor knock-out animals indicating that the attenuation of AV1 and AV2 growth in vivo is dependent upon an intact interferon system (FIG. 1C). Furthermore, when used in combination with WT VSV, the mutant strain AV2 was found to protect highly susceptible mice ($PKR^{-/-}$) from WT VSV (FIG. 1D). In fact, even at a dose 100 times greater than the $LD_{100}$ for WT VSV, no signs of morbidity (dehydration, piloerection, malaise, decreased activity, respiratory distress, hind limb paralysis) were apparent when mice were challenged with AV2 and WT VSV simultaneously. Together with the observation that these mutants allow IFN to be produced following infection, this data is consistent with a model whereby infection with AV1 or AV2 mutant strains of VSV induces interferon production in the host, thereby establishing an antiviral state protecting the host from pathologic infection.

Both Wild Type and Attenuated VSV Mutants Trigger Innate Anti-Viral Responses

To determine at what point during infection the wild type and attenuated viruses diverge in their abilities to induce or inactivate host cell antiviral responses, the early signalling events occurring during VSV infection of a host cell needed first to be established. The use of microarray analysis over a time course of virus infection should allow early signalling events triggered by VSV infection to be detected which lead either directly or indirectly to the transcriptional activation of antiviral genes. It is evident from the microarray data that VSV infection leads to the upregulation of a number of genes in a specific, sequential order. Genes were, therefore, grouped together based on: (1) their kinetics of upregulation over time and (2) their pattern of induction in response to WT versus mutant VSV infection. These cohorts of genes likely correspond to 3 separate transcriptional waves (Table 1, and FIGS. 2A, B and C). Consistent with this, IFN-β, IRF-7 and IFN-α subtypes segregated each to separate cohorts. Other groups have established that, in response to a number of stimuli, the latent transcription factors IRF-3, NFκB and c-JUN/ATF-2 become activated and assemble together with CBP/p300 on the IFN-β promoter to induce its expression (Wathelet et al., 1998, Mol. Cell 1:507-518). Also, IFN-β is known to act in an autocrine fashion to induce the activation of the ISGF3 transcriptional complex leading to the induction of IRF-7 and other genes containing ISRE elements in their promoters (Lu et al., 2000, J. Biol. Chem., 275:31805-31812; Zhang and Pagano, 1997, Mol. Cell Biol., 17:5748-5757; Zhang and Pagano, 2001, J. Virol., 75:341-350). Furthermore, ectopic expression of IRF-7 has been shown to be critical for the expression of IFN-α in cells unable to form ISGF3 complexes (Sato et al., 1998, FEBS Lett., 441:106-110). This ascribed dependency of IFN-α induction on IRF-7 and IRF-7 expression on IFN-β is reminiscent of the kinetic profiles of the genes in the described array. In light of the these observations, and assuming IFN-β, IRF-7 and IFN-α1 as archetypal genes in a general model, it appears that these cohorts of genes may correspond to 3 separate transcriptional waves; each dependent on, and triggered by the previous transcriptional wave (Table 1, and FIGS. 2A, B and C).

TABLE 1

Microarray analysis of the transcriptional response to VSV infection over time

| | | WT Hours post infection | | | AV1 Hours post infection | | | AV2 Hours post infection | | |
|---|---|---|---|---|---|---|---|---|---|---|
| Accession # | Common name | 3 | 6 | 12 | 3 | 6 | 12 | 3 | 6 | 12 |
| PRIMARY TRANSCRIPTIONAL RESPONSE | | | | | | | | | | |
| NM 000201.1 | CD54 | 2.3 | A | A | 3.3 | 3.0 | 33.6 | 2.7 | 5.4 | 56.8 |
| NM 016323.1 | CEB1 | 2.0 | 21.2 | 204.4 | 1.6 | 38.0 | 279.3 | 1.9 | 73.6 | 490.5 |
| U83981 | GADD34 | 10.8 | 57.5 | 95.0 | 3.1 | 48.8 | 422.7 | 5.5 | 159.0 | 686.7 |
| NM_002176.1 | IFN beta | 4.2 | 103.2 | 488.6 | 3.2 | 154.5 | 1531.6 | 3.6 | 487.3 | 2157.9 |
| NM 000600.1 | IL6 | 7.3 | 19.1 | 38.2 | 3.8 | 44.7 | 171.6 | 7.4 | 120.3 | 238.7 |
| BE888744 | ISG54 | 19.5 | 173.1 | 804.5 | 4.7 | 141.0 | 721.9 | 11.4 | 268.4 | 1357.8 |
| NM_00 1548.1 | ISG56 | 32.3 | 285.9 | 855.2 | 20.0 | 456.8 | 1411.7 | 39.8 | 766.0 | 1992.1 |
| NM_00 1549.1 | ISG60 | 7.6 | 57.5 | 238.0 | 4.1 | 97.7 | 288.6 | 7.0 | 151.6 | 457.7 |
| AF063612.1 | OASL | 6.6 | 71.8 | 222.0 | 3.4 | 81.9 | 388.9 | 5.7 | 172.0 | 776.9 |
| NM_021127.1 | PMAIP1 | 5.2 | 22.1 | 58.6 | 2.1 | 17.3 | 87.5 | 4.3 | 34.3 | 169.8 |
| NM_002852.1 | PTX3 | 5.9 | 3.1 | A | 6.4 | 11.7 | 114.0 | 4.9 | 29.9 | 117.6 |

TABLE 1-continued

Microarray analysis of the transcriptional response to VSV infection over time

| | | WT Hours post infection | | | AV1 Hours post infection | | | AV2 Hours post infection | | |
|---|---|---|---|---|---|---|---|---|---|---|
| Accession # | Common name | 3 | 6 | 12 | 3 | 6 | 12 | 3 | 6 | 12 |
| AF332558.1 | PUMA | 10.6 | A | A | A | 38.7 | 211.6 | 9.8 | 77.8 | 428.0 |
| NM 002985.1 | RANTES | 3.4 | 60.1 | 945.0 | 2.6 | 84.9 | 1796.7 | 4.1 | 301.8 | 3916.1 |
| AY029 180.1 | SUPAR | 3.7 | 9.8 | 14.7 | 2.4 | 10.5 | 40.5 | 2.8 | 27.7 | 46.3 |
| NM_006290.1 | TNFAIP3 | 2.8 | 6.3 | 15.5 | 2.7 | 13.8 | 83.5 | 3.1 | 30.5 | 152.8 |
| | SECONDARY TRANSCRIPTIONAL RESPONSE | | | | | | | | | |
| NM_030641.1 | APOL6 | A | A | A | A | 15.3 | 40.8 | A | 25.2 | 37.3 |
| AF323540.1 | APOLL | 1.8 | A | A | 1.0 | 11.3 | 25.7 | 2.2 | 10.7 | 34.5 |
| U84487 | CX3C chemokine precursor | 2.0 | 2.5 | 2.5 | 1.7 | 7.0 | 45.1 | 2.3 | 14.1 | 65.9 |
| BC002666.1 | GBP1 | A | A | 4.2 | A | 35.9 | 171.6 | 1.4 | 66.2 | 249.2 |
| NM_006018.1 | HM74 | A | A | A | 2.2 | 29.1 | 72.5 | A | 66.4 | 45.4 |
| NM_031212.1 | hMRS3/4 | A | A | A | 2.5 | 4.2 | 21.3 | A | 10.1 | 18.3 |
| NM 005531.1 | IFI16 | A | A | A | 2.4 | 12.8 | 38.1 | 2.8 | 18.9 | 46.2 |
| NM_005532.1 | IFI27 | A | A | 21.9 | A | 36.6 | 281.0 | A | 51.0 | 295.4 |
| NM 004509.1 | IFI41 | A | A | A | A | 10.0 | 22.8 | 1.3 | 11.9 | 18.1 |
| NM_022873.1 | IFI-6-16 | 0.9 | 2.5 | 2.2 | 0.7 | 7.0 | 15.6 | 1.1 | 9.6 | 15.7 |
| NM_003641.1 | IFITM1 | 1.9 | A | A | 1.2 | 8.5 | 67.1 | 1.9 | 14.3 | 42.1 |
| AA749101 | IFITM1 | 1.2 | 3.1 | 2.3 | 1.0 | 6.6 | 40.9 | 1.2 | 9.5 | 32.6 |
| NM 000882.1 | IL12A | 1.6 | A | A | A | 4.9 | 13.7 | A | 6.5 | 28.8 |
| M15329.1 | IL1A | nd | A | A | A | 8.3 | 79.4 | A | 27.0 | 287.6 |
| NM_004030.1 | IRF7 | 1.4 | A | A | A | 19.9 | 109.9 | 2.2 | 33.7 | 144.3 |
| NM 006084.1 | IRF9 | A | A | 1.2 | 1.6 | 6.5 | 11.2 | 1.5 | 7.8 | 17.4 |
| BC001356.1 | ISG35 | 1.1 | A | A | 1.0 | 5.8 | 23.2 | 1.4 | 7.1 | 20.2 |
| AF280094.1 | ISG75 | 1.3 | 1.8 | 2.2 | 1.5 | 10.3 | 16.2 | 1.2 | 12.5 | 13.8 |
| AF280094.1 | ISG75 | 0.9 | 1.7 | A | 1.2 | 7.5 | 10.8 | 1.5 | 9.5 | 11.1 |
| U17496.1 | LMP7 | A | A | A | A | 7.6 | 15.3 | 0.9 | 10.0 | 10.4 |
| NM_006417.1 | MTAP44 | A | A | 23.3 | A | 10.8 | 82.7 | A | 18.0 | 133.9 |
| NM_002462.1 | MX A | A | A | 27.6 | A | 48.1 | 261.9 | A | 85.7 | 232.9 |
| AB014515 | NEDD4 BP1 | A | A | 9.2 | 2.0 | 4.0 | 13.1 | 1.5 | 4.5 | 19.5 |
| NM_002759.1 | PKR | 0.5 | 0.9 | 2.0 | 0.8 | 4.3 | 15.2 | 1.0 | 6.6 | 9.6 |
| NM_021 105.1 | PLSCR1 | 1.4 | 1.7 | A | 2.2 | 5.0 | 24.9 | 2.1 | 4.9 | 15.1 |
| NM_017912.1 | putative Ub ligase | A | A | 19.1 | A | 9.6 | 26.3 | A | 12.5 | 24.8 |
| BF939675 | SECTM1 | A | A | A | A | 20.7 | 93.8 | A | 24.8 | 33.9 |
| BC004395.1 | Similar to apolipoprotein L | A | A | A | A | 11.7 | 17.2 | A | 14.6 | 21.3 |
| NM_003141.1 | SSA1 | A | A | A | 1.2 | 5.9 | 11.2 | 1.4 | 7.9 | 11.1 |
| AA083478 | STAF50 | nd | A | nd | 1.7 | 8.5 | 96.3 | nd | 16.7 | 56.1 |
| NM_005419.1 | STAT2 | 1.1 | A | A | 1.3 | 3.0 | 9.1 | 1.1 | 4.3 | 9.1 |
| NM_003810.1 | TRAIL | A | A | A | A | 22.4 | 135.4 | 0.7 | 37.3 | 88.6 |
| NM_020119.1 | ZAP | A | A | 19.4 | 0.9 | 4.6 | 79.9 | A | 11.4 | 133.8 |
| | TERTIARY TRANSCRIPTIONAL RESPONSE | | | | | | | | | |
| M12350.1 | IFN-27 | A | A | A | nd | nd | 102.3 | nd | A | 101.4 |
| NM_024013.1 | IFNA1 | nd | A | A | nd | 2.2 | 53.6 | nd | A | 44.0 |
| NM 002171.1 | IFNA10 | A | A | A | A | A | 96.2 | A | A | 55.1 |
| NM_006900.2 | IFNA13 | A | A | A | A | A | 165.4 | nd | A | 152.1 |
| NM_002 172.1 | IFNA14 | A | A | A | A | A | 159.0 | A | 4.4 | 91.1 |
| NM_002 173.1 | IFNA16 | 1.0 | A | 1.8 | 1.1 | 0.9 | 139.7 | 0.7 | 3.3 | 95.7 |
| M38289.1 | IFNA17 | A | A | A | A | A | 21.5 | A | A | 19.8 |
| NM_002 169.1 | IFNA5 | 1.0 | A | A | 0.9 | A | 16.4 | 0.9 | A | 11.6 |
| NM_021057.1 | IFNA7 | A | A | 3.5 | A | A | 105.0 | A | 3.4 | 61.7 |

Data represented as fold change compared to mock infected samples. All samples are from nuclear fractions of infected cells
A = Absent (no detectable mRNA);
nd = no data;
boxed genes represent "archetypal genes", see text for explanation
WT VSV M protein blocks interferon beta signalling, while M protein from AV1 and AV2 cannot.

With a better understanding of the early transcriptional response to VSV infection, an understanding of the differences in these responses between the WT and "IFN-inducing strains" was sought. By Western blotting, it appears that WT, AV1 and AV2 viruses trigger IRF-3 phosphorylation with similar kinetics (FIG. 2E). Further, it was found that some of the genes directly regulated by the transcription factors IRF-3, NFκB and c-JUN/ATF-2 were upregulated to the same degree in cells infected with WT, AV1 or AV2 viruses (FIG. 2A). For example, primary response genes were robustly induced 3-6 hours post infection by all three viruses (FIGS. 2A, D and E). On the other hand, secondary response genes that require the production of IFN-β and the autocrine activation of the JAK/STAT pathway (FIG. 2B), were differentially induced by the wild type and attenuated viruses (see IRF-7 in FIGS. 2B & 2E). As a consequence of the impaired IRF-7 production in WT VSV infected cells, tertiary response gene products like the IFN-α transcripts were not induced in wild type VSV infected cells (FIG. 2C) although strongly expressed in AV1 and AV2 infected cells. Taken together, these results suggest that wild type VSV, through its M protein, affects a block between the primary and secondary antiviral transcriptional responses shown in FIG. 2. In earlier transfection experiments it has been suggested that VSV M protein either blocks the transcription of IFN-β (Ferran and Lucas-Lenard, 1997, *J. Virol.*, 71:371-377), inhibits the nuclear export of mRNAs (Her et al., 1997, *Science*, 276: 1845-1848; von Kobbe et al., 2000, *Mol. Cell*, 6:1243-1252), or interferes with Jak/Stat signaling (Terstegen et al., 2001, *J. Immunol.*, 167:5209-5216). The transcript profiling studies described herein would be consistent with either of the latter two mechanisms, however, no impairment in the induction of the Jak/Stat pathway by exogenous interferon in infected cells was observed (data not shown). On the other hand, when microarray or RT-PCR analysis was used to compare and contrast transcripts in nuclear and cytoplasmic fractions, clear differences between wild type and attenuated virus infected cells were found (FIG. 3) Importantly, IFN-β mRNA although induced in nuclear fractions by all three viruses was not found to a significant degree in the cytoplasmic pool of mRNAs in wild type infected cells.

In total, these results are consistent with the idea that upon infection, wild type VSV triggers a primary antiviral response, but through co-ordinate expression of viral gene products blunts secondary and tertiary responses by blocking nuclear export of critical antiviral mRNAs. In support of this model, a wild type VSV that expresses a constitutively active version of IRF-7 was constructed. As expected, this virus has an attenuated phenotype and is capable of inducing the expression of IFN-α genes within 4 hours post infection, even in the presence of wild type VSV M protein (FIG. 2D; IFN-α is not expressed until 12 hours post infection in the case of AV1 and AV2 infections: Table 1).

Attenuated Viruses AV1 and AV2 Retain their Ability to Kill Tumour Cells

To assess the oncolytic properties of the attenuated VSV strains, the NCI human tumour cell panel (60 cell lines from a spectrum of malignancies) was challenged with either: WT, AV1 or AV2 viruses, and assayed for metabolic cell death 48 hours later as described in Materials and Methods. It is clear from Table 2A that WT VSV is able to productively infect and kill a wide range of different cancer cell types. Furthermore, as our earlier work had indicated (Stojdl D F, Lichty B, Knowles S, Marius R, Atkins H, Sonenberg N, Bell J C 2000 *Nature Medicine* 6:821-5), the majority of cancer cell lines tested (some 80%) demonstrated impaired responses to either IFN-α or IFN-β (Table 2B). Not surprisingly therefore, AV1 and AV2 were as effective at killing these tumour cell lines as WT VSV, presumably due to the IFN signalling defects in these cells (Table 2A & B).

TABLE 2A

Mutant VSV strains are highly lytic on members of the NCI 60 panel of cancer cell lines.

|  | WT |  | AV1 |  | AV2 |  |
|---|---|---|---|---|---|---|
|  |  | MOI |  | MOI |  | MOI |
| Leukemia | 67% (4/6)* | 0.13 | nd |  | 60% (3/5) | 0.02 |
| NSC Lung carcinoma | 78% (7/9) | 0.02 | 60% (3/5) | 0.001 | 75% (6/8) | 0.19 |
| Colon carcinoma | 86% (6/7) | 0.037 | 100% (5/5) | 0.001 | 100% (6/6) | 0.017 |
| CNS | 80% (4/5) | 0.02 | 50% (1/2) | 0.6 | 60% (3/5) | 0.38 |
| Melanoma | 75% (6/8) | 0.1 | 100% (2/2) | 0.15 | 63% (5/8) | 0.25 |
| Ovarian carcinoma | 100% (6/6) | 0.3 | 67% (2/3) | 0.0005 | 60% (3/5) | 0.14 |
| Renal carcinoma | 88% (7/8) | 0.24 | 100% (3/3) | 0.14 | 100% (7/7) | 0.48 |
| Prostate | 100% (2/2) | 0.06 | 100% (2/2) | 0.035 | 100% (2/2) | 0.04 |
| Breast | 83% (5/6 | 0.009 | 75% (3/4) | 0.005 | 60% (3/5) | 0.12 |
| All cell lines tested | 82% (47/57) | 0.11 | 80% (21/26) | 0.07 | 75% (38/51) | 0.20 |

*Percent of NCI 60 panel cell lines by tumour type deemed highly sensitive to virus infection.
( ) denote the number of highly susceptible cell lines out of the number of cell lines tested. Cell line deemed highly susceptible if the $EC_{50} \leq$ MOI of 1 following a 48 infection.
MOI represents average $EC_{50}$ (MOI) of susceptible cell lines.
nd = not determined

TABLE 2B

The majority of cell lines in the NCI 60 cell panel show IFN defects

|  | Type I IFN defects |
|---|---|
| Leukemia | 100% (6/6)* |
| NSC Lung carcinoma | 71% (5/7) |
| Colon carcinoma | 100% (7/7) |
| CNS | 75% (3/4) |
| Melanoma | 85% (6/7) |
| Ovarian carcinoma | 67% (4/6) |
| Renal carcinoma | 75% (6/8) |
| Prostate | 100% (2/2) |
| Breast | 60% (3/5) |
| All cell lines tested | 81% (42/52) |

*Denotes the number of cell lines in each group which were unresponsive to either IFN-α or IFN-β pre-treatment. Cell line deemed unresponsive if IFN pre-treatment was unable to significantly affect (<10 fold) the $EC_{50}$ of cells infected with WT VSV for 48 hours.

In Vivo Oncolytic Activity of AV1 and AV2

Previously the successful treatment of subcutaneous xenograft tumours in nude mice with WT VSV was reported (Stojdl, et al. 2000, *Nature Medicine* 6(7): 821-5), however, in these experiments, exogenous interferon was required to protect the immunodeficient animals from the virus treatments. The results described above suggest that AV1 and AV2 should efficiently kill tumour cells with little toxicity in nude mouse models even in the absence of exogenously administered interferon. Human ovarian carcinoma cells were injected into the peritoneal cavity of CD-1 nude mice and allowed to grow for 12 days. Most mice (14/15) receiving UV-inactivated virus developed ascites by day 15 post treatment (the remaining mouse in this cohort reached endpoint on day 39). In contrast, 3 doses of AV2 delivered into the peritoneal cavity provided durable cures of 70% of the mice (FIG. 4A). Remarkably while a single intraperitoneal dose of WT VSV is uniformly lethal to nude mice, none of the animals treated with three doses of AV2 exhibited even symptoms of virus infection (e.g. malaise, weight loss, dehydration).

Systemic Treatment of Subcutaneous Tumours with AV1 and AV2

While the AV1 and AV2 strains are effective when injected into the primary site of tumour seeding, the therapeutic efficacy of systemically delivered attenuated strains needed to be determined. To this end, subcutaneous tumours were established by injecting CT26 colon carcinoma cells into the hind flank of syngeneic Balb/c mice. Once tumours became palpable (approximately 10 mm$^3$) virus was administered via tail vein injection. Twelve days post-treatment, mice receiving UV-inactivated VSV reached end point with an average tumour size of 750 mm$^3$ In contrast, a single treatment with AV2 showed significant efficacy, delaying the time to endpoint by almost 3 fold (34 days). Of the 8 animals in this treatment group, 7 were considered partial responders, while only 1 mouse did not respond to the treatment (Table 3). When multiple doses of AV1 or AV2 were given intravenously, the efficacy of the treatments was markedly increased (FIG. 4B & Table 3). With the exception of one animal, all tumours responded to treatment with AV1, with 3/6 mice showing complete tumour regression. Two of these mice showed complete regressions as early as day 8 and 9 respectively post-infection. Two of the remaining animals showed partial responses, delaying tumour progression by almost 2 fold compared to controls. All eight AV2 infected mice responded well to treatment with five of eight developing durable tumour regressions. In fact no sign of tumour regrowth was evident even 7 months post treatment. Furthermore, these mice failed to produce tumours when re-challenged with CT26 cells 7 months post treatment, with no trace of detectable virus (data not shown), perhaps indicating host mediated immunity to the tumour had developed.

Doubling the number of viral doses administered to tumour bearing animals did not increase the number of durable regressions (Table 3) suggesting that anti-viral immunity arising during the course of treatment may influence outcome. Also, in an approach described previously with oncolytic HSV (Lambright et al., 1999, Ann. Thorac. Surg., 68:1756-1760 and 1761-1772), the utility of injecting virus infected cells, instead of virus alone, as a therapeutic modality was tested. It was reasoned that infected cells might function as "Trojan horses" masking virus while in the vascular system and facilitating delivery of virus when they lodge in tumour neo-vasculature. To this end, CT-26 cells infected in vitro for two hours with AV2 were injected into the tail vein of tumour bearing mice. In these experiments, infected CT-26 cells appeared to be as effective a mode of delivering virus to tumour sites as using purified virus (three complete regressions and one partial response; FIG. 4B).

All forms of intravenous treatment were well tolerated by the mice, with no mortalities occurring, and minimal signs of morbidity. Infected mice had mild to medium piloerection, mild dehydration and some transient body weight loss following the initial treatment (FIG. 4C). These symptoms were only observed after the initial infection, all subsequent doses failed to elicit any signs of infection.

TABLE 3

Increased response rate with increased dose number in subcutaneous tumour model

|  |  | UV AV2 | AV 2 |
|---|---|---|---|
| 1 Dose | CR | 0%* (0/5) | 0% (0/8) |
|  | PR | 0% (0/5) | 88% (7/8) |
|  | NR | 100% (0/5) | 12% (1/8) |
| 6 Doses | CR | 0% (0/5) | 63% (5/8) |
|  | PR | 0% (0/5) | 37% (3/8) |
|  | NR | 100% (0/5) | 0% (0/8) |

TABLE 3-continued

Increased response rate with increased dose number in subcutaneous tumour model

|  |  | UV AV2 | AV 2 |
|---|---|---|---|
| 12 Doses | CR | 0% (0/5) | 63% (5/8) |
|  | PR | 0% (0/5) | 37% (3/8) |
|  | NR | 100% (5/5) | 0% (0/8) |

*Percentage of mice demonstrating complete responses (CR), partial responses (PR) and no responses (NR) for each treatment group. Complete responses refer to mice with complete regression of their tumour with no sign of tumours to the end of the experiment (80 days). Partial responses are tumours which demonstrated delays in time-to-endpoint-size, as compared with control mice (UV AV2). ( ) denote the number of positive mice out of the total number of mice in group.

Systemic Administration of AV1 and AV2 is Effective Against Disseminated Disease CT-26 cells when injected into the tail vein, seed tumours throughout the mouse although predominantly within the lungs, leading to mortality within 3-4 weeks. The lungs of four mice were examined 16 days after tumour cell injection and four days after treatment with UV-inactivated virus (FIG. 4D). These lungs were 3 times their normal mass due to tumour burden, evident as nodules on the lung surface. In contrast, tumour-bearing littermates receiving a single intravenous dose of AV2, 4 days prior to the time of sacrifice, had lungs with normal mass and few obvious tumour nodules. AV2 administered by intranasal installation also showed significant efficacy while a combination of intravenous and intranasal administration appeared optimum (FIG. 4D).

FIG. 4E shows the survival plots of mice seeded with lung tumours and then treated intranasally with UV inactivated virus, AV1 or AV2. The mean time to death (MTD) of animals treated with UV inactivated virus was approximately 20 days. However, mice treated with either AV1 or AV2 were completely protected. This experiment demonstrates the remarkable ability of AV1 and AV2 to produce durable cures in an aggressive, disseminated, immune-competent tumour model.

Discussion

A key difference between these attenuated viruses and previously reported oncolytic versions of VSV, is the inability of mutant M proteins to block interferon production in infected cells. VSV M is a multifunctional protein required for several key viral functions including: budding (Jayakar et al., 2000, J. Virol., 74:9818-9827) virion assembly (Newcomb et al., 1982, J. Virol., 41:1055-1062), cytopathic effect (Blondel et al., 1990, J. Virol., 64:1716-1725), and inhibition of host gene expression (Lyles et al., 1996, Virology, 225:172-180). The latter property has been attributed to the ability of M to block host RNA polymerase activity (Yuan et al., 2001, J. Virol, 75:4453-4458) or to inhibit the nuclear transport of both proteins and mRNAs into and out of the host nucleus (Her et al., 1997, ibid; von Kobbe et al., 2000, ibid). The results presented here using virus infection are consistent with blocks in nuclear transport being the major mechanism by which wild type VSV strains mitigate host antiviral response. The present analysis of infected cell transcripts provided little evidence to support a role for M protein in inhibiting host cell transcription but rather shows that VSV infection triggers an IRF-3 mediated stimulation of antiviral genes followed by an M protein mediated block of transport of primary response transcripts from infected cell nuclei. Particularly germane, to this study is the work from Dahlberg's group (Petersen et al., 2000, Mol. Cell. Biol., 20:8590-8601) and others (von Kobbe et al., 2000, ibid) that has shown, by transfection studies, that M protein can associate with nuclear pore proteins and effect a block in mRNA export.

While not intending to be bound by theory, it appears that host cell antiviral programs are initiated by activation of the latent transcription factors NFκB, c-JUN/ATF2 and IRF-3. Upon viral entry into the host cell, the transcription factors c-JUN and IRF-3 are phosphorylated by JNK and a recently identified virally activated kinase (John Hiscott, personal communication), respectively, while NFκB is released from its inhibitor IkB through the action of upstream IKK(s) (Di-Donato et al., 1997, Nature, 388:548-554). The activated transcription factors translocate to the nucleus and coordinately form an enhancesome complex at the IFN-β promoter; leading to IFN-β induction (Wathelet et al., 1998, ibid). This is referred to herein as the primary transcriptional response to virus infection. It has been postulated that a secondary transcriptional wave is triggered by the IFN-β dependent induction of a variety of interferon stimulated genes. The data presented here with wild type M protein helps to delineate the distinction between these primary and secondary transcriptional events as well as identify several novel viral response genes (GADD34, PUMA). Following infection with viruses harbouring mutant M proteins, it becomes clear that autocrine stimulation of the JAK/STAT signaling pathway by IFN-β leads to the production of secondary response genes like IRF-7 which in turn are critical for the tertiary induction of IFN-α genes (Morin et al., 2002, J. Mol. Biol., 316:1009-1022). Indeed the M protein block of secondary and tertiary transcripts can be overcome by expressing a constitutively active version of IRF-7 (from a viral promoter) even in the presence of wild type M protein.

One of the limitations of oncolytic therapy may be virus neutralization by pre-existing antibodies present in the human population (Ikeda et al., 1999, Nature Medicine, 5:881-887). Using an oncolytic virus, like VSV, which is not endemic in the human population, should provide a significant therapeutic advantage. While a dose dependency to oncolytic activity (six treatments are superior to one) at some point was found in this study, presumably as neutralizing antibodies are developed, additional doses provide no therapeutic gain. These results suggest that one of the critical determinants to successful viral therapy will be efficient delivery to the tumour site prior to the development of antiviral immune response. Clinically, it will likely be important to deliver the maximum tolerable virus dose as frequently as possible prior to the evolution of host mediated anti-viral response. The determination of the exact dose required for individual patients is well within the abilities of clinicians working in the field and, therefore, it is not necessary to discuss specific dosages herein.

Strategies involving immunosuppression of patients prior to virus therapy could in principle be useful, however, it has been found that an important component of viral oncolytic therapy is an anti-tumour response which is initiated by the expression of viral proteins on tumour cell surfaces (data not shown and Todo et al., 1999, Human Gene Therapy, 10:2741-2755). Perhaps other strategies, like the infusion of virus infected cells as shown herein, or coating of viral preparations with polymers (Fisher et al., 2001, Gene Ther., 8:341-348) will provide an opportunity to deliver therapeutics to tumour sites without compromising valuable host immune responses.

The data presented herein indicates that defects in interferon signalling frequently occur during tumour evolution, with a great majority of the cell lines in the NCI panel having an impaired response. Accumulating data has indicated that interferon is a multifunctional cytokine that can co-ordinately regulate cell growth, apoptosis and antiviral pathways. Perhaps during tumour evolution, the selection for relentless growth and loss of apoptosis outstrips the occasional need for anti-viral activity.

Ideally, an oncolytic virus will replicate preferentially in malignant cells, have the ability to spread from the primary tumour to sites of metastases and ultimately be cleared by the host. Evidence is presented herein that the attenuated viruses AV1 and AV2 embody all of these traits and, because of their ability to trigger antiviral responses in normal cells, may be exceptionally safe in vivo. Indeed, it has proven impossible to date, to select for VSV variants that are resistant to the antiviral effects of interferon (Novella et al., 1996, J. Virol., 70:6414-6417) and the ability of these IFN inducing mutants to protect the host in trans against infection with WT VSV has been demonstrated (FIG. 1D). It is possible, therefore, that in a population of viruses where the majority of particles are potent inducers of interferon, the possibility of a wild type variant rising to dominance is remote. The resulting "cytokine cloud" produced by infection with the IFN inducing virus would protect the host from the more virulent WT strain (see FIG. 5). Tumour killing would however, be unaffected as these cells have been shown to be defective in responding to such a "cytokine cloud". Hence the therapeutic index is increased, further improving the potential of the oncolytic viruses as cancer therapeutics.

Example 2

Rescued Mutant VSVs

Figure 7:
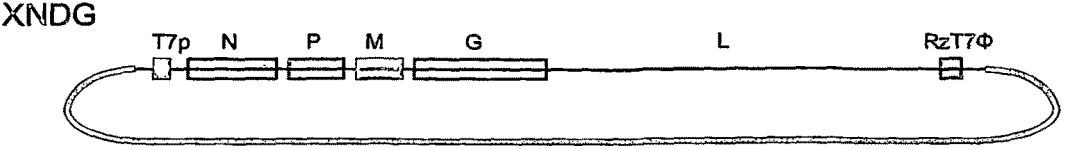
FIG. 7 depicts the sequence of the relevant portion of the VSV M protein for rescued mutants XNDG M4 and M5. (SEQ ID NO: 21, 25 and 26)
Figure 8:
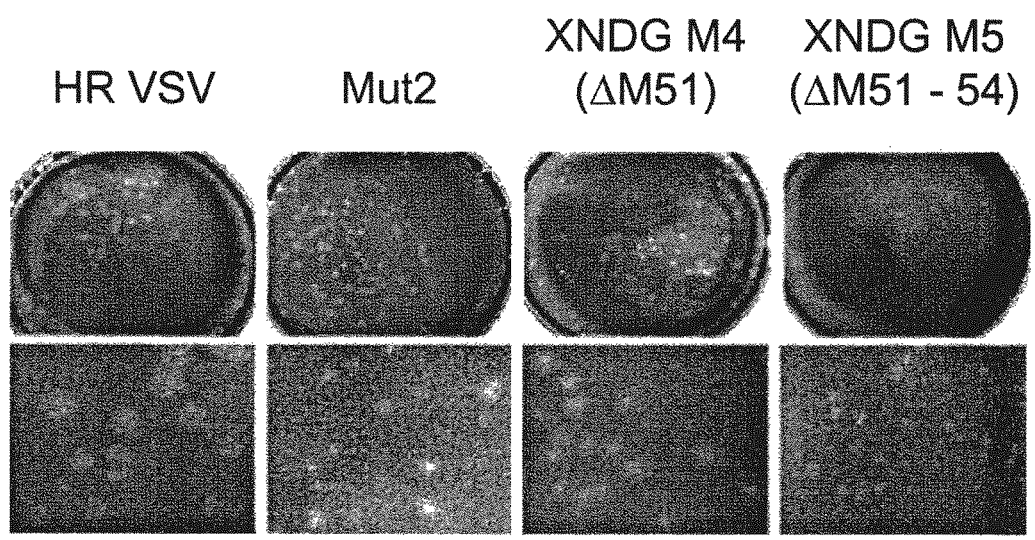
FIG. 8 depicts that the rescued mutant VSVs XNDG M4 and M5 have similar plaque sizes to the Mut2 mutant VSV.

A series of recombinant viruses were constructed to test the range of mutations that are useful for the generation of interferon inducing mutants. To this end, a chimeric virus backbone was created which contained the N, G and L genes from the plasmid pXN-1 (Schnell M J, Buonocore L, Whitt M A and Rose J K (1996) J. Virology 4, 2318-2323) and the P and M genes from AV1. Once created a series of viruses differing only in their M genes was generated by sequentially substituting in M gene variants as shown in the accompanying Figures (FIGS. 6 and 7). For instance, XNDG M4 contains the N, G and L genes from pXN-1, the P gene from AV1 and an M gene with methionine 51 deleted. XNDG M5 harbours an M gene that has a four amino acid deletion of methionine 51, Aspartate 52, Threonine 53 and Histidine 54 (FIG. 7). As we show in Table 4 (below) these two mutants are equally effective in killing three tumourigenic cell human cell lines as a naturally occurring mutant (Mut 2 or AV1) which has a methionine 51 converted to an arginine (i.e. M51R). Since XNDG M4 and M5 are deletion mutants it will be much more difficult for these recombinant viruses to revert back to the original methionine 51 genotype. Furthermore, while the engineered viruses are still able to effectively kill tumour cells, they form small plaques on interferon responsive cells indicating that these viruses are attenuated for growth in cells which can respond to interferon (FIG. 8).

To perform the plaque assay, Vero cells were seeded onto 60 mm diameter tissue culture dishes at confluency in aMEM+10% bovine serum and allowed to attach for at least 3 hours under normal tissue culture conditions. Serial dilutions of the sample virus suspension are made in half-log increments (eg. 10-4, 10-4 1/2, 10-5, 10-5 1/2, . . . etc.) in serum-free aMEM. Media was aspirated from the 60 mm dishes, 100 µl of virus suspension was added per dish and the dishes were incubated under normal tissue culture conditions for 45 minutes. Following the 45 minute incubation, the dishes were overlayed with 3 ml of a 1:1 mixture of 1% agarose+(2×aMEM+20% fetal bovine serum) at 42° C. The dishes were then incubated overnight and plaques are counted the following morning.

OVCAR (a human ovarian cancer cell line), 293T (a human kidney cell line transformed by large T antigen from SV 40) and U2OS (a human osteosarcoma cell line) cell lines were infected with AV1 (Mut2), XNDG M4 and XNDG M5 virus and cell viability was determined after a period of time, using the MTS assay as described above. The data provided in Table 4 demonstrates that rescued mutant VSVs have similar killing properties in comparison to AV1.

TABLE 4

MOI required to kill 50% of cells in 48 hours as measured by the MTS assay.

|  | AV1 | XNDG M4 | XNDG M5 |
|---|---|---|---|
| OVCAR3 | 0.0096 | 0.0228 | 0.0105 |
| 293T | 0.0096 | 0.0138 | 0.04056 |
| U2OS | 0.03 | 0.0186 | 0.0156 |

Example 3

GFP-M Protein Fusion Proteins

Figure 9:
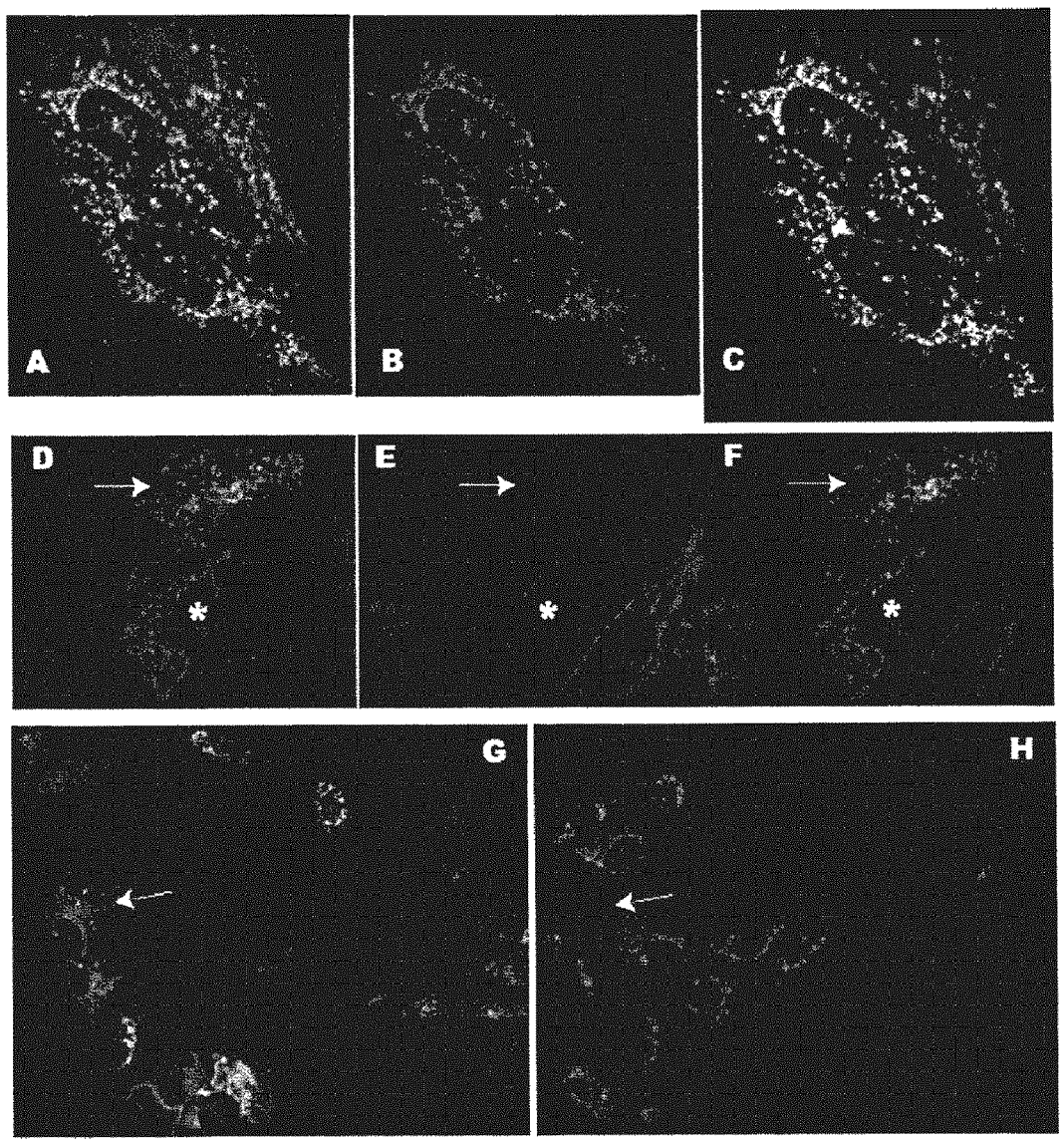
FIGS. 9A, B and C depict cells transfected with amino-terminal 72 amino acids of VSV fused to GFP (WT+72-GFP-N1, green) and OCT-DsRed2 (mitochondrial marker, red). C. Merged image showing co-localisation of M-GFP and OCT-DsRed2. D, E and F. Cells transfected with WT+72-GFP-N1 and stained with Mitotracker Red. Arrow indicates typical transfected cell displaying punctuate mitochondria and reduced Mitotracker staining. Asterisk indicates a transfected cell with reticular (normal) mitochondria indicating co-localisation of WT+72-GFP-N1 and Mitotracker staining (merged image F). G and H. Cells transfected with WT+72-GFP-N1 and stained with Mitotracker Red. Transfected cells have punctuate mitochondria and reduced Mitotracker staining (arrow).

When fused to the amino terminus of green fluorescent protein (GFP), the amino terminus of VSV matrix (M) protein (aminoM+72-GFP-N1) targets this fusion protein to the mitochondria (FIGS. 9 and 10). The first 72 amino acids of VSV Indiana M are capable of targeting GFP. A fusion protein initiated at methionine 33 (M33) is also able to target GFP to mitochondria while the first 50 amino acids alone are not. Methionine 51 (M51) is not required. When fused to the C terminus of GFP these sequences do not target the fusion protein to mitochondria, therefore, these sequences must be at the amino terminus of a recombinant protein to perform this targeting.

As shown in FIGS. 9 and 10, when a fusion between the amino terminal 72 amino acids and GFP (aminoM+72-GFP-N1) is transiently expressed in cultured cells: 1) the fusion protein is targeted to the mitochondria, 2) the mitochondria lose the usual reticulotubular organisation and collapse into punctate perinuclear structures that 3) lose the membrane potential. These are the hallmarks of a dying cell.

VSV matrix protein has been recognised as a toxic protein that plays a role in the cytotoxicity of the virus. Transcription of the M protein initiates at three alternative ATG codons (M1, M33 and M51) and a virus mutated at M33 and M51 such that it cannot produce the shorter isoforms has significantly reduced cytotoxicity. A virus that has a mutant VSV M protein no longer targeted to mitochondria will be less cytotoxic.

Example 4

Protection Against VSV-Induced Morbidity

This study demonstrates that systemically administered mutant VSV (ΔM51) can protect against a lethal intracranial dose of VSV.

Groups of 8 week old female Balb/C mice were injected intravenously (primed) with either PBS, WT GFP VSV (1e8 pfu) or ΔM51 GFP VSV (1e8 pfu). Twenty four hours later, all mice were inoculated intracanially with 2e7 pfu of ΔM51 VSV (in 5 μl PBS) and monitored for signs of morbidity, and paralysis.

The results are presented in FIGS. 17A and 17B. FIG. 17A provides a Kaplan Meyer survival plot demonstrating that 100% of ΔM51 primed mice survived while all WT and PBS control primed mice developed hindlimb paralysis and were euthanized. FIG. 17B is a plot of mouse weights over time, following intravenous treatment. The ΔM51 primed mice demonstrated no weight loss, while WT and PBS control mice showed extreme weight loss prior to their euthanization.

Example 5

Interferon Production Following VSV Infection

The data presented in this study demonstrate that cells infected with mutant VSV secreted IFN-α and IFN-β, while those cells infected with WT VSV either did not produce IFN-α and IFN-β, or did so in much smaller amounts.

β-Interferon

Figure 18:
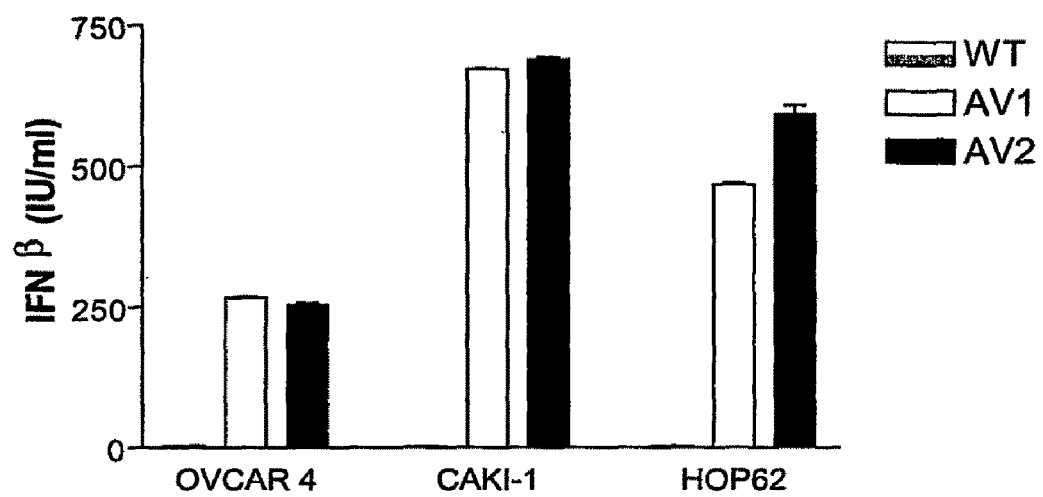
FIG. 18 graphically depicts relative β-IFN production in OVCAR 4, CAKI-1 and HOP62 cells infected with WT VSV or a mutant VSV (AV1 or AV2).

OVCAR4, CAKI-1 and HOP62 cells were infected (MOI of 10 pfu) with either WT or mutant VSV strains. The infected cells were assayed by ELISA for IFN-β production 10 hours post infection. AV1 and AV2 infected cells and not WT VSV infected cells produce secreted IFN-β. The ELISA was performed using a commercially available human IFN-β detection kit (TFB INC; Tokyo Japan). The results of this study are shown graphically in FIG. 18.

The cell lines used in this study are commercially available, for example from the New Drug Development Program of the NCI. The three cell lines are all human cancers that were selected for this study since they fall in the 20% of cancers that are somewhat interferon responsive. OVCAR are ovarian cancer cells, HOP62 are lung cancer cells and CAKI-1 are renal cancers. In each case the cells were infected as described in the MTS assay (see Example 1).

α-Interferon

Mouse serum IFN-α levels were assayed using a mouse Interferon-Alpha ELISA kit (PBL Biomedical). Balb/C females (10 weeks old; Charles River) were injected intravenously with either PBS or 1×10⁸ pfu of WT GFP or AV3 GFP (wherein AV3 is an engineered version of VSV where methionine 51 has been completely deleted) diluted in PBS. At the indicated times post infection, blood was collected from the saphenous vein of each mouse into heparinized tubes and centrifuged to obtain serum. For each sample, 5 μl of serum was diluted in 95 μl of PBS and assayed as per manufacturer's instructions. The results provided in Table 5, below, demonstrate that the mice infected with the ΔM51 mutant produced IFN-α earlier and in greater amounts than mice infected with WT VSV. The naïve mice did not produce detectable amounts of IFN-α.

TABLE 5

| | Serum Interferon-α (pg/ml) | | |
|---|---|---|---|
| Time (h) | Naïve (n = 2) | WT (n = 3) | ΔM51 (n = 3) |
| 0 | neg. | neg. | neg. |
| 1 | neg. | neg. | 559 ± 116 |
| 6 | neg. | 8197 ± 2726 | 25,213 ± 322 | neg. = below the level of detection of the assay (<200 pg/ml);
time refers to hours post infection.

Example 6

In vivo treatment of mice with Δ51-VSV was found to dramatically augment cytotoxic T lymphocyte (CTL)-mediated lysis of CT26 tumour cell targets compared to lysis by splenocytes from tumour-bearing, VSV-untreated mice.

Balb/c mice with established CT26 subcutaneous tumours were treated with or without $5\times10^8$ pfu ΔM51 VSV intravenously. After 7 days, splenocytes were harvested and cultured in a 5:1 ratio with irradiated CT26 tumour cells. After 7 days of in vitro stimulation splenocytes were assayed for anti-CT26 CTL activity. The results of this study are graphically depicted in FIG. 19A, in which % of tumour-specific lysis above background spontaneous lysis of CT26 target tumour cells in the absence of effector splenocytes, is plotted against effector:target ratio (Target cells are the tumour cells, the splenocytes are the effector or killer cells).

Qualitative differences were also observed in immune responses elicited by WT or ΔM51 viruses. Balb/c mice were treated with $5\times10^8$ pfu of wild-type or Δ51-VSV intravenously, and after 7 days, splenocytes were harvested and co-cultured with irradiated CT26 tumour cells. After 7 days in culture, splenocytes were assayed for lysis against CT26 cells, with or without prior NK cell depletion with antibody-conjugated magnetic beads. Treatment of mice with both wild-type and ΔM51-VSV primed splenocytes for potent primary immune response generation to CT26 tumour antigens in vitro, with no previous in vivo exposure to those tumour antigens during viral infection. This indicates that VSV therapy primes splenocytes in vivo for subsequent primary response generation in vitro against novel antigens. The lytic activity against CT26 cells following wild-type VSV therapy was NK-dependent. The lytic activity against CT26 cells following ΔM51-VSV therapy was CTL-mediated, which indicates qualitatively distinct immunological priming events following therapy with ΔM51 versus WT VSV. These results are depicted in FIG. 19B. This data also suggests the superior capacity of ΔM51 VSV to elicit potent adaptive immune responses (CD8+ T cell-mediated lysis) with potential for development of protective immunological memory, in contrast with wild-type infection which generated a primarily innate, NK cell-mediated effector mechanism against CT26 cells.

This study shows that the mutant virus induces a qualitatively different response than wild type virus. The induction of CTL cells in this assay is only seen with the mutant virus. The CTL response will be a long term protective response whereas the NK response will not have a memory. The induction of this distinct response is likely attributable to the induction of cytokines by the mutant virus.

Example 7

Immunohistochemical Staining of Mutant VSV Treated Tumours

Figure 20:
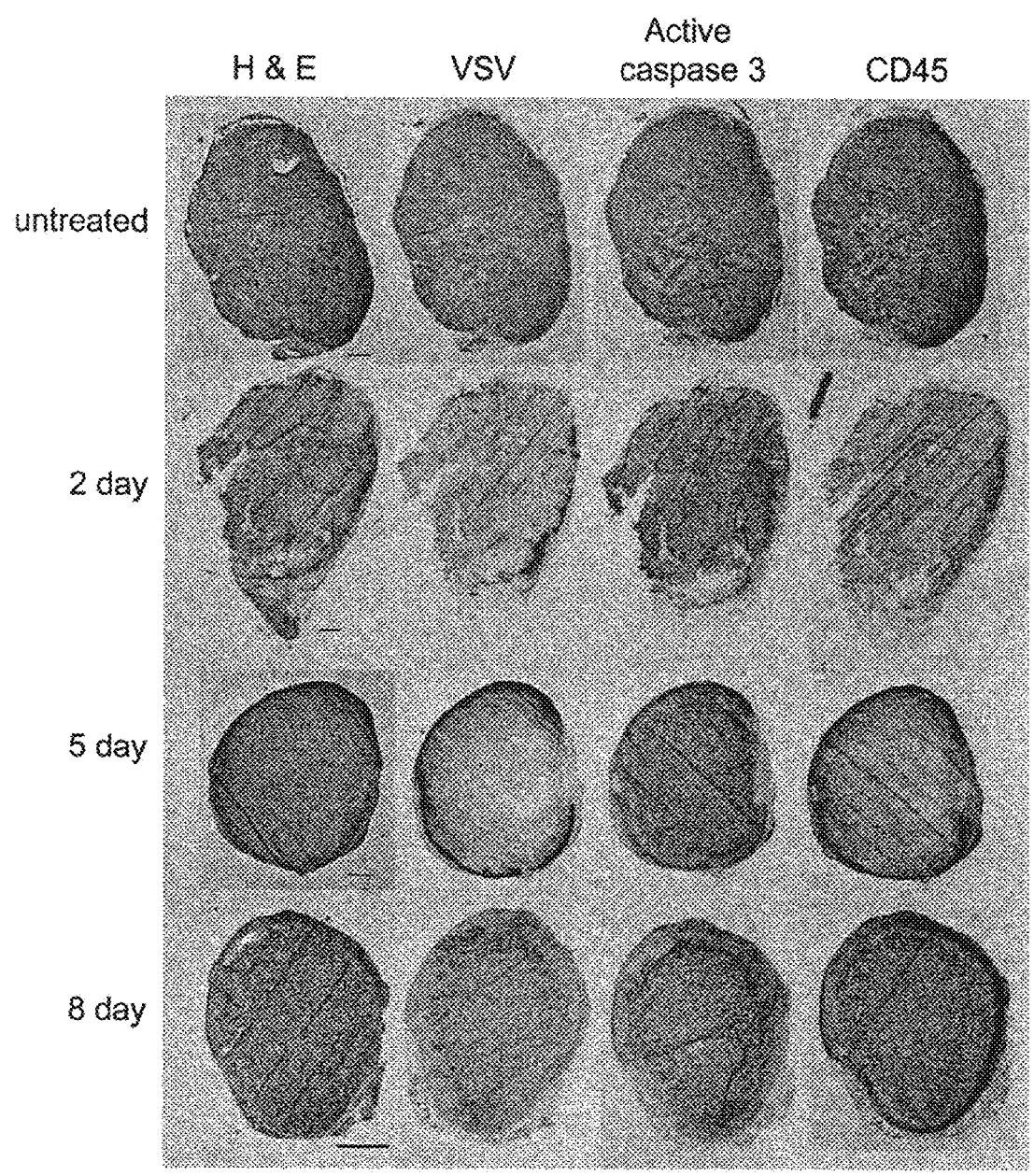
FIG. 20 depicts immunohistochemically stained sections of CT26 tumours from Δ51M VSV GFP treated mice bearing subcutaneous CT26 tumours.

In order to study the effect of mutant VSV on tumours, Balb/c mice bearing subcutaneous CT26 tumours were treated intravenously with ΔM51 VSV GFP. After, 2, 5 or 8 days the mice were euthanized and tumours were snap frozen and later sectioned (5 μm) and immunohistochemically stained for VSV, active caspase 3 and CD45, a pan-leukocyte marker. Standard techniques were used in this study. Photographs of the stained sections are shown in FIG. 20. The positive stain is brown, while all nuclei are counterstained blue with hematoxylin. H&E staining shows tumour morphology (H &E staining is a non-specific stain which shows the overall structure of the tumour).

The immunohistochemical staining of the mutant VSV treated tumours revealed massive apoptosis and leukocyte accumulation. This study demonstrates that mutant VSV is an excellent oncolytic agent because it induces the death of tumour cells that have not even been infected (i.e. caspase 3+ cells that have undergone apoptosis). While not intending to be bound by theory, this is likely because again the mutant virus induces the production of cytotoxic cytokines that kill tumour cells in advance of the infecting virus. Furthermore, the mutant virus recruits leukocytes (CD45+ cells) that can infiltrate and attack the tumour. The CD45+ cells follow in after the mutant virus infected cells, again in response to the cytokines induced by the virus infection of tumour cells.

All publications, patents and patent applications mentioned in this specification are indicative of the level of skill of those skilled in the art to which this invention pertains and are herein incorporated by reference to the same extent as if each individual publication, patent, or patent applications was specifically and individually indicated to be incorporated by reference.

The embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method of inhibiting tumor cell growth in an animal, the method comprising: administering a mutant vesicular stomatitis virus (VSV) to the tumor cell, wherein the mutant VSV comprises a mutation corresponding to a ΔM51 mutation in the gene encoding the matrix (M) protein.

2. The method of claim 1, wherein the M protein of the mutant VSV comprises a ΔM51-54 mutation.

3. The method of claim 1, wherein the M protein of the mutant VSV comprises a ΔM51-57 mutation.

4. The method of claim 1, wherein the M protein of the mutant VSV further comprises a mutation of the V221 amino acid of the M protein.

5. The method of claim 4, wherein the M protein of the mutant VSV comprises a ΔV221 mutation.

6. The method of claim 4, wherein the M protein of the mutant VSV comprises a ΔV221-226 mutation.

7. The method of claim 4, wherein the M protein of the mutant VSV comprises a substitution of the V221 amino acid with one or more amino acids.

8. The method of claim 7, wherein the substitution of the V221 amino acid comprises a substitution with a phenylalanine.

9. The method of claim 4, wherein the M protein of the mutant VSV further comprises a mutation of the S226 amino acid of the M protein.

10. The method of claim 1, wherein the M protein of the mutant VSV further comprises a mutation of the S226 amino acid of the M protein.

11. The method of claim 10, wherein the M protein of the mutant VSV comprises a ΔS226 mutation.

12. The method of claim 10, wherein the M protein of the mutant VSV comprises a substitution of the S226 amino acid with one or more amino acids.

13. The method of claim 12, wherein the substitution of the S226 amino acid comprises a substitution with an arginine.

14. The method of claim 1, wherein the M protein of the mutant VSV comprises a mutation selected from the group of: ΔM51/V221F; ΔM51-54/V221F; ΔM51-57/V221F; ΔM51/S226R; ΔM51-54/S226R; and ΔM51-57/S226R.

15. The method of claim 1, wherein the M protein of the mutant VSV comprises a mutation selected from the group of: ΔM51/V221F/S226R; ΔM51-54/V221F/S226R; and ΔM51-57/V221F/S226R.

16. The method of claim 1, wherein the M protein of the mutant VSV further comprises one or more mutations selected from the group consisting of ΔV221-226, V221X, and S226X.

17. The method of claim 1, wherein the tumor cell is selected from the group consisting of a leukemia, a lung carcinoma, a colon carcinoma, a central nervous system tumor cell, a melanoma, an ovarian carcinoma, a renal carcinoma, a prostate tumor cell, and a breast tumor cell.

18. The method of claim 1, further comprising a heterologous nucleic acid.

19. The method of claim 18, wherein the heterologous nucleic acid encodes a therapeutically active molecule.

20. The method of claim 1, wherein the animal is a human.

21. The method of claim 1, wherein the mutant VSV is administered intravenously.

22. The method of claim 1, wherein the mutant VSV is administered intranasally.

23. The method of claim 1, wherein the mutant VSV is administered intranasally and intravenously.

24. The method of claim 1, wherein the mutant VSV is administered by administering cells infected with the virus.

25. The method of claim 1, wherein the method is used to treat a cancer that can be relieved by cytokine release and wherein the mutant VSV is capable of triggering the production of one or more cytokines in an infected cell.

* * * * *